US007989162B2

(12) United States Patent
Bartholomeusz et al.

(10) Patent No.: US 7,989,162 B2
(45) Date of Patent: *Aug. 2, 2011

(54) VIRAL VARIANTS WITH ALTERED SUSCEPTIBILITY TO NUCLEOSIDE ANALOGS AND USES THEREOF

(75) Inventors: Angeline Ingrid Bartholomeusz, Carnegie (AU); Stephen Alister Locarnini, St. Kilda (AU); Anna Ayres, West Brunswick (AU); Peter William Angus, East Ivanhoe (AU); William Sievert, Clayton (AU)

(73) Assignees: Melbourne Health, Parkville (AU); Austin Health, Victoria (AU); Southern Health, Clayton, Victoria ( * ) Notice: Subject to any disclaimer, the term of this patent is extended or adjusted under 35 U.S.C. 154(b) by 0 days.

This patent is subject to a terminal disclaimer.

(21) Appl. No.: 12/142,917

(22) Filed: Jun. 20, 2008

(65) Prior Publication Data

US 2009/0081667 A1    Mar. 26, 2009

Related U.S. Application Data

(63) Continuation of application No. 10/911,464, filed on Aug. 4, 2004, now Pat. No. 7,405,039, which is a continuation of application No. PCT/AU03/00111, filed on Feb. 5, 2003.

(30) Foreign Application Priority Data

Feb. 7, 2002  (AU) ........................... PS0370
Mar. 21, 2002  (AU) ........................... PS1269

(51) Int. Cl.
C12Q 1/70 (2006.01)
A61K 39/00 (2006.01)
A61K 39/29 (2006.01)
A61K 39/25 (2006.01)

(52) U.S. Cl. .... 435/5; 424/184.1; 424/185.1; 424/189.1

(58) Field of Classification Search ........................ None
See application file for complete search history.

(56) References Cited

U.S. PATENT DOCUMENTS

| 4,946,677 | A | 8/1990 | Dorner et al. |
|---|---|---|---|
| 5,237,053 | A | 8/1993 | Dorner et al. |
| 6,100,380 | A | 8/2000 | Green et al. |
| 6,436,391 | B1 | 8/2002 | Foster et al. |
| 6,555,311 | B1 | 4/2003 | Locarnini et al. |
| 7,405,039 | B2 * | 7/2008 | Bartholomeusz et al. ........ 435/5 |
| 7,422,848 | B2 | 9/2008 | Bozdayi |
| 2003/0124096 | A1 | 7/2003 | Locarnini et al. |
| 2004/0005541 | A1 | 1/2004 | Bartholomeusz et al. |
| 2004/0194155 | A1 | 9/2004 | Delaney et al. |
| 2006/0051743 | A1 | 3/2006 | Bartholomeusz et al. |

FOREIGN PATENT DOCUMENTS

| AU | 734831 | 6/2001 |
|---|---|---|
| CA | 2 309 379 | 12/2001 |
| EP | 02 52 064 | 6/1987 |
| EP | 07 17 106 | 11/1995 |
| WO | WO 90/06696 | 6/1990 |
| WO | WO 93/24636 | 12/1993 |
| WO | WO 97/41234 | 11/1997 |
| WO | WO 98 21317 | 5/1998 |
| WO | WO 00/61758 | 10/2000 |
| WO | WO 01 57244 A1 | 8/2001 |
| WO | WO 01 94559 A1 | 12/2001 |
| WO | WO 03/066841 | 8/2003 |
| WO | WO 2004/031224 | 4/2004 |

OTHER PUBLICATIONS

Bartholomeusz et al., U.S. Appl. No. 12/303,942, filed Dec. 8, 2008.*
Angus et al. "Resistance to oadefovir dipivoxil therapy associated with the selection of a novel mutation in the HBV polymerase" 2003, *Gastro.*, 125(2):292-7.
Barbhaiya et al. "Iron uptake and detection of an outer membrane iron-siderophore receptor protein from *Pseudomanas aeruginosa* PA01" 1998, *FEMS Microbiol. Lett.*, 51:169-72.
Bartenschlager et al. "Hepadnaviral assembly is initiated by polymerase binding to the encapsidation signal in the viral RNA genome" 1992, *EMBO. J.*, 7:4185-92.
Bartholomeusz et al. "Mutations in the hepatitis B virus polymerase gene that are associated with resistance to famciclovir and lamivudine" 1997, *Int. Anti. News*, 5(8):123-4.
Bartholomeusz et al. "Significance of mutations in the hepatitis B virus polymerase selected by nucleoside analogues and implications for controlling chronic disease" 1998, *Viral Hepatitis Rev.*, 4:167-87.
Benhamou et al. "Safety and efficacy of adefovir dipivoxil in patients co-infected with HIV-1 and lamivudine-resistant hepatitis B virus: an open-label pilot study" 2001, *Lancet*, 358:718-23.
Benzaria et al. "Synthesis, in vitro antiviral evaluation, and stability studies of bis(S-acyl-2-thioethyl) ester derivatives of 9-[2-(phosphonomethoxy)ethyl]adenine (PMEA) as potential PMEA prodrugs with improved oral bioavailability" 1996, *J. Med. Chem.*, 39:4958-65.

(Continued)

*Primary Examiner* — Zachariah Lucas
*Assistant Examiner* — Benjamin P Blumel
(74) *Attorney, Agent, or Firm* — Baker Botts L.L.P.

(57) ABSTRACT

The present invention relates generally to viral variants exhibiting reduced sensitivity to particular agents and/or reduced interactivity with immunological reagents. More particularly, the present invention is directed to hepatitis B virus (HBV) variants exhibiting complete or partial resistance to nucleoside analogs and/or reduced interactivity with antibodies to viral surface components including reduced sensitivity to these antibodies. The present invention further contemplates assays for detecting such viral variants, which assays are useful in monitoring anti-viral therapeutic regimens and in developing new or modified vaccines directed against viral agents and in particular HBV variants. The present invention also contemplates the use of the viral variants to screen for agents capable of inhibiting infection, replication and/or release of the virus.

3 Claims, 12 Drawing Sheets

OTHER PUBLICATIONS

Bowie et al. "Deciphering the Message in Protein Sequences: Tolerance to Amino Acid Substitutions" 1990, *Science*, 247(4948):1306-10.

Brown et al. "Cloning and characterization of the katB gene of *Pseudomonas aeruginosa* encoding a hydrogen peroxide-inducible catalase: purification of KatB, cellular localization, and demonstration that it is essential for optimal resistance to hydrogen peroxide" 1995, *J. Bacteriol.*, 177:6536-44.

Burgess et al. "Possible dissociation of the heparin-binding and mitogenic activities of heparin-binding (acidic fibroblast) growth factor-1 from its receptor-binding activities by site-directed mutagenesis of a single lysine residue" 1990, *J. Cell Biol.*, 111:2129-38.

Calio et al. "Enhancement of natural killer activity and interferon induction by different acyclic nucleoside phosphonates" 1994, *Antiviral Res.*, 23:77-89.

Chang et al. "Mechanism of translation of the Hepadnaviral polymerase (P) gene" 1990, *Proc. Natl. Acad. Sci. USA*, 87:5158-62.

Coates et al. "(-)-2'-deoxy-3'-thiacytidine is a potent, highly selective inhibitor of human immunodeficiency virus type 1 and type 2 replication in vitro" 1992, *Antimicrob. Agents Chemother.*, 36:733-9.

Database EMBL [Online] EBI; Hepatitis B virus mutante polymerase gene, Jun. 28, 2000, Yeh C.-T.: XP002510516, retrived from EBI Database accession No. AF156492.

Database EMBL [Online] EBI; Woodchuck hepatitis virus, Sep. 20, 2001, Yamamoto, T: XP002510517, retrived from EBI Database accession No. AF410856.

Database UniProt [Online], Jul. 1, 1993; "Protein P [Includes: DNA-directed DNA polymerase (EC<A HREF="http://srs.ebi.ac.uk/srsbin/cgi-bin/wgetz?[enzyme-ECNumber:2.7.7.49]+-e">2.7.7</A); RNA-directed DNA polymerase (EC < A HREF="http://srs.ebi.ac.uk/srsbin/cig-bin/wgetz?[enzyme-ECNumber:2.7.7.49]+-e">2.7.7.49</A>); Ribonuclease H (EC <A>".

Dienstag et al. "Lamivudine as initial treatment for chronic Hepatitis B in the United States" 1999, *N. Engl. J. Med.*, 341:1256-63.

Doong et al. "Inhibition of the replication of Hepatitis B virus in vitro by 2',3'-dideoxy-3'-thiacytidine and related analogues" 1991, *Proc. Natl. Acad. Sci. USA*, 88:8495-9.

Estacio et al. "Nucleotide sequence of a hepatitis B virus genome of subtype adw isolated from a Philippino: Comparison with the reported three genomes of the same subtype" 1988, *J. Gast. Hepat.*, 3:215-22.

Fernandes et al. "Antibodies to cell envelope proteins of *Pseudomonas aeruginosa* in cystic fibrosis patients" 1981, *Infect. Immun.*, 33:527-32.

Fiser et al. "Modeling of loops in protein structures" 2000, *Protein Sci.*, 9:1753-73.

Frick et al. "Pharmacokinetics, oral bioavailability, and metabolic disposition in rats of (-)-cis-5-fluoro-1-[2-(hydroxymethyl)-1,3-oxathiolan-5-yl] cytosine, a nucleoside analog active against human immunodeficiency virus and hepatitis B virus" 1993, *Antimicrob. Agents Chemother.*, 37: 2285-92.

Gardsvoll et al. "Mapping part of the functional epitope for ligand binding on the receptor for urokinase-type plasminogen activator by site-directed mutagenesis" 1999, *J. Biol. Chem.*, 274(53):37995-8003.

Georgiadis et al. "Mechanistic implications from the structure of a catalytic fragment of Moloney murine leukemia virus reverse transcriptase" 1995, *Structure*, 3:879.

Gilson et al. "A placebo-controlled phase I/II study of adefovir dipivoxil in patients with chronic hepatitis B virus infection" 1999, *J. Viral Hepat.*, 6:387-95.

Greenberg "Bacterial genomics: pump up the versatility" 2000, *Nature*, 406:947-8.

Heathcote et al. "Loss of serum HBV DNA and HBeAg and seroconversion following shoert term (12 weeks) Adefovir Dipivoxil therapy in in chronic hepatitis B: two two placebo-controlled phase II studies" 1998, *Hepatol.*, 28:A620.

Hess et al. "Inhibition of hepatits B virus specific DNA polymerase by intercalating agents" 1980, *Med. Microbiol. Immunol.*, 168:25-34.

Hoyer-Hansen et al. "The intact urokinase receptor is required for efficient vitronectin binding: receptor cleavage prevents ligand interaction" 1997, *FEBS Lett.*, 420(1):79-85.

Jarvis et al. "A review of its therapeutic potential in chronic Hepatitis B" 1999, *Drugs* 58:101-41.

Khan et al. "The functional analysis of directed amino-acid alterations in ZntR from *Escherichia coli*" 2002, *Biochem. Biophys. Res. Commun.*, 299(3):438-45.

Kukor et al. "Cloning and expression of the catA and catBC gene clusters from *Pseudomonas aeruginosa* PAO" 1988, *J. Bacteriol.*, 170:4458-65.

Landford et al. "Mapping of the Hepatitis B virus reverse transcriptase TP and RT domains for transcomplementation for nucleotide priming and by protein-protein interaction" 1999, *J. Virol.*, 73:1885-93.

Lazar et al. "Transforming growth factor alpha: mutation of aspartic acid 47 and leucine 48 results in different biological activities" 1988, *Mol. Cell. Biol.*, 8:1247-52.

Lesburg et al. "Crystal structure of the RNA-dependent RNA polymerase from Hepatitis C virus reveals a fully encircled active site" 1999, *Nat. Struct. Biol.*, 6(10):937-43.

Liaw et al. "Acute exacerbation and Hepatitis B virus clearance after emergence of YMDD motif mutation during lamivudine therapy" 1999, *Hepatol.*, 30:567-72.

Ma et al. "Bacterioferritin A modulates catalase A (KatA) activity and resistance to hydrogen peroxide in *Pseudomonas aeruginosa*" 1999, *J. Bacteriol.*, 181:3730-42.

Mack et al. "Hepatitis B virus particles contain a polypeptide encoded by the largest open reading frame: a putative reverse transcriptase" 1988, *J. Virol.*, 62:4786-90.

Meyer et al. "Pyoverdin-facilitated iron uptake in *Pseudomonas aeruginosa*: immunological characterization of the ferripyoverdin receptor" 1990, *Mol. Microbiol.*, 4:1401-5.

Miller et al. "Adefovir and tenofovir susceptibilities of HIV-1 after 24 to 48 weeks of adefovir dipivoxil therapy: genotypic and phenotypic analyses of study GS-96-408" 2001, *JAIDS.*, 27(5):450-8.

Nakamura et al. "Telomerase catalytic subunit homologs from fission yeast and human" 1997, *Science*, 277:955-9.

Ngo et al. "Computational Complexity, Protein Structure Prediction, and the Levinthal Paradox" 1994, *The protein folding problem and tertiary structure prediction*, Merz et al. (ed.), Birkhauser, Boston, MA, 433 & 492-5.

Nurizzo et al. "N-terminal arm exchange is observed in the 2.15 A crystal structure of oxidized nitrite reductase from *Pseudomonas aeruginosa*" 1997, *Structure*, 5:1157-71.

Parkhill et al., as published Oct. 15, 2001. Catalase [*Yersinia pestis*]. Genbank Accession No. NP_404811 GI:16121498.

Perrillo et al. "Adefovir dipivoxil for the treatment of lamivudine-resistant hepatitis B mutants" 2000, *Hepatol.*, 32:129-34.

Peters et al. "Fulminant hepatic failure resulting from lamivudine-resistant hepatitis B virus in a renal transplant recipient: durable response after orthotopic liver transplantation on adefovir dipivoxil and hepatitis B immune globulin" 1999, *Transpl.*, 68:1912-4.

Ploug et al. "Chemical modification of the urokinase-type plasminogen activator and its receptor using tetranitromethane. Evidence for the involvement of specific tyrosine residues in both molecules during receptor-ligand interaction" 1995, *Biochem.*, 34(39):12524-34.

Ploug et al. "Identification of specific sites involved in ligand binding by photoaffinity labeling of the receptor for the urokinase-type plasminogen activator. Residues located at equivalent positions in uPAR domains I and III participate in the assembly of a composite ligand-binding site" 1998, *Biochem.*, 37(47):16494-505.

Ploug et al. "Ligand interaction between urokinase-type plasminogen activator and its receptor probed with 8-anilino-1-naphthalenesulfonate. Evidence for a hydrophobic binding site exposed only on the intact receptor" 1994, *Biochem.*, 33(30):8991-7.

Ploug et al. "Photoaffinity labeling of the human receptor for urokinase-type plasminogen activator using a decapeptide antagonist. Evidence for a composite ligand-binding site and a short interdomain separation" 1998, *Biochem.*, 37(11):3612-22.

Poch et al. "Identification of four conserved motifs among the RNA-dependent polymerase encoding elements" 1989, *EMBO J.*, 8:3867-74.

Price et al. "Inhibition of the replication of hepatitis B virus by the carbocyclic analogue of 2'-deoxyguanosine" 1989, *Proc. Natl. Acad. Sci. USA*, 86(21):8541-4.

Radziwil et al. "Mutational analysis of the Hepatitis B virus P gene product: domain structure and RNase H activity" 1990, *J. Virol.*, 64:613-20.

Rodgers et al. "The structure of unliganded reverse transcriptase from the human immunodeficiency virus type 1" 1995, *Proc. Natl. Acad. Sci. USA*, 92(4)1222-6.

Sali et al. "Comparative protein modelling by satisfaction of spatial restraints" 1993, *J. Mol. Biol.*, 234:779-815.

Sarafianos et al. "Structures of HIV-1 reverse transcriptase with pre- and post-translocation AZTMP-terminated DNA" 2002, *EMBO J.*, 21(23):6614-24.

Sawaya et al. "Crystal structure of rat DNA polymerase β: Evidence for a common polymerase mechanism" 1994, *Science*, 264(5167):1930-5.

Sipos et al. "Cloning and sequencing of the genes coding for the 10- and 60-kDa heat shock proteins from *Pseudomonas aeruginosa* and mapping of a species-specific epitope" 1991, *Infect. Immun.*, 59:3219-26.

Sompolinsky et al. "An antigen common to a wide range of bacteria. I. The isolation of a 'common antigen' from *Pseudomonas aeruginosa*" 1980, *Acta. pathol. Microbiol. Scand. B*, 88:43-149.

Stephens et al. "Heparin binding to the urokinase kringle domain" 1992, *Biochem.*, 31:7572-9.

Stover et al. "Complete genome sequence of *Pseudomonas acruginosa* PA01, an opportunistic pathogen" 2000, *Nature*, 406:959-64.

Stover et al., as published Sep. 10, 2001, "catalase [*Pseudomonas acruginosa*]" Genbank Accession No. NP_252926.1 GI:15599432.

Stuyver et al. "Line probe assay for monitoring drug resistance in hepatitis B virus-infected patients during antiviral therapy" 2000, *J. Clin. Micro.*, 38(2):702-7.

Suo et al. "Selective inhibition of HIV-1 reverse transcriptase by an antiviral inhibitor, (R)-9-(2-Phosphonylmethoxypropyl)adenine" 1998, *J. Biol. Chem.*, 273(42): 27250-8.

Tavis et al. "The duck Hepatitis B virus polymerase is activated by its RNA packaging signal" 1998, *J. Virol.*, 72:5789-96.

Toh et al. "Sequence homology between retroviral reverse transcriptase and putative polymerases of Hepatitis B virus and cauliflower mosaic virus" 1983, *Nature*, 305:827-9.

Urban et al. "In vitro activity of Hepatitis B virus polymerase: requirement for distinct metal ions and the viral epsilon stem-loop" 1998, *J. Gen. Virol.*, 79:1121-31.

Ying et al. "Inhibition of the replication of the DNA polymerase M550V mutation variant of human hepatitis B virus by adefovir, tenofovir, L-FMAU, DAPD, penciclovir and lobucavir" 2000, *J. Viral Hepat.*, 7(2):161-5.

Ying et al. "Lamivudine, adefovir and tenofovir exhibit long-lasting anti-hepatitis B virus activity in cell culture" 2000, *J. Viral Hepat.*, 7(1):79-83.

Zhu et al. "Anti-Hepatitis B virus activity and metabolism of 2',3'-didehydro-2',-3'-didehydro—β-L(-)-5-fluorocytidine" 1998, *Antimicrob. Agents Chemother*, 42:1805-10.

Zurawski et al. "Definition and spatial location of mouse interleukin-2 residues that interact with its heterotrimeric receptor" 1993, *EMBO J.*, 12(13):5113-19.

Preisler-Adams et al., Jun. 24, 1993: "Sequence analysis of hepatitis B virus DNA in immunologically negative infection" Arch. Virol., vol. 133, 1993, pp. 385-396, XP000672310.

Farrell, Clinical Potential of Emerging New Agents in Hepatitis B, 2000, Drugs, vol. 60, No. 4, pp. 701-710.

Database Uniprot [Online] EBI Hinxton U.K.; Nov. 1, 1996, Preisler-Adams et al.: "DNA Polymerase (fragment)" XP-002455528; http://beta.uniprot.org/uniprot(Q67907.txt?version=1).

Gaillard et al., "Kinetic analysis of wild-type and YMDD mutant hepatitis B virus polymerases and effects of deoxyribonucleotide concentrations on polymerase activity," Antimicrob Agents Chemother. 46(4): 1005-1013, 2002.

Colonno et al., "Long-term entecavir treatment results in sustained antiviral efficacy and prolonged life span in the woodchuck model of chronic hepatitis infection," JID 184: 1236-45 2001.

Das et al., "Molecular Modeling and Biochemical Characterization Reveal the Mechanism of Hepatitis B Virus Polymerase Resistance to Lamivudine (3TC) and Emtricitabine (FTC)", J. Virol. 75(10): 4771-4779, 2001.

Delaney et al., "Cross-resistance testing of antihepadnaviral compounds using novel recombinant baculoviruses which encode drug-resistant strains of hepatitis B virus," Antimicrobial Agents Chemother 45(6): 1705-1713, 2001.

Ren and Nassal, "Hepatitis B virus (HBV) virion and covalently closed circular DNA formation in primary tupaia hepatocytes and human hepatoma cell lines upon HBV genome transduction with replication-defective adenovirus vectors," J. Virol. 75(3): 1104-1116, 2001.

Stuyver et al., "Nomenclature for antiviral-resistant human hepatitis B virus mutations in the polymerase region," Hepatology 33: 751-757, 2001.

Yamanaka et al., "Metabolic studies on BMS-200475, a new antiviral compound active against hepatitis B virus," Antimicrobial Agent Chem 43: 190-193, 1999.

Allen et al., "Identification and characterization of mutations in hepatitis B virus resistant to lamivudine. Lamivudine Clinical Investigation Group," Hepatology 27(6): 1670-1677, 1998.

Genovesi et al., "Efficacy of the carbocyclic 2'-deoxyguanosine nucleoside BMS-200475 in the woodchuck model of hepatitis B virus infection," Antimicrobial Agent Chem 42: 3209-3217, 1998.

Seifer et al., "In Vitro Inhibition of Hepadnavirus Polymerases by the Triphosphates of BMS-200475 and Lobucavir," Antimicrobial Agent Chem 28; 3200-3208, 1998.

Xiong et al., "Mutations in hepatitis B DNA polymerase associated with resistance to lamivudine do not confer resistance to adefovir in vitro," Hepatology. 28(6): 1669-73, 1998.

Aye et al., "Hepatitis B virus polymerase mutations during antiviral therapy in a patient following liver transplantation," J Hepatol. 26: 1148-53, 1997.

Bartholomeusz et al., "Clinical experience with famciclovir against hepatitis B virus," Intervirology 40(5-6): 337-342 1997.

Bisacchi et al., "BMS-200475, a novel carbocyclic 2'-deoxyguanosine analog with potent and selective anti-hepatitis B virus activity in vitro," Bioorg. Med. Chem. Lit. 7: 127-132, 1997.

Innaimo et al., "Identification of BMS-200475 as a potent and selective inhibitor of hepatitis B virus," Antimicrobial Agent Chem 44: 1444-1448, 1997.

Main et al., "Double blind, placebo-controlled study to assess the effect of famciclovir on virus replication in patients with chronic hepatitis B virus infection," J. Viral Hepatitis 3: 211-215, 1996.

Dienstag et al., "A preliminary trial of lamivudine for chronic hepatitis B infection," New England J Med 333: 1657-1661, 1995.

Hendricks DA, et al., "Quantitation of HBV DNA in human serum using a branched DNA (bDNA) signal amplification assay," Am J Clin Pathol 104: 537-46, 1995.

Severini et al., "Mechanism of inhibition of duck hepatitis B virus polymerase by (-)- beta-L-2',3'-dideoxy-3'-thiacytidine," Antimicrobial Agents Chemother 39: 1430-1435, 1995.

Kruger et al., "Famciclovir treatment of hepatitis B recurrence after orthotopic liver transplantation—a pilot study [Abstract]," Hepatology 22: 219A, 1994.

Norder et al., "Genetic relatedness of hepatitis B viral strains of diverse geographical origin and natural variations in the primary structure of the surface antigen," (J. Gen. Virol. 74: 1341-1348, 1993.

Vere Hodge, "Famciclovir and penciclovir. The mode of action of famciclovir including its conversion to peciclovir," Antiviral Chem Chemother 4: 67-84, 1993.

Boyd et al., "Antiherpesvirus activity of 9-(4-hydroxy-3-hydroxymethylbut-1-yl) guanine (BRL 39123) in animals," Antiviral Chem Chemother. 32: 358-363, 1987.

Summers and Mason, "Replication of the genome of a hepatitis B-like virus by reverse transcription of an RNA intermediate," Cell 29: 403-415, 1982.

HBV Genebank Accession No. M38454, Mar. 6, 1995.

Ono et al., 2001, The polymerase L528M mutation cooperates with nucleotide binding-site mutations, increasing hepatitis B virus replication and drug resistance, J. Clin. Invest 107(4):449-55.

Xiong et al., 2000, In vitro evaluation of hepatitis B virus polymerase mutations associated with famciclovir resistance, Hepatology 31(1): 219-224.

Ono-Nita et al., 1999, YMDD motif in hepatitis B virus DNA polymerase influences on replication and lamivudine resistance: A study by in vitro full-length viral DNA transfection, Hepatology 29(3):939-45.

Cane et al., 1999, Analysis of hepatitis B virus quasispecies changes during emergence and reversion of lamivudine resistance in liver transplantation, Antiviral Therapy 4:7-14.

Oon et al., 1999, Hepatitis B virus variants with lamivudine-related mutations in the DNA polymerase and the 'A' epitope of the surface antigen are sensitive to ganciclovir, Antiviral Research 41:113-8.

Delaney et al., 1998, Hepatitis B virus replication in human HepG2 cells mediated by hepatitis B virus recombinant baculovirus, Hepatology 28(4):1134-46.

Kruger et al. Famciclovir treatment of hepatitis B recurrence after orthotopic liver transplantation—a pilot study (Abstract), Hepatology 22:219A, 1995.

Villeneuve et al. "Selection of a hepatitis B virus strain resistant to adefovir in a liver transplantation patient" 2003, *J. Hepa.*, 39(6):1085-9.

Wrobel et al. "A genetic approach for identifying critical residues in the fingers and palm subdomains of HIV-1 reverse transcriptase" 1998, *Proc. Natl. Acad. Sci. USA*, 95(2):638-45.

Wulfing et al. "An *Escherichia coli* protein consisting of a domain homologous to FK506-binding proteins (FKBP) and a new metal binding motif" 1994, *Biol. Chem.*, 269(4):2895-901.

Xiong et al. "Origin and evolution of retroelements based upon their reverse transcriptase sequences" *EMBO J.*, 9(10):3353-62, 1990.

Xiong et al. "Resistance surveillance of HBeAg-chronic hepatitis B patients treated for 2 years with adefovir dipivoxi" 2003, *J. Hepatol.*, 38:182.

Xiong et al. "Mutations in hepatitis B DNA polymerase associated with resistance to lamivudine do not confer resistance to adefovir in vitro" 1998, *Hepatol.* 28(6):1669-73.

Xiong et al. "In vitro evaluation of hepatitis B virus polymerase mutations associated with famciclovir resistance" 2000, *Hepatol.*, 31(1):219-24.

Yamaguchi et al. 1986, Japan, *J. Bacteriol.*, 41:701-7.

Yamanaka et al. "Metabolic studies on BMS-200475, a new antiviral compound active against hepatitis B virus" 1999, *Antimicrobial Agent Chem.*, 43:190-3.

Yamano et al. "Outer membrane proteins responsible for the penetration of beta-lactams and quinolones in *Pseudomonas aeruginosa*" 1990, *J. Antimicrob. Chemother.* 26:175-84.

Yamano et al. "Ferric iron transport system of *Pseudomonas aeruginosa* PAO1 that functions as the uptake pathway of a novel catechol-substituted cephalosporin, S-9096" 1994, *Appl. Microbiol. Biotechnol.*, 40:892-7.

* cited by examiner

```
TR1 A-E    1                                                                                                           0  [SEQ ID NO:13]
TR2 A-E    1                                                                                                           0  [SEQ ID NO:14]
TR3 A-E    1                                                                                                           0  [SEQ ID NO:15]
TR4 A-E    1                                                                                                           0  [SEQ ID NO:16]
TR5 A-E    1                                                                                                           0  [SEQ ID NO:17]
TR6 F-E    1  GGGGGCCGCAGNCAGATACAAACCTTNGCCAGGAATCCTCCTTCCTGCATCTACCAATGCCAGTCAGGAAGGCAGCCTACCCGCTGTCTCCACCTTTG         100  [SEQ ID NO:18]

TR1 A-E    1                                                                                                           0  [SEQ ID NO:13]
TR2 A-E    1                                                                                                           0  [SEQ ID NO:14]
TR3 A-E    1                                                                                                           0  [SEQ ID NO:15]
TR4 A-E    1                                                                                                           0  [SEQ ID NO:16]
TR5 A-E    1                                                                                                           0  [SEQ ID NO:17]
TR6 F-E  101  AGAGACTCTCATCCTCCTCAGGCCATGCAGTGGAACTCCACAAACTTTCCACCAAACTCTGCAAGATCCCAGGGTGAGGGGCCTGTATCTCCCTGTGGTGGCT       200  [SEQ ID NO:18]

TR1 A-E    1                                                                                                           0  [SEQ ID NO:13]
TR2 A-E    1                                                                                                           0  [SEQ ID NO:14]
TR3 A-E    1                                                                                                           0  [SEQ ID NO:15]
TR4 A-E    1                                                                                                           0  [SEQ ID NO:16]
TR5 A-E    1                                                                                                           0  [SEQ ID NO:17]
TR6 F-E  201  CCAGTTCAGGAACAGTAAACCCTGTTCCGACTACTGCCTCTCCCATATCGTCAATCTTCTGAGGATTGGGACTTGCGCTGAACATGGAGAACATCAC            300  [SEQ ID NO:18]

TR1 A-E    1                                                                                                           0  [SEQ ID NO:13]
TR2 A-E    1                                                                                                           0  [SEQ ID NO:14]
TR3 A-E    1                                                                                                           0  [SEQ ID NO:15]
TR4 A-E    1                                                                                                           0  [SEQ ID NO:16]
TR5 A-E    1                                                                                                           0  [SEQ ID NO:17]
TR6 F-E  301  ATCAGGATTCCTAGGACCCCTGCTCGTGTTACAGGGCGGGGTTTTTCTTGTTGACAAGAATCCTCACAATACCGAGAGTCTCGTGTGGACTTCT              400  [SEQ ID NO:18]

TR1 A-E    1                                                                    CCCTCCGTTCCAACTTGTCCTGGTT              28  [SEQ ID NO:13]
TR2 A-E    1                                                                    CTGTCTCCAACTTGTCCTGGTT                 23  [SEQ ID NO:14]
TR3 A-E    1                                                                    CTGTCTCCAACTTGTCCTGGTT                 23  [SEQ ID NO:15]
TR4 A-E    1                                                                      GTCTCCAACTTGTCCTGGTT                 21  [SEQ ID NO:16]
TR5 A-E    1                                                                      GTTCCAACTTGTCCTGGTT                  21  [SEQ ID NO:17]
TR6 F-E  401  CTCAATTTTCTAGGGGGAACCACCCGTGTCTTGGCCAAAATTCGCAGTCCCCAACCTCCAATCACTCACCAACTTCTGTGGTTCTCAACTTGTCCTGGTT       500  [SEQ ID NO:18]

TR1 A-E   29  ATCGCTGGATGTGTCTGCGGCGGCGTTTATCATATTCCTTCATCTTCTGTGGTTCTGCCTATGCCTGCTGTGCTGTCTTGGACTATCAAGGTATGTTGCC       128  [SEQ ID NO:13]
TR2 A-E   24  ATCGCTGGATGTGTCTGCGGCGGCGTTTTATCATATTCCTTCATCTTCTGTGGTTCTGCCTATGCCTGCTGTGCTGTCTTGGACTATCAAGGTATGTTGCC      123  [SEQ ID NO:14]
TR3 A-E   24  ATCGCTGGATGTGTCTGCGGCGGCGTTTTATCATATTCCTTCATCTTCTGTGGTTCTGCCTATGCCTGCTGTGCTGTCTTGGACTATCAAGGTATGTTGCC      123  [SEQ ID NO:15]
TR4 A-E   22  ATCGCTGGATGTGTCTGCGGCGGCGTTTTATCATATTCCTTCATCTTCTGTGGTTCTGCCTATGCCTGCTGTGCTGTCTTGGACTATCAAGGTATGTTGCC      121  [SEQ ID NO:16]
TR5 A-E   22  ATCGCTGGATGTGTCTGCGGCGGCGTTTTATCATATTCCTTCATCTTCTGTGGTTCTGCCTATGCCTGCTGTGCTGTCTTGGACTATCAAGGTATGTTGCC      121  [SEQ ID NO:17]
TR6 F-E  501  ATCGCTGGATGTGTCTGCGGCGGCGTTTTATCATATTCCTTCATCTTCTGTGGTTCTGCCTATGCCTGCTGTGCTGTCTTGGACTATCAAGGTATGTTGCC      600  [SEQ ID NO:18]
```

```
Pol Trans of TR1    1                                                                                                             0  [SEQ ID NO:19]
Pol Trans of TR2    1                                                                                                             0  [SEQ ID NO:20]
Pol Trans of TR3    1                                                                                                             0  [SEQ ID NO:21]
Pol Trans of TR4    1                                                                                                             0  [SEQ ID NO:22]
Pol Trans of TR5    1                                                                                                             0  [SEQ ID NO:23]
Pol Trans of TR6    1  IYQSPVRKAAYPAVSTFERLSSSGHAVELHHNFFPNSARSQGEGPVSPCHWLQFRNGKPCSDYCLSHIVNLLEDWGPCAEHGENH                       86 [SEQ ID NO:24]

Pol Trans of TR1    1                           SNLSWLSLDVSAAFYHIPLHPAAMPHLLVGSSGLSRYVA                                          39 [SEQ ID NO:19]
Pol Trans of TR2    1                           LSSNLSWLSLDVSAAFYHIPLHPAAMPHLLVGSSGLSRYVA                                        41 [SEQ ID NO:20]
Pol Trans of TR3    1                           LSSNLSWLSLDVSAAFYHIPLHPAAMPHLLVGSSGLSRYVA                                        41 [SEQ ID NO:21]
Pol Trans of TR4    1                           SSNLSWLSLDVSAAFYHIPLHPAAMPHLLVGSSGLSRYVA                                         40 [SEQ ID NO:22]
Pol Trans of TR5    1                           SSNLSWLSLDVSAAFYHIPLHPAXMPHLLVGSSGLSRYVA                                         40 [SEQ ID NO:23]
Pol Trans of TR6   87  IRIPRTPARVTGGVFIVDKNPHHTAESRLVVDFSQFSRGNHRVSWPKFAVPNLQSLTNLLSNLSWLSLDVSAAFYHIPLHPAXMPHLLVGSSGLSRYVA      187 [SEQ ID NO:24]

Pol Trans of TR1   40  RLSSNSRIFNHQRGTMQNLHDYCSRNLYVSLLLLYQTFGRKLHLYSHPIILGFRKIPNGVGLSPFLMAQFTSAICSVVRRAFPHCLAFSYXDDVVLGAKS     139 [SEQ ID NO:19]
Pol Trans of TR2   42  RLSSNSRIFNHQRGTMQNLHDYCSRNLYVSLLLLYQTFGRKIHLYSHPIILGFRKIPMGVGLSPPLMAQFTSAICSVVRRAFPHCLAFSYVDDVVLGAKS     141 [SEQ ID NO:20]
Pol Trans of TR3   42  RLSSNSRIFNHQRGTMQNLHDYCSRNLYVSLLLLYQTFGRKLHLYSHPIILGFRKIPMGVGLSPFLMAQFTSAICSVVRRAFPHCLAFSYVDDVVLGAKS     141 [SEQ ID NO:21]
Pol Trans of TR4   41  RLSSNSRIFNHQRGTMQNLHDYCSRNLYVSLLLLYQTFGRKLHLYSHPITLGFRKIPMGVGLSPFLMAQFTSAICSVVRRAFPHCLAFSYVDDVVLGAKS     140 [SEQ ID NO:22]
Pol Trans of TR5   41  RLSSNSRIFNHQRGTMQNLHDYCSRNLYVSLLLLYQTFGRKIHLYSHPIILGFRKIPMGXGLSPFLMAQFTSAICSVVRRAFPHCLAFSYVDUVVLGAKS     140 [SEQ ID NO:23]
Pol Trans of TR6  188  RLSSNSRIFNHQRGTMQNLHDYCSRNLYVSLLLLYQTFGRKLHLYSHPIIIGFRKTPMGLGLSPFLMAQFTSAICSVVRRDAFPHCLAFSYVDDVVLGAKS     288 [SEQ ID NO:24]

Pol Trans of TR1  140  VQHLESLFTAVTNFLLSLGIHLNPNKTKRWGYSLNFMGYVIG                                                             181 [SEQ ID NO:19]
Pol Trans of TR2  142  VQHLESLFTAVTNFLLSLGIHLNPNKTKRWGYSLNFMGVVIGCYGS                                                         187 [SEQ ID NO:20]
Pol Trans of TR3  142  VQHLESLFTAVTNFLLSLCIHLNPNKTKRWGYSLNFMGYVIGCY                                                           185 [SEQ ID NO:21]
Pol Trans of TR4  141  VQHLESLFTAVTNFLLSLGIHINPNKTKRWGYSLNFMGYVIGCY                                                           184 [SEQ ID NO:22]
Pol Trans of TR5  141  VQHLESLFTAVTNFLLSLGIHLHLNPNKTKRWGYSLNFMGYVIGCY                                                         184 [SEQ ID NO:23]
Pol Trans of TR6  289  VQHLESLFTAVTNFLLSLGIHLNPNKTKRWGYSLNFUGYVIG                                                             330 [SEQ ID NO:24]
                                                            M→V 250
                                                         M250V mhL
```

Figure 5

```
HBsAg Trans of TR1 1                                                                                              0   [SEQ ID NO:25]
HBsAg Trans of TR2 1                                                                                              0   [SEQ ID NO:26]
HBsAg Trans of TR3 1                                                                                              0   [SEQ ID NO:27]
HBsAg Trans of TR4 1                                                                                              0   [SEQ ID NO:28]
HBsAg Trans of TR5 1                                                                                              0   [SEQ ID NO:29]
HBsAG Trans of TR6 1              STNRQSGRQPTPLSPPLRDSHPQAMQWNSTTFHQTLQDPRVRGLYLPAGGSSSGTVNPVPTTASPISSIFSRIGDLALNMENIT 100   [SEQ ID NO:30[

HBsAg Trans of TR1 1                                                      PTCPGYRWMCLRRFIIFLFILLLCLIFLLVLLDYQGMLP  39   [SEQ ID NO:25]
HBsAg Trans of TR2 1                                                    CPPTCPGYRWMCLRRFIIFLFILLLCLIFLLVLLDYQGMLP  41   [SEQ ID NO:26]
HBsAg Trans of TR3 1                                                    CPPTCPGYRWMCLRRFIIFLFILLLCLIFLLVLLDYQGMLP  41   [SEQ ID NO:27]
HBsAg Trans of TR4 1                                                     PPTCPGYRWMCLRRFIIFLFILLLCLIFLLVLLDYQGMLP  40   [SEQ ID NO:28]
HBsAg Trans of TR5 1                                                     PPTCPGYRWMCLRRFIIFLFILLLCLIFLLVLLDYQGMLP  40   [SEQ ID NO:29]
HBsAG Trans of TR6 1 SGFLGPLLVLQAGFFLLTRILTIPQSLDSWWTSLNFLGGTTVCLGQNSQSPTSNHSPTSCPPTCPGYRWMCLRRFIIFLFILLXCLIFLLVLLDYQGMLP 200   [SEQ ID NO:30]

HBsAg Trans of TR1  40 VCPLIPGSSTTSAGPCRTCTTTAQGTSMYPSCCCTKPSDGNCTCIPIPSSWAFGKFLWEWASARFSWLSLLXPFVQWFVGLSPTVWLLVXWMMWYWGPSL 139 [SEQ ID NO:25]
HBsAg Trans of TR2  42 VCPLIPGSSTTSAGPCRTCTTTAQGTSMYPSCCCTKPSDGNCTCIPIPSSWAFGKFLWEWASARFSWLSLLXPFVQWFVGLSPTVWLSVMWMMWYWGPSL 141 [SEQ ID NO:26]
HBsAg Trans of TR3  42 VCPLIPGSSTTSAGPCRTCTTTAQGTSMYPSCCCTKPSDGNCTCIPIPSSWAFGKFLWEWASARFSWLSLLVPFVQWFVGLSPTVWLXVMWMMWYWGPSL 141 [SEQ ID NO:27]
HBsAg Trans of TR4  41 VCPLIPGSSTTSAGPCRTCTTTAQGTSMYPSCCCTKPSDGNCTCIPIPSSWAFGKFLWEWASARFSWLSLLVPFVQWFVGLSPTVWLSVMWMMWYWGPSL 140 [SEQ ID NO:28]
HBsAg Trans of TR5  41 VCPLIPGSSTTSAGPCRTCTTTAQGTSMYPSCCCTKPSDGNCTCIPIPSSWAFGKFLWXWASARFSWLSLLVPFVQWFVGLSPTVWLSVMWMMWYWGPSL 140 [SEQ ID NO:29]
HBsAG Trans of TR6 201 VCPLIPGSSTTSAGPCRTCTTTAQGTSMYPSCCCTKPSDGNCTCIPIPSSWAFGKLLWDWASARFSWLSLLVPFVQWFVGLSPTVWLSVMWMMWYWGPSL 300 [SEQ ID NO:30]

HBsAg Trans of TR1 140 YSTLSPFLPLLPIFFCLWVYIN            161                                                                  [SEQ ID NO:25]
HBsAg Trans of TR2 142 YSTLSPFLPLLPIFFCLWVYI             162                                                                  [SEQ ID NO:26]
HBsAg Trans of TR3 142 YSTLSPFLPLLPIFFCLWVYI             162                                                                  [SEQ ID NO:27]
HBsAg Trans of TR4 141 YSTLSPFLPLLPIFFCLWVYI             161                                                                  [SEQ ID NO:28]
HBsAg Trans of TR5 141 YSTLSPFLPLLPIFFCLWVYI             161                                                                  [SEQ ID NO:29]
HBsAG Trans of TR6 301 YSTLSPFLPLLPIFFCLWVYI             321                                                                  [SEQ ID NO:30]
```

| | | | |
|---|---|---|---|
| PRE ETV | 1 | TGCCTCATTTTGTGGGTCACCATATATTCTTGGGAACAAGATCTACAGCATGGGGCAGAATCTTTCCACCAGCAATCCTCTGGGATTCTTCCCGACCACCA | 0 [SEQ ID NO:31] |
| ON ETV | 1 | | 100 [SEQ ID NO:32] |
| PRE ETV | 1 | GTTGGGATCCAGCCTTCAGAGAGCAAACACCGGCAAATCCAGATTGGGACTTCAATCCCCAACAAGGACACCTGGCCAGACGCCAACAAGGTAGGAGCTGGAGCA | 0 [SEQ ID NO:31] |
| ON ETV | 101 | | 200 [SEQ ID NO:32] |
| PRE ETV | 1 | TTTCGGGCTGGGTTCACCCCCACCGCACGGAGGCCTTTTGGGGTGGAGCCCTCAGGGCTGAGGGCATACTACAAACTTTGCCAGCAAGCCGGCCTCCTGCCT | 0 [SEQ ID NO:31] |
| ON ETV | 201 | | 300 [SEQ ID NO:32] |
| PRE ETV | 1 | CCACCAATCGCCAGTCAGGAGCGGCAGCCTACCCGCTGTCTCCACCCTTTGAGAGACACTCATCCTCAGGCGCAGTGGAAACCCACCAACCTTCCACCAAAC | 20 [SEQ ID NO:31] |
| ON ETV | 301 | GCCATAACCTTCCACCAAAC | 400 [SEQ ID NO:32] |
| PRE ETV | 21 | TCTGCAAGMTCCCCCTGCTGGTGGCTCGCTGTCCGGAACAGTAAACCCTGTTCCGGAACAGTAAACCCTGTTCCGGAACAGTAAACCCTGTCCCTCCACATATCGTCAATCTTCTGAGGATTGGGGAC | 120 [SEQ ID NO:31] |
| ON ETV | 401 | TGTGCAAGCTCCACCTGCTGGTGGCTCGCTGTCCGGAACAGTAAACCCTGTTCCGGAACAGTAAACCCTGTCCCTCCACATATCGTCAATCTTCTGAGGATTGGGGAC | 500 [SEQ ID NO:32] |
| PRE ETV | 121 | CCTGCGCTGAATATGGAGAACATCAGGATTCCTAGGACCCCTTTCTCGTGTTACAGGCGGGGTTTTTCTTGTTGACAAGAATCCTCACAATACCGM | 220 [SEQ ID NO:31] |
| ON ETV | 501 | CCTGCGCTGAATATGGAGAACATCAGGATTCCTAGGACCCCTCTCGTGTTACAGGCGGGGTTTTTCTTGTTGACAAGAATCCTCACAATACCGA | 600 [SEQ ID NO:32] |
| PRE ETV | 221 | AGAGTCTAGACTCGTGGTGGACTTGACCTGGTTATCGTCCTGATGTGTCTGCGCGTTTATCATATTCCTCTTCATCCTGCCTATGCCTCATCTTCTTGTGTT | 320 [SEQ ID NO:31] |
| ON ETV | 601 | AGAGTCTAGACTCGGTGGTGGACTTGACCTGGTTATCGTCCTGATGTGTCTGCGCGTTTATCATATTCCTCTTCATCCTGCCTATGCCTCATCTTCTTGTGTT | 700 [SEQ ID NO:32] |
| PRE ETV | 321 | CTTCCTGTCCTCCGACTTGTCCTGGTTATCGTCCGACTTGTCCTGGTTATGCCCGGTTTGTCCTCTAATTCCAGGATCCTCAACACCAGCACGGGAACATGCGAACTTGCACGACTCCTGCTCAAG | 420 [SEQ ID NO:31] |
| ON ETV | 701 | CTCCTGTCCTCCGACTTGTCCTGGTTATGCCCGGTTTGTCCTCTAATTCCAGGATCCTCAACACCAGCACGGGAACATGCGAACTTGCACGACTCCTGCTCAAG | 800 [SEQ ID NO:32] |
| PRE ETV | 421 | CTTTCTGGACTATCAAGGTATGTTGCCCTGTTGCTCTGTTACCCTCCTGTTGCTGTACCAAAACCTTGTTGTTCAGTGCCATTGTTCAGTGGTTCGTAGGGCTTTGTCAGTGCCAGTGACCTAAG | 520 [SEQ ID NO:31] |
| ON ETV | 801 | CTTCTGGACTATCAAGGTATGTTGCCCTGTTGCTGTACCAAAACCTTGTTGTTCAGTGCCATTGTTCAGTGGTTCGTAGGGCTTTGTCAGTGCCAGTGACCTATG | 900 [SEQ ID NO:32] |
| PRE ETV | 521 | GAACCTCTATGTATCCCTCCTGTTGCTGTACCAAAACCTTGTTGTTCAGTGCCATTGTTCAGTGGTTCGTAGGGCTTTGTTGGCTTTCAGTGTTTGGCTTTTCAGTTCATTATGTGG | 620 [SEQ ID NO:31] |
| ON ETV | 901 | GAACCTCTATGTATCCCTCCTGTTGCTGTACCAAAACCTTGTTGTTCAGTGCCATTGTTCAGTGGTTCGTAGGGCTTTGTTGGCTTTCAGTGTTTGGCTTTTCATTTATGTGG | 1000 [SEQ ID NO:32] |
| PRE ETV | 621 | GGAGTGGGCCTCAGCCGTTTCTCAGCCCCCGTTTCTCATGGCCTCAGTTTAGTAGTGCCAGTTTGGTAGTGCCAGTTTGGCCATTGTTGGCCATTGGGTATACATTGAACCCTAA | 720 [SEQ ID NO:31] |
| ON ETV | 1001 | GGAGTGGGCCTCAGCCGTTTCTCATGGCCTCAGTTTGGTAGTGCCAGTTTGGCCATTGTTGGCCATTGGGTATACATTGAACCCTAA | [SEQ ID NO:32] |
| PRE ETV | 721 | ATGATGGTATTGGGGGCCAAGTCTGTACAGCATCTTGAGTCCCTTTACCGCTGTTACCGCTGTTACCGCTGTTACCTTTGCTGTAGAGTCCCTTTACCGCTGTTACCAATTTTCTTTTGTTTCTTGTCTGGGTATACATTGAACCCTAA | 820 [SEQ ID NO:31] |
| ON ETV | 1101 | ATGATGGTATTGGGGGCCAAGTCTGTACAGCATCTTGAGTCCCTTTACCGCTGTTACCGCTGTTACCAATTTTCTTTTGTTTCTTGTCTGGGTATACATTGAACCCTAA | 1200 [SEQ ID NO:32] |
| PRE ETV | 821 | CAAAACAAAGAGATGGGGTTACCCCCTAAATTTTATGGG-CTATGTCATTGGATGATGTTAATGGGTCCTTGCCACACACATCGTACATAAAATCAAGA | 919 [SEQ ID NO:31] |
| ON ETV | 1201 | CAAAACAAAGAGATGGGGTTACTCCCTAAATTTTATGGGCTATG | 1245 [SEQ ID NO:32] |
| PRE ETV | 920 | ATGTTTTAGAAAACTTCCTGTTAACA | 945 [SEQ ID NO:31] |
| ON ETV | 1246 | | 1245 [SEQ ID NO:32] |

Figure 8

```
Pre ETV      1 TFHQTLQXPPAGGSSSGTVNPVPTTASHISSIFSRIGDPALNMENITSGFLGPLLVLQAGFFLLTRILTIPXSLDSWWTSLNFLGGTTVCLGQNSQSPTS 100   [SEQ ID NO:35]
post ETV     1                                           MENITSGFLGPLLVLQAGFFLLTRILTIPKSLDSWWTSLNFLGGTTVCLGQNSQSPTS  58   [SEQ ID NO:36]

Pre ETV    101 NHSPTSCPPT*                                                                                          110   [SEQ ID NO:35]
post ETV    59 NHSPTSCPPTCPGYRWMCLRRFIIFLFILLLCLIFLLVLLDYQGMLPVCPLIPGSSTTSTGTCRTCTTPAQGTSMYPSCCCTKPSDGNCTCIPIPSSWAF 158   [SEQ ID NO:36]

Pre ETV    110                                                                        110                            [SEQ ID NO:35]
post ETV   159 GKFLWEWASARFSWLSLVVPFVQWFVGLSPTVWLSFMWMMWYWGPSLYSILSPFLPLLPIFFCLWVYI   226                            [SEQ ID NO:36]
```

VIRAL VARIANTS WITH ALTERED SUSCEPTIBILITY TO NUCLEOSIDE ANALOGS AND USES THEREOF

CROSS REFERENCE TO RELATED APPLICATIONS

The present application is a continuation of U.S. patent application Ser. No. 10/911,464 filed Aug. 4, 2004, which issued on Jul. 29, 2008, as U.S. Pat. No. 7,405,039 which is a continuation of International Patent Application No. PCT/AU03/00111, filed Feb. 5, 2003, published in English on Aug. 14, 2003 as International Patent Publication No. WO03/066841, which claims priority to Australia Patent Application Nos. PS0370/02, filed Feb. 7, 2002 and PS1269/02, filed Mar. 21, 2002, all of which are incorporated by reference herein in their entireties and to each of which priority is claimed.

BACKGROUND OF THE INVENTION

The present invention relates generally to viral variants exhibiting reduced sensitivity to particular agents and/or reduced interactivity with immunological reagents. More particularly, the present invention is directed to hepatitis B virus (HBV) variants exhibiting complete or partial resistance to nucleoside analogs and/or reduced interactivity with antibodies to viral surface components including reduced sensitivity to these antibodies. The present invention further contemplates assays for detecting such viral variants, which assays are useful in monitoring anti-viral therapeutic regimens and in developing new or modified vaccines directed against viral agents and in particular HBV variants. The present invention also contemplates the use of the viral variants to screen for agents capable of inhibiting infection, replication and/or release of the virus.

Bibliographic details of the publications referred to by author in this specification are collected at the end of the description.

The reference to any prior art in this specification is not, and should not be taken as, an acknowledgment or any form of suggestion that that prior art forms part of the common general knowledge in any country.

Specific mutations in an amino acid sequence are represented herein as 'Xaa$_1$nXaa$_2$' where Xaa$_1$ is the original amino acid residue before mutation, n is the residue number and Xaa$_2$ is the mutant amino acid. The abbreviation 'Xaa' may be the three letter or single letter (i.e. 'X') code. The amino acid residues for Hepatitis B virus DNA polymerase are numbered with the residue methionine in the motif Tyr Met Asp Asp (YMDD) being residue number 204 (Stuyver et al., *Hepatology* 33: 751-757, 2001). The amino acid residues for hepatitis B virus surface antigen are number according to Norder et al. (*J. Gen. Virol.* 74: 341-1348, 1993).

The term nucleoside analogs has been used in reference to both nucleotide and nucleoside analogs.

Hepatitis B virus (HBV) can cause debilitating disease conditions and can lead to acute liver failure. HBV is a DNA virus which replicates via an RNA intermediate and utilizes reverse transcription in its replication strategy (Summers and Mason, *Cell* 29: 403-415, 1982). The HBV genome is of a complex nature having a partially double-stranded DNA structure with overlapping open reading frames encoding surface, core, polymerase and X genes. The complex nature of the HBV genome is represented in FIG. 1. The polymerase consists of four functional regions, the terminal protein (TP), spacer, reverse transcriptase (rt) and ribonuclease (RNAse).

The polymerase gene of HBV overlaps the envelope gene, mutations in the catalytic domain of the polymerase can affect the amino acid sequence of the envelope protein and vice versa. In particular, the genetic sequence for the neutralization domain of HBV known as the 'a' determinant, which is found within the HBsAg and located between amino acids 99 and 169, actually overlaps the major catalytic regions of the viral polymerase protein and in particular domains A and B.

The presence of an HBV DNA polymerase has led to the proposition that nucleoside analogs could act as effective anti-viral agents. Examples of nucleoside analogs currently being tested are penciclovir and its oral form (FAM) [Vere Hodge, *Antiviral Chem Chemother* 4: 67-84, 1993; Boyd et al., *Antiviral Chem. Chemother.* 32: 358-363, 1987; Kruger et al, *Hepatology* 22: 219A, 1994; Main et al., *J. Viral Hepatitis* 3: 211-215, 1996] Lamivudine[(−)-β-2'-deoxy-3'-thiacytidine; (3TC or LMV) [Severini et al, *Antimicrobial Agents Chemother* 39: 1430-1435, 1995; Dienstag et al., *New England J Med* 333: 1657-1661, 1995]. New nucleoside analogs which have already progressed to clinical trials include the pyriamidines Emtricitabine, ((−)-β-L-2'-3'-dideoxy-5-fluoro-3'-thiacydidine; FTC), the 5-fluoro derivative of 3TC, and Clevudine (1-(2-fluoro-5-methyl-β-L-arabino-furanosyl) uracil; L-FMAU), a thymidine analog. Like 3TC, these are pyrimidine derivatives with an unnatural "L"-configuration. Several purine derivatives have also progressed to clinical trials; they include Entecavir (BMS-200,475; ETV), a carbocyclic deoxyguanosine analog, diaminopurine dioxolane (DAPD), an oral pro-drug for dioxolane guanine ((−)-β-D-2-aminopurine dioxolane; DXG) and Adefovir dipivoxil, an oral prodrug for the acyclic deoxyadenosine monophosphate nucleoside analog Adefovir (9-[phosphonyl-methoxyethyl]-adenine; PMEA).

While these agents are highly effective in inhibiting HBV DNA synthesis, there is the potential for resistant mutants of HBV to emerge during long term antiviral chemotherapy. In patients on prolonged lamivudine (LMV) therapy key resistance mutations are selected in the rt domain within the polymerase at rtM204I/V+/−rtL180M. The nomenclature used for the polymerase mutations is in accordance with that proposed by Stuyver et al., 2001, supra. Only LMV has been approved for use against chronic HBV infection. LMV is a particularly potent inhibitor of HBV replication and reduces HBV DNA titres in the sera of chronically infected patients after orthotopic liver transplantation (OLT) by inhibiting viral DNA synthesis. LMV monotherapy seems unlikely to be able to control HBV replication in the longer term. This is because emergence of LMV-resistant strains of HBV seems almost inevitable during monotherapy and single therapy is generally inadequate to result in viral clearance per se.

Entecavir (ETV) is also a potent inhibitor of HBV replication. ETV is an orally available cyclopentyl deoxyguanosine analog with activity against hepadnaviruses and herpesviruses. Preclinical studies indicate that ETV is a highly potent inhibitor of HBV in enzyme- and cell-based assays (Innaimo et al., *Antimicrobiol Agent Chem* 44: 1441-1448, 1997; Siefer et al., *Antimicrobiol Agent Chem* 28; 3200-3208, 1998; Yamanaka et al., *Antimicrobiol Agent Chem* 43: 190-193, 1999). ETV has also demonstrated efficacy against WHV in chronically-infected woodchucks (Colonno et al., *JID* 184: 1236-45 2001; Genovesi et al., *Antimicrobiol Agent Chem* 42: 3209-3217, 1998). A four week dose-escalation trial indicated that ETV was well-tolerated and resulted in a 2.5 log$_{10}$ mean reduction in viremia at the highest dose tested (1 mg/daily). LMV resistance mutations were reported to confer cross-resistance to ETV in vitro, although entecavir was still capable of inhibiting viral replication at higher doses; these data are somewhat surprising considering that ETV is not an L-nucleoside. ETV has been used successfully to treat patients with the LMV resistant HBV mutations. No specific ETV resistant mutations had been described.

Nucleoside analog therapy may be administered as monotherapy or combination therapy where two or more nucleoside analogs may be administered. The nucleoside analogs may also be administered in combination with other antiviral agents such as interferon or hepatitis B immunoglobulin (HBIG).

There is a need to identify nucleoside- and/or antibody-resistant variants of HBV. The rapid identification can lead to altered therapeutic protocols being pursued.

SUMMARY OF THE INVENTION

The present invention relates generally to viral variants exhibiting reduced sensitivity to particular agents and/or reduced interactivity with immunological reagents. More particularly, the present invention is directed to hepatitis B virus (HBV) variants exhibiting complete or partial resistance to nucleoside analogs and/or reduced interactivity with antibodies to viral surface components including reduced sensitivity to these antibodies. The present invention further contemplates assays for detecting such viral variants, which assays are useful in monitoring anti-viral therapeutic regimens and in developing new or modified vaccines directed against viral agents and in particular HBV variants. The present invention also contemplates the use of the viral variants to screen for agents capable of inhibiting infection, replication and/or release of the virus.

BRIEF DESCRIPTION OF THE DRAWINGS

FIG. 4 is a representation showing comparison of the HBV nucleotide sequence encoding the catalytic region of the polymerase gene in sequential samples from Patient A during LMV monotherapy or LMV/entecavir combination therapy.

FIG. 5 is a representation showing comparison of the deduced amino acid sequence of the catalytic region of the polymerase gene in sequential samples from Patient A during LMV monotherapy or LMV/entecavir combination therapy.

FIG. 6 is a representation showing comparison of the deduced amino acid sequence of the envelope gene in sequential samples from Patient A during LMV monotherapy or LMV/entecavir combination therapy.

FIG. 8 is a representation showing comparison of the HBV nucleotide sequence encoding the catalytic region of the polymerase gene in sequential samples from Patient B during LMV monotherapy (prior to ETV) and on ETV therapy.

FIG. 10 is a representation showing comparison of the deduced amino acid sequence of the envelope gene in sequential samples from Patient B during LMV monotherapy (prior to ETV) and on ETV therapy.

DETAILED DESCRIPTION OF THE INVENTION

Figure 1:
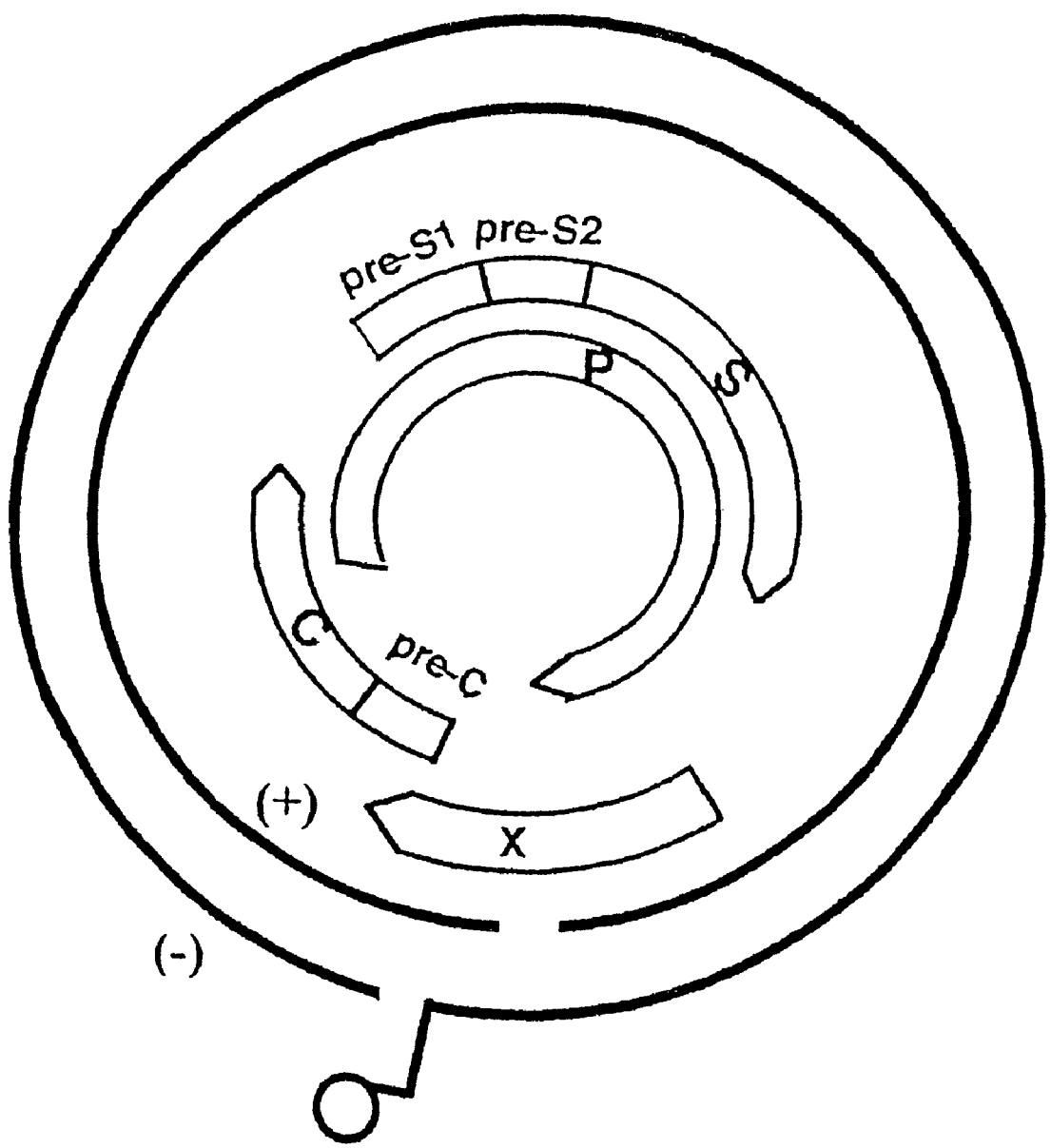
FIG. 1 is a diagrammatic representation showing the partially double stranded DNA HBV genome showing the overlapping open reading frames encoding surface (S), core (C), polymerase (P) and X gene.

The abbreviations defined in Table 1 are used in the present specification.

TABLE 1

Abbreviations

| ABBREVIATION | DESCRIPTION |
| --- | --- |
| 3TC | (LMV); (−)-β-2′-deoxy-3′-thiacytidine |
| ADV | adefovir |
| DAPD | diaminopurine dioxolane |
| DXG | dioxolane guanine |
| ETV | entecavir |
| FAM | famciclovir |
| FTC | emtricitabine |
| HBIG | hepatitis B immunoglobulin |
| HBsAg | hepatitis B surface antigen |
| HBV | hepatitis B virus |
| LMV | lamividuine |
| PMEA | adefovir |
| RNAse | ribonuclease |
| rt | reverse transcriptase |
| YMDD | Tyr Met Asp Asp-a motif in the polymerase protein; where the Met residue is designated residue number 204 of the reverse transcriptase |

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The use of the term "a" or "an" should be understood to include "at least one" or "one or more."

Nucleotide and amino acid sequences are referred to by a sequence identifier number (SEQ ID NO:). The SEQ ID NOs: correspond numerically to the sequence identifiers <400>1, <400>2, etc. A sequence listing is provided after the claims.

The positions of nucleotide and amino acid mutations identified using nomenclature from genotypes B, C or F where the methionine residue in the YMDD motif of the DNA polymerase was designated position 550 (see Australian Patent No. 734831). The nucleotide and amino acid positions given in the present specification are based on a new nomenclature where the methionine residue is YMDD is position 204 and is referred to as rtM204 where rt is an abbreviation for "reverse transcriptase".

In accordance with the present invention, HBV resistant variants were identified in a patient (patient A) with chronic hepatitis B treated with both LMV and ETV and a liver transplant patient (patient B) treated with ETV that had been previously treated with a number of nucleoside agents including LMV. In combination therapy, accordance with the present invention, resistant variants of HBV were identified, following LMV and ETV treatment, with mutations in the HBV DNA polymerase gene which reduce the sensitivity of HBV to these nucleoside analogs. Corresponding mutations in the surface antigen also occur. The identification of these HBV variants is important for the development of assays to monitor LMV and/or ETV resistance and/or resistance to other nucleoside analog therapeutic regimes and to screen for agents which are useful as alternative therapeutic agents. The mutations detected in the HBV isolated from patient A in key functional domains namely the rtI169T+rtV173L+rtL180M+ rtM204V is demonstrated to have reduced sensitivity to ETV in functional assays.

The detection of such HBV variants is particularly important in the management of therapeutic protocols including the selection of appropriate agents for treating HBV infection. The method of this aspect of the present invention is predicated in part on monitoring the development in a subject of an increased HBV load in the presence of a nucleoside analog. The clinician is then able to modify an existing treatment protocol or select an appropriate treatment protocol accordingly.

One aspect of the present invention, therefore, is directed to an isolated HBV variant comprising a nucleotide mutation in a gene encoding a DNA polymerase resulting in at least one amino acid addition, substitution and/or deletion to the DNA polymerase and which exhibits decreased sensitivity to ETV and/or LMV and optionally other nucleoside analogs. Preferably, the DNA polymerase exhibits reduced sensitivity to ETV, or and ETV. The variant HBV comprises a mutation in an overlapping open reading frame in its genome in a region defined by one or more of domains F and A through E of HBV DNA polymerase.

The present invention further contemplates a method for determining the potential for an HBV to exhibit reduced sensitivity to ETV and/or LMV or optionally other nucleoside analogs by isolating DNA or corresponding mRNA from the HBV and screening for a mutation in the nucleotide sequence encoding HBV DNA polymerase resulting in at least one amino acid substitution, deletion and/or addition in any one or more of domains F and A through E or a region proximal thereto of the DNA polymerase and associated with resistance or decreased sensitivity to ETV and/or LMV. The presence of such a mutation is an indication of the likelihood of resistance to said entecavir and/or LMV. Preferably, the HBV variant exhibits reduced sensitivity to ETV, or both ETV and LMV.

The present invention also provides a composition comprising a variant HBV resistant to ETV and/or LMV and optionally other nucleoside analogs or an HBV surface antigen from the variant HBV or a recombinant or derivative form thereof or its chemical equivalent and one or more pharmaceutically acceptable carriers and/or diluents. Yet another aspect of the present invention provides a use of the aforementioned composition or a variant HBV comprising a nucleotide mutation in a gene encoding a DNA polymerase resulting in at least one amino acid addition, substitution and/or deletion to the DNA polymerase and a decreased sensitivity to ETV and/or LMV and optionally other nucleoside analogs in the manufacture of a medicament for the treatment and/or prophylaxis of hepatitis B virus infection.

The present invention also contemplates a method for determining whether an HBV strain exhibits reduced sensitivity to a nucleoside analog by isolating DNA or corresponding mRNA from the HBV and screening for a mutation in the nucleotide sequence encoding the DNA polymerase wherein the presence of the following mutations in the spacer region and the rt region: spacerL97I, spacerK115R, spacerH116L, spacerL128F, spacerS137G, spacerR139G, spacerF142S, rtY54H, rtL91I, rtA97V, rtY124H, rtH126R, rtS135Y, rtI169T, rtM250V, rtV173L, rtL180M, rtM204V, rtA21S, rtA38E, rtF122L, rtT128N, rtQ130P, rtT184G, rtS202I, rtH248N, rtY252L, combinations thereof or an equivalent one or more other mutation thereof is indicative of a variant which exhibits a decreased sensitivity to ETV and/or LMV and optionally other nucleoside analogs.

The subject method may also be practiced by screening for a mutation in the nucleotide sequence encoding the DNA polymerase wherein the presence of the following mutations in the B or C domain of the rt region: rtI169T, rtV173L, rtL180M, rtT184G, rtS202I, rtM204V, combinations thereof or an equivalent one or more other mutations thereof is indicative of a variant which exhibits a decreased sensitivity to ETV and/or LMV and optionally other nucleoside analogs.

It should be noted that mutants rtV173L, rtL180M and rtM204V correspond to mutants V519L, L526M, M550V and M550V, respectively in Australian Patent No. 734831 (using an earlier nomenclature system).

Still a further methodology comprises screening for a mutation in the nucleotide sequence encoding the envelope genes wherein the presence of the following mutations in the PreS1, PreS2 and S genes (changes in the overlapping reverse transcriptase region are indicated in parenthesis): PreS1N114D, PreS1 T115S, PreS2 F22L, PreS2 V39A, PreS2 P52L, sL89V, sT118A, sF161L (=rtI169T), sE164D (=rtV173L), sI195M (=rtM204V), sI208T, PreS1 E86Q, PreS1 N91K, PreS2 P41H, sQ30K, sP120T, sL176V, sV194F or combinations thereof or an equivalent one or more other mutation thereof is indicative of a variant which exhibits a decreased sensitivity to ETV and/or LMV and optionally other nucleoside analogs.

Preferably, the variants are in isolated form such that they have undergone at least one purification step away from naturally occurring body fluid. Alternatively, the variants may be maintained in isolated body fluid or may be in DNA form. The present invention also contemplates infectious molecular clones comprising the genome or parts thereof from a variant HBV. The detection of HBV or its components in cells, cell lysates, cultured supernatant fluid and bodily fluid may be by any convenient means including any nucleic acid-based detection means, for example, by nucleic acid hybridization techniques or via one or more polymerase chain reactions (PCRs). The term "bodily fluid" includes any fluid derived from the blood, lymph, tissue or organ systems including serum, whole blood, biopsy and biopsy fluid, organ explants and organ suspension such as liver suspensions. The invention further encompasses the use of different assay formats of the nucleic acid-based detection means, including restriction fragment length polymorphism (RFLP), amplified fragment length polymorphism (AFLP), single-strand chain polymorphism (SSCP), amplification and mismatch detection (AMD), interspersed repetitive sequence polymerase chain reaction (IRS-PCR), inverse polymerase chain reaction (iPCR) and reverse transcription polymerase chain reaction (RT-PCR), amongst others. Reverse hybridization is a technique which is particularly useful in identifying specific nucleotides or nucleotide sequences. Other forms of detection include Northern blots, Southern blots, PCR sequencing, antibody procedures such as ELISA, Western blot and immunohistochemistry. A particularly useful assay includes the reagents and components required for immobilized oligonucleotide- or oligopeptide-mediated detection systems.

Another aspect of the present invention is directed to a variant HBV comprising a surface antigen having an amino acid sequence with a single or multiple amino acid substitution, addition and/or deletion or a truncation compared to a surface antigen from a reference or wild type HBV and wherein an antibody generated to the reference or wild type surface antigen exhibits an altered immunological profile relative to said HBV variant. One altered profile includes a reduced capacity for neutralizing the HBV. More particularly, the surface antigen of the variant HBV exhibits an altered immunological profile compared to a pre-treatment HBV where the variant HBV is selected for by a nucleoside analog of the HBV DNA polymerase. The variant HBV of this aspect of the invention may also comprise a nucleotide sequence comprising a single or multiple nucleotide substitution, addition and/or deletion compared to a pre-treatment HBV.

The present invention extends to an isolated HBsAg or a recombinant form thereof or derivative or chemical equivalent thereof corresponding to the variant HBV. Generally, the HBsAg or its recombinant or derivative form or its chemical equivalent comprises an amino acid sequence with a single or multiple amino acid substitution, addition and/or deletion or a truncation compared to an HBsAg from a reference HBV and wherein an antibody directed to a reference HBV exhibits an altered immunological profile to an HBV carrying said variant HBsAg. In one embodiment, the altered immunological profile comprises a reduction in the ability to neutralize the variant HBV.

The present invention is predicated in part on the identification and isolation of variants of HBV that have a plurality of mutations and exhibit two or more characteristics selected from decreased or reduced sensitivity to one or more nucleoside analogs, a reduced level and/or functional activity of hepatitis B e antigen, or a reduced, abrogated or otherwise impaired immunological interactivity, relative to wild-type HBV. Thus, the identification of HBV variants with these mutational patterns is important inter alia for the development of assays to detect HBV variants and assays to screen for agents which are useful in treating and/or preventing infections by those variants and/or other HBV isolates and for the development of alternative therapeutic regimes for managing HBV infections.

Accordingly, one aspect of the present invention is directed to an isolated HBV variant comprising a plurality of nucleotide mutations that correlate with at least two characteristics selected from (a) resistance to one or more nucleoside analogs, (b) a reduced level and/or functional activity of hepatitis B e antigen, or (c) a reduced, abrogated or otherwise impaired immunological interactivity.

Another aspect of the present invention contemplates an isolated HBV variant comprising a plurality of nucleotide mutations that correlate with (a) resistance to one or more nucleoside analogs, (b) a reduced level and/or functional activity of hepatitis B e antigen, and (c) a reduced, abrogated or otherwise impaired immunological interactivity.

Yet another aspect of the present invention provides an isolated HBV variant comprising a plurality of nucleotide mutations selected from two or more of (a) a nucleotide mutation in a gene encoding a DNA polymerase resulting in at least one amino acid addition, substitution and/or deletion to said DNA polymerase wherein said variant exhibits decreased sensitivity to ETV and/or LMV and optionally other nucleoside analogs, (b) a nucleotide mutation in a gene encoding a hepatitis B e antigen or in a transcriptional control element of said gene wherein said mutation results in a reduced level and/or functional activity of said hepatitis B e antigen, or (c) a nucleotide mutation in a gene encoding a hepatitis B polypeptide resulting in at least one amino acid addition, substitution and/or deletion to said polypeptide which reduces, abrogates or otherwise impairs its immunological interactivity.

Another aspect of the present invention contemplates a method for detecting an agent which exhibits inhibitory activity to an HBV by generating a genetic construct comprising a replication competent-effective amount of the genome from the HBV contained in a plasmid vector and then transfecting said cells with said construct, contacting the cells, before, during and/or after transfection, with the agent to be tested, culturing the cells for a time and under conditions sufficient for the HBV to replicate, express genetic sequences and/or assemble and/or release virus or virus-like particles if resistant to said agents; and performing viral- or viral-component-detection means to determine whether or not the virus in the culture has replicated, expressed genetic material and/or assembled and/or been released in the presence of the agent. In a preferred embodiment, the plasmid vector in a baculovirus vector and the method comprises generating a genetic construct comprising a replication competent-effective amount of the genome from the HBV contained in or fused to an amount of a baculovirus genome effective to infect cells and then infecting said cells with said construct, contacting the cells, before, during and/or after infection, with the agent to be tested, culturing the cells for a time and under conditions sufficient for the HBV to replicate, express genetic sequences and/or assemble and/or release virus or virus-like particles if resistant to said agent and performing viral- or viral-component-detection means to determine whether or not the virus in the culture has replicated, expressed genetic material and/or assembled and/or been released in the presence of the agent.

In an alternative embodiment, the method comprises generating a continuous cell line comprising an infectious copy of the genome of the HBV in a replication competent effective amount such that said infectious HBV genome is stably integrated into said continuous cell line such as but not limited to 2.2.15 or AD, contacting the cells with the agent to be tested, culturing the cells for a time and under conditions sufficient for the HBV to replicate, express genetic sequences and/or assemble and/or release virus or virus-like particles if resistant to the agent and performing viral- or viral-component-detection means to determine whether or not the virus in the culture has replicated, expressed genetic material and/or assembled and/or been released in the presence of the agent.

In an alternative embodiment, the present invention also contemplate a method for detecting an agent which exhibits inhibitory activity to an HBV polymerase in an in vitro polymerase assay. The HBV polymerase activity can be examined using established assays (Gaillard et al., *Antimicrob Agents Chemother.* 46(4): 1005-1013, 2002; Xiong et al., *Hepatology.* 28(6): 1669-73, 1998). The HBV polymerase may be a wild-type or reference HBV polymerase or mutant HBV polymerase.

In connection with these methods, the plasmid vector may include genes encoding part or all of other viral vectors such as baculovirus vectors or adenovirus vectors (see Ren and Nassal, *J. Virol.* 75(3): 1104-1116, 2001).

In an embodiment of the invention, the present invention also provides for immunogenic compositions comprising an antigenic component of the HBV variants of the present invention. The immunogenic compositions may be used as vaccines.

The identification of viral variants enables the production of vaccines comprising particular recombinant viral components such as polymerases or envelope genes PreS1, PreS2, S encoding for L, M, S proteins, as well as therapeutic vaccines comprising defective HBV variants. Rational drug design may also be employed to identify or generate therapeutic molecules capable of interacting with a polymerase or envelope genes PreS1, PreS2, S encoding for L, M, S proteins or other component of the HBV. Such drugs may also have diagnostic potential.

A summary of sequence identifiers used throughout the subject specification is provided in Table 2.

TABLE 2

Summary of sequence identifiers

Figure 4:
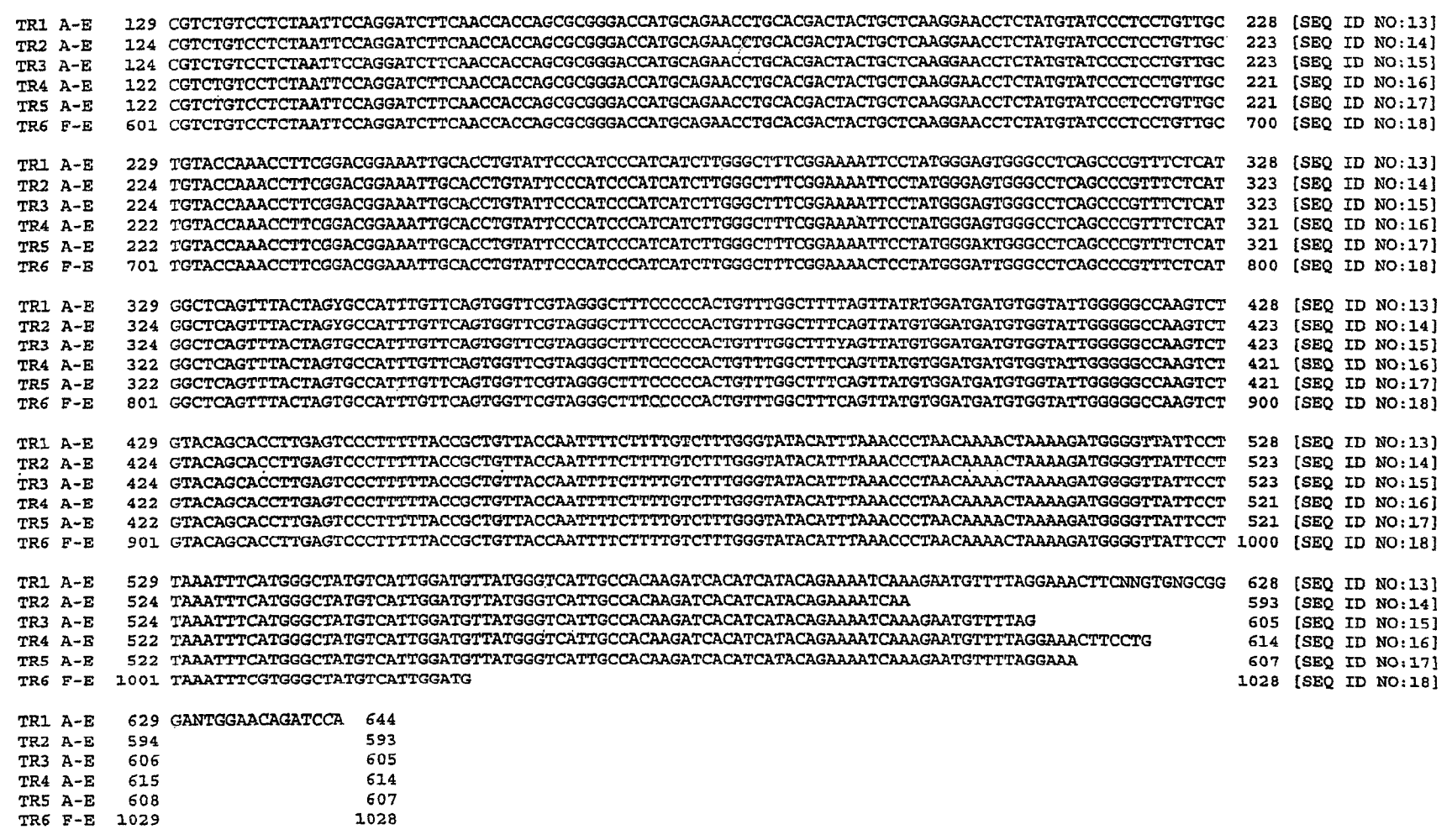

| SEQUENCE ID NO: | DESCRIPTION |
|---|---|
| 1 | region F of HBV DNA polymerase (Formula I) |
| 2 | regions A to E of HBV DNA polymerase (Formula II) |
| 3 | primer (OS1) |
| 4 | primer (TTA3) |
| 5 | primer (JM) |
| 6 | primer (TTA4) |
| 7 | primer (OS2) |
| 8 | primer SEQ2 |
| 9 | primer TTA2 |
| 10 | forward primer PC1 |
| 11 | reverse primer PC2 |
| 12 | HBV-specific molecule beacon primer |
| 13-18 | TR1 (FIG. 4) |
| 19-24 | Pol Trans of TR1 (FIG. 5) |
| 25-30 | HBsAg Trans of TR1 (FIG. 6) |
| 31 | Pre-ETV (FIG. 8) |
| 32 | On-ETV (FIG. 8) |
| 33 | Pre-ETV (FIG. 9) |
| 34 | On-ETV (FIG. 9) |
| 35 | Pre-ETV (FIG. 10) |
| 36 | Post-ETV (FIG. 10) |

The present invention is predicated, in part, on the identification and isolation of nucleoside analog resistant variants of HBV following treatment of patients with ETV or LMV or ETV and LMV and optionally other nucleoside analogs. In particular, ETV, or ETV and LMV treated patients gave rise to variants of HBV exhibiting decreased or reduced sensitivity to ETV and/or LMV. Reference herein to "decreased" or "reduced" in relation to sensitivity to ETV and/or LMV includes and encompasses a complete or substantial resistance to the nucleoside analog as well as partial resistance and includes a replication rate or replication efficiency (yield phenotype), which is more than a wild-type in the presence of a nucleoside analog. In one aspect, this is conveniently measured by an increase in viral load to a level similar or greater than pre-treatment levels.

Accordingly, one aspect of the present invention is directed to an isolated HBV variant, wherein said variant comprises a nucleotide mutation in a gene encoding a DNA polymerase resulting in at least one amino acid addition, substitution and/or deletion to said DNA polymerase, and wherein said variant exhibits decreased sensitivity to ETV and/or LMV and optionally other nucleoside analogs.

Preferably, the decreased sensitivity is in respect of ETV, or both ETV and LMV.

In addition to a mutation in the gene encoding DNA polymerase, due to the overlapping nature of the HBV genome (FIG. 1), a corresponding mutation may also occur in the gene encoding the surface antigen (HBsAg) resulting in reduced interactivity of immunological reagents, such as antibodies and immune cells to HBsAg. The reduction in the interactivity of immunological reagents to a viral surface component generally includes the absence of immunological memory to recognize or substantially recognize the viral surface component. The present invention extends, therefore, to an HBV variant exhibiting decreased sensitivity to ETV and/or LMV and reduced interactivity of an immunological reagent to HBsAg wherein the variant is selected for following ETV and/or LMV combination or sequential treatment. The term "sequential" in this respect means ETV followed by LMV or LMV followed by ETV or multiple sequential administrations of each of ETV and LMV or LMV and ETV.

A viral variant may, therefore, carry mutation only in the DNA polymerase or both in the DNA polymerase and the HBsAg. The term "mutation" is to be read in its broadest context and includes multiple mutations.

The present invention extends to a mutation and any domain of the HBV DNA polymerase and, in particular regions F and A through E, provided said mutation leads to decreased sensitivity to LMV and/or ETV. Region F of the HBV DNA polymerase is defined by the amino acid sequence set forth in Formula I [SEQ ID NO:1] below:

FORMULA I

L, $B_1$, $B_2$, D, W, G, P, C, $B_3$, $B_4$, H, G, $B_5$, H, $B_6$,

I, R, $B_7$, P, R, T, P, $B_8$, R, V, $B_9$, G, G, V, F, L,

V, D, K, N, P, H, N, T, $B_{10}$, E, S, $B_{11}$, L, $B_{12}$, V,

D, F, S, Q, F, S, R, G, $B_{13}$, $B_{14}$, $B_{15}$, V, S, W, P,

K, F, A, V, P, N, L, $B_{16}$, S, L, T, N, L, L, S* wherein:
$B_1$ is L, or R, or I
$B_2$ is E, or D
$B_3$ is T, or D, or A, or N, or Y
$B_4$ is E, or D
$B_5$ is E, or K, or Q
$B_6$ is H, or R, or N,
$B_7$ is I, or T
$B_8$ is A, or S
$B_9$ is T or R
$B_{10}$ is A, or T, or S
$B_{11}$ is R, or T
$B_{12}$ is V, or G
$B_{13}$ is S, or I, or T, or N, or V
$B_{14}$ is T, or S, or H, or Y
$B_{15}$ is R, or H, or K, or Q
$B_{16}$ is Q, or P;
and wherein S* is designated as amino acid 74.

In this specification, reference is particularly made to the conserved regions of the DNA polymerase, as defined by domains A to E. Regions A to E are defined by the amino acid sequence set forth in Formula II [SEQ ID NO:2] below (and in Australian Patent No. 734831):

FORMULA II

S $Z_1$ L S W L S L D V S A A F Y H $Z_2$ P L H P A A M

P H L L $Z_3$ G S S G L $Z_4$ R Y V A R L S S $Z_5$ S $Z_6$ $Z_7$

X N $Z_8$ Q $Z_9$ $Z_{10}$ X X X $Z_{11}$ L H $Z_{12}$ $Z_{13}$ C S R $Z_{14}$ L

Y V S L $Z_{15}$ L L Y $Z_{16}$ T $Z_{17}$ G $Z_{18}$ K L H L $Z_{19}$ $Z_{20}$

H P I $Z_{21}$ L G F R K $Z_{22}$ P M G $Z_{23}$ G L S P F L L A

Q F T S A I $Z_{24}$ $Z_{25}$ $Z_{26}$ $Z_{27}$ $Z_{28}$ R A F $Z_{29}$ H C $Z_{30}$ $Z_{31}$ F $Z_{32}$ Y M* D D $Z_{33}$ V L G A $Z_{34}$ $Z_{35}$ $Z_{36}$ $Z_{37}$ H $Z_{38}$ E $Z_{39}$ L $Z_{40}$ $Z_{41}$ $Z_{42}$ $Z_{43}$ $Z_{44}$ $Z_{45}$ $Z_{46}$ L L $Z_{47}$ $Z_{48}$ G I H L N P $Z_{49}$ K T K R W G Y S L N F M G Y $Z_{50}$ I G wherein:
X is any amino acid;
$Z_1$ is N or D;
$Z_2$ is I or P;
$Z_3$ is I or V;
$Z_4$ is S or D;
$Z_5$ is T or N;
$Z_6$ is R or N;
$Z_7$ is N or I;
$Z_8$ is N or Y or H;
$Z_9$ is H or Y;
$Z_{10}$ is G or R;
$Z_{11}$ is D or N;
$Z_{12}$ is D or N;
$Z_{13}$ is S or Y;
$Z_{14}$ is N or Q;
$Z_{15}$ is L or M;
$Z_{16}$ is K or Q;
$Z_{17}$ is Y or F;
$Z_{18}$ is R or W;
$Z_{19}$ is Y or L;
$Z_{20}$ is S or A;
$Z_{21}$ is I or V;
$Z_{22}$ is I or L;
$Z_{23}$ is V or G;
$Z_{24}$ is C or L;
$Z_{25}$ is A or S;
$Z_{26}$ is V or M;
$Z_{27}$ is V or T;
$Z_{28}$ is R or C;
$Z_{29}$ is F or P;
$Z_{30}$ is L or V;
$Z_{31}$ is A or V;
$Z_{32}$ is S or A;
$Z_{33}$ is V or L or M;
$Z_{34}$ is K or R;
$Z_{35}$ is S or T;
$Z_{36}$ is V or G;
$Z_{37}$ is Q or E;
$Z_{38}$ is L or S or R;
$Z_{39}$ is S or F;
$Z_{40}$ is F or Y;
$Z_{41}$ is T or A;
$Z_{42}$ is A or S;
$Z_{43}$ is V or I;
$Z_{44}$ is T or C;
$Z_{45}$ is N or S;
$Z_{46}$ is F or V;
$Z_{47}$ is S or D;
$Z_{48}$ is L or V;
$Z_{49}$ is N or Q;
$Z_{50}$ is V or I; and
M* is amino acid 204;
and wherein the first S is designated as amino acid 75.

Preferably, the mutation results in an altered amino acid sequence in any one or more of domains F and A through E or regions proximal thereto of the HBV DNA polymerase.

Another aspect of the present invention provides an HBV variant comprising a mutation in an overlapping open reading frame in its genome, wherein said mutation is in a region defined by one or more of domains F and A through E of HBV DNA polymerase, and wherein said variant exhibits decreased sensitivity to ETV and/or LMV and optionally other nucleoside analogs.

In a related embodiment, there is provided an HBV variant comprising a mutation in the nucleotide sequence encoding a DNA polymerase resulting in an amino acid addition, substitution and/or deletion in said DNA polymerase in one or more amino acids as set forth in Formula I [SEQ ID NO:1] and/or II [SEQ ID NO:2]:

FORMULA I
L, $B_1$, $B_2$, D, W, G, P, C, $B_3$, $B_4$, H, G, $B_5$, H, $B_6$,
I, R, $B_7$, P, R, T, P, $B_8$, R, V, $B_9$, G, G, V, F, L,
V, D, K, N, P, H, N, T, $B_{10}$, E, S, $B_{11}$, L, $B_{12}$, V,
D, F, S, Q, F, S, R, G, $B_{13}$, $B_{14}$, $B_{15}$, V, S, W, P,
K, F, A, V, P, N, L, $B_{16}$, S, L, T, N, L, L, S* wherein:
$B_1$ is L, or R, or I
$B_2$ is E, or D
$B_3$ is T, or D, or A, or N, or Y
$B_4$ is E, or D
$B_5$ is E, or K, or Q
$B_7$ is H, or R, or N,
$B_8$ is I, or T
$B_5$ is A, or S
$B_9$ is T or R
$B_{10}$ is A, or T, or S
$B_{11}$ is R, or T
$B_{12}$ is V, or G
$B_{13}$ is S, or I, or T, or N, or V
$B_{14}$ is T, or S, or H, or Y
$B_{15}$ is R, or H, or K, or Q
$B_{16}$ is Q, or P;
and FORMULA II
S $Z_1$ L S W L S L D V S A A F Y H $Z_2$ P L H P A A M
P H L L $Z_3$ G S S G L $Z_4$ R Y V A R L S S $Z_5$ S $Z_6$ $Z_7$
X N $Z_8$ Q $Z_9$ $Z_{10}$ X X X $Z_{11}$ L H $Z_{12}$ $Z_{13}$ C S R $Z_{14}$ L
Y V S L $Z_{15}$ L L Y $Z_{16}$ T $Z_{17}$ G $Z_{18}$ K L H L $Z_{19}$ $Z_{20}$
H P I $Z_{21}$ L G F R K $Z_{22}$ P M G $Z_{23}$ G L S P F L L A
Q F T S A I $Z_{24}$ $Z_{25}$ $Z_{26}$ $Z_{27}$ $Z_{28}$ R A F $Z_{29}$ H C $Z_{30}$
$Z_{31}$ F $Z_{32}$ Y M* D D $Z_{33}$ V L G A $Z_{34}$ $Z_{35}$ $Z_{36}$ $Z_{37}$ H
$Z_{38}$ E $Z_{39}$ L $Z_{40}$ $Z_{41}$ $Z_{42}$ $Z_{43}$ $Z_{44}$ $Z_{45}$ $Z_{46}$ L L $Z_{47}$
$Z_{48}$ G I H L N P $Z_{49}$ K T K R W G Y S L N F M G Y
$Z_{50}$ I G wherein:
X is any amino acid;
$Z_1$ is N or D;
$Z_2$ is I or P;
$Z_3$ is I or V;
$Z_4$ is S or D;
$Z_5$ is T or N;
$Z_6$ is R or N;
$Z_7$ is N or I;
$Z_8$ is N or Y or H;
$Z_9$ is H or Y;
$Z_{10}$ is G or R;
$Z_{11}$ is D or N;
$Z_{12}$ is D or N;
$Z_{13}$ is S or Y;
$Z_{14}$ is N or Q;

$Z_{15}$ is L or M;
$Z_{16}$ is K or Q;
$Z_{17}$ is Y or F;
$Z_{18}$ is R or W;
$Z_{19}$ is Y or L;
$Z_{20}$ is S or A;
$Z_{21}$ is I or V;
$Z_{22}$ is I or L;
$Z_{23}$ is V or G;
$Z_{24}$ is C or L;
$Z_{25}$ is A or S;
$Z_{26}$ is V or M;
$Z_{27}$ is V or T;
$Z_{28}$ is R or C;
$Z_{29}$ is F or P;
$Z_{30}$ is L or V;
$Z_{31}$ is A or V;
$Z_{32}$ is S or A;
$Z_{33}$ is V or L or M;
$Z_{34}$ is K or R;
$Z_{35}$ is S or T;
$Z_{36}$ is V or G;
$Z_{37}$ is Q or E;
$Z_{38}$ is L or S or R;
$Z_{39}$ is S or F;
$Z_{40}$ is F or Y;
$Z_{41}$ is T or A;
$Z_{42}$ is A or S;
$Z_{43}$ is V or I;
$Z_{44}$ is T or C;
$Z_{45}$ is N or S;
$Z_{46}$ is F or V;
$Z_{47}$ is S or D;
$Z_{48}$ is L or V;
$Z_{49}$ is N or Q;
$Z_{50}$ is V or I; and
M* is amino acid 204;
and wherein S* in Formula I is designated as amino acid 74 and the first S in Formula II is designated as amino acid 75; and wherein said variant exhibits decreased sensitivity to ETV and/or LTV and optionally other nucleoside analogs. Preferably, the decreased sensitivity is to ETV, or both LMV and/or ETV.

Another preferred aspect of the present invention contemplates an HBV variant comprising a mutation in the nucleotide sequence encoding HBsAg resulting in an amino acid addition, substitution and/or deletion in said HBsAg in a region corresponding to the amino acid sequence set forth in Formulas I and II wherein said variant exhibits decreased sensitivity to ETV and/or LMV and optionally other nucleoside analogs.

More particularly, the present invention provides a variant HBV comprising a surface antigen having an amino acid sequence with a single or multiple amino acid substitution, addition and/or deletion or a truncation compared to a surface antigen from a reference or wild type HBV, and wherein an antibody generated to the reference or wild type surface antigen exhibits reduced capacity for neutralizing said HBV variant, said variant selected by exposure of a subject to ETV and/or LMV in combination or sequential therapy.

The term "combination therapy" means that both ETV and LMV are co-administered in the same composition or simultaneously in separate compositions. The term "sequential therapy" means that the two agents are administered within seconds, minutes, hours, days or weeks of each other and in either order. Sequential therapy also encompasses completing a therapeutic course with one or other of ETV or LMV and then completing a second therapeutic course with the other of ETV or LMV.

Accordingly, another aspect of the present invention contemplates an HBV variant comprising a surface antigen having an amino acid sequence with a single or multiple amino acid substitution, addition and/or deletion or truncation compared to the pretreatment HBV, and wherein the surface antigen of the variant HBV exhibits an altered immunological profile compared to the pretreatment HBV, where the said variant HBV is selected for by a nucleoside analog of the HBV DNA polymerase, said variant selected by exposure of a subject to ETV and/or LMV in combination or sequential therapy.

In a related embodiment, the present invention provides an HBV variant comprising a nucleotide sequence comprising a single or multiple nucleotide substitution, addition and/or deletion compared to the pretreatment HBV, and which HBV variant has a surface antigen exhibiting an altered immunological profile compared to the pretreatment HBV, said variant selected by exposure of a subject to ETV and/or LMV in combination or sequential therapy.

Preferably, the variants are in isolated form such that they have undergone at least one purification step away from naturally occurring body fluid. Alternatively, the variants may be maintained in isolated body fluid or may be in DNA form. The present invention also contemplates infectious molecular clones comprising the genome or parts thereof from a variant HBV. Furthermore, the present invention provides isolated components from the variant HBVs, such as but not limited to, an isolated HBsAg. Accordingly, the present invention provides an isolated HBsAg or a recombinant form thereof or derivative or chemical equivalent thereof, said HBsAg being from a variant HBV selected by exposure of a subject to ETV and/or LMV in combination or sequential therapy.

More particularly, yet another aspect of the present invention is directed to an isolated variant HBsAg or a recombinant or derivative form thereof or a chemical equivalent thereof, wherein said HBsAg or its recombinant or derivative form or its chemical equivalent exhibits an altered immunological profile compared to an HBsAg from a reference HBV, said HBsAg being from a variant HBV selected by exposure of a subject to ETV and/or LMV in combination or sequential therapy.

Even more particularly, the present invention provides an isolated variant HBsAg or a recombinant or derivative form thereof or a chemical equivalent thereof, wherein said HBsAg or its recombinant or derivative form or its chemical equivalent comprises an amino acid sequence with a single or multiple amino acid substitution, addition and/or deletion or a truncation compared to an HBsAg from a reference HBV, and wherein a neutralizing antibody directed to a reference HBV exhibits no or reduced neutralizing activity to an HBV carrying said variant HBsAg, said HBsAg being from a variant HBV selected by exposure of a subject to ETV and/or LMV in combination or sequential therapy.

Preferred mutations in the HBV DNA polymerase include variants selected from patients with HBV recurrence following ETV and/or LMV treatment. Preferably, the treatment involves ETV or both ETV and/or LMV in combination or sequential therapy. Nucleoside analog treatment may occur in relation to a transplantation procedure (e.g. bone marrow transplantation (BMT) or OLT) or following treatment of patients diagnosed with hepatitis. Following selection of variants, viral loads are obtainable at levels greater than pretreatment levels.

Preferred mutations in the HBV DNA polymerase include one or more of spacerL97I, spacerK115R, spacerH116L, spacerL128F, spacerS137G, spacerR139G, spacerF142S, rtY54H, rtL91I, rtA97V, rtY124H, rtH126R, rtS135Y, rtI169T, rtM250V, rtV173L, rtL180M, rtM204V, rtA21S, rtA38E, rtF122L, rtT128N, rtQ130P, rtT184G, rtS202I, rtH248N, rtY252L, combinations thereof or an equivalent one or more other mutation thereof is indicative of a variant wherein said variant exhibits a decreased sensitivity to ETV and/or LMV and optionally other nucleoside analogs. It should be noted that the nomenclature system for amino acid positions is based on the methionine residues in the YMDD motif being designated codon rtM204. This numbering system is different to that in Australian Patent No. 734831, where the methionine residue in the YMDD motif within the polymerase gene is designated codon 550. In this regard, rtV173L, rtL180M and rtM204V correspond to V519L, L526M and M550V, respectively, in Australian Patent No. 734831. The term "SPACER" means a region that has been designated between two functional regions: terminal protein and reverse transcriptase. It provides the correct folding for the functional regions and no other specific function has been designated for this region. Corresponding mutations may also occur in envelope genes, such as in one or more of PreS1, PreS2 and HBsAg. Particular mutations are as follows: PreS1 N114D, PreS1 T115S, PreS2 F22L, PreS2 V39A, PreS2 P52L, sL89V, s T118A, s 161L, sE164D, sI195M, sI208T PreS1 E86Q, PreS1 N91K, PreS2 P41H, sQ30K, sP120T, sL176V, sV194F, combinations thereof or an equivalent one or more other mutation thereof is indicative of a variant, wherein said variant exhibits a decreased sensitivity to ETV and/or LMV and optionally other nucleoside analogs. The mutations in the gene encoding HBsAg at sF161L, sE164D, or sI195M also result in mutations in the polymerase gene rtI169T, rtV173L, or rtM204V respectively. Other corresponding mutations may occur in the rt, such as spacerL97I, spacerK115R, spacerH116L, spacerL128F, spacerS137G, spacerR139G, spacerF142S, rtY54H, rtL91I, rtA97V, rtY124H, rtH126R, rtS135Y, rtI169T, rtM250V, rtV173L, rtL180M, rtM204V, rtA21S, rtA38E, rtF122L, rtT128N, rtQ130P, rtT184G, rtS202I, rtH248N, rtY252L, combinations thereof or an equivalent one or more other mutation thereof is indicative of a variant, wherein said variant exhibits a decreased sensitivity to ETV and/or LMV and optionally other nucleoside analogs.

The identification of the variants of the present invention permits the generation of a range of assays to detect such variants. The detection of such variants may be important in identifying resistant variants to determine the appropriate form of chemotherapy and/or to monitor vaccination protocols, or develop new or modified vaccine preparations.

Still another aspect of the present invention contemplates a method for determining the potential for an HBV to exhibit reduced sensitivity to ETV and/or LMV or optionally other nucleoside analogs, said method comprising isolating DNA or corresponding mRNA from said HBV and screening for a mutation in the nucleotide sequence encoding HBV DNA polymerase resulting in at least one amino acid substitution, deletion and/or addition in any one or more of domains F and A through E or a region proximal thereto of said DNA polymerase and associated with resistance or decreased sensitivity to ETV and/or LMV, wherein the presence of such a mutation is an indication of the likelihood of resistance to said ETV and/or LMV.

Preferably, the assay detects one or more of the following mutations in the spacer region and/or the rt region: spacerL97I, spacerK115R, spacerH116L, spacerL128F, spacerS137G, spacerR139G, spacerF142S, rtY54H, rtL91I, rtA97V, rtY124H, rtH126R, rtS135Y, rtI169T, rtM250V, rtV173L, rtL180M, rtM204V, rtA21S, rtA38E, rtF122L, rtT128N, rtQ130P, rtT184G, rtS202I, rtH248N, rtY252L, combinations thereof or an equivalent one or more mutation is indicative of a variant, wherein said variant exhibits a decreased sensitivity to ETV and/or LMV and optionally other nucleoside analogs.

Accordingly, another aspect of the present invention produces a method for determining whether an HBV strain exhibits reduced sensitivity to a nucleoside analog, said method comprising isolating DNA or corresponding mRNA from said HBV and screening for a mutation in the nucleotide sequence encoding the DNA polymerase, wherein the presence of the following mutations in the spacer region and the rt region: spacerL97I, spacerK115R, spacerH116L, spacerL128F, spacerS137G, spacerR139G, spacerF142S, rtY54H, rtL91I, rtA97V, rtY124H, rtH126R, rtS135Y, rtI169T, rtM250V, rtV173L, rtL180M, rtM204V, rtA21S, rtA38E, rtF122L, rtT128N, rtQ130P, rtT184G, rtS202I, rtH248N, rtY252L, combinations thereof or an equivalent one or more other mutation thereof is indicative of a variant wherein said variant exhibits a decreased sensitivity to ETV and/or LMV and optionally other nucleoside analogs.

The preferred mutations in the reverse transcriptase are rtI169T, rtV173L, rtL180M, rtT184G, rtS202I, rtM204V, combinations thereof or an equivalent one or more other mutation thereof is indicative of a variant wherein said variant exhibits a decreased sensitivity to ETV and/or LMV and optionally other nucleoside analogs.

Accordingly, another aspect of the present invention contemplates a method for determining whether an HBV strain exhibits reduced sensitivity to a nucleoside analog, said method comprising isolating DNA or corresponding mRNA from said HBV and screening for a mutation in the nucleotide sequence encoding the DNA polymerase wherein the presence of the following mutations in the B or C domain of the rt region: rtI169T, rtV173L, rtL180M, rtT184G, rtS202I, rtM204V, combinations thereof or an equivalent one or more other mutation thereof is indicative of a variant wherein said variant exhibits a decreased sensitivity to ETV and/or LMV and optionally other nucleoside analogs.

The detection of HBV or its components may be performed on cells, cell lysates, cultured supernatant fluid and bodily fluid and may be by any convenient means including any nucleic acid-based detection means, for example, by nucleic acid hybridization techniques or via one or more polymerase chain reactions (PCRs). The term "bodily fluid" includes any fluid derived from the blood, lymph, tissue or organ systems including serum, whole blood, biopsy and biopsy fluid, organ explants and organ suspension such as liver suspensions. The invention further encompasses the use of different assay formats of said nucleic acid-based detection means, including restriction fragment length polymorphism (RFLP), amplified fragment length polymorphism (AFLP), single-strand chain polymorphism (SSCP), amplification and mismatch detection (AMD), interspersed repetitive sequence polymerase chain reaction (IRS-PCR), inverse polymerase chain reaction (iPCR) and reverse transcription polymerase chain reaction (RT-PCR), amongst others. Other forms of detection include Northern blots, Southern blots, PCR sequencing, antibody procedures, such as ELISA, Western blot and immunohistochemistry. A particularly useful assay includes the reagents and components required for immobilized oligonucleotide- or oligopeptide-mediated detection systems.

One particularly useful nucleic acid detection system is the reverse hybridization technique. In this technique, DNA from an HBV sample is amplified using a biotin or other ligand-labeled primer to generate a labeled amplificon. Oligonucleotides immobilized to a solid support such as a nitrocellulose film are then used to capture amplified DNA by hybridization. Specific nucleic acid fragments are identified via biotin or the ligand. Generally, the labeled primer is specific for a particular nucleotide variation to be detected. Amplification occurs only if the variation to be detected is present. There are many forms of the reverse hybridization assay and all are encompassed by the present invention.

Detecting HBV replication in cell culture is particularly useful.

Another aspect of the present invention contemplates a method for detecting an agent which exhibits inhibitory activity to an HBV by:
  generating a genetic construct comprising a replication competent-effective amount of the genome from the HBV contained in a plasmid vector and then transfecting said cells with said construct;
  contacting the cells, before, during and/or after transfection, with the agent to be tested;
  culturing the cells for a time and under conditions sufficient for the HBV to replicate, express genetic sequences, assemble and/or release virus or virus-like particles if resistant to said agents; and
  then subjecting the cells, cell lysates or culture supernatant fluid to viral- or viral-component-detection means to determine whether or not the virus has replicated, expressed genetic material, assembled and/or been released in the presence of the agent.

In a preferred embodiment, the plasmid vector may include genes encoding part or all of other viral vectors such as baculovirus or adenovirus (Ren and Nassal, 2001, supra) and the method comprises:
  generating a genetic construct comprising a replication competent-effective amount of the genome from the HBV contained in or fused to an amount of a baculovirus genome or adenovirus genome effective to infect cells and then infecting said cells with said construct;
  contacting the cells, before, during and/or after infection, with the agent to be tested;
  culturing the cells for a time and under conditions sufficient for the HBV to replicate, express genetic sequences, assemble and/or release virus or virus-like particles if resistant to said agent; and
  then subjecting the cells, cell lysates or culture supernatant fluid to viral- or viral-component-detection means to determine whether or not the virus has replicated, expressed genetic material and/or assembled and/or been released in the presence of the agent.

In an alternative embodiment, the method comprises:
  generating a continuous cell line comprising an infectious copy of the genome of the HBV in a replication competent effective amount such that said infectious HBV genome is stably integrated into said continuous cell line such as but not limited to 2.2.15 or AD;
  contacting the cells with the agent to be tested;
  culturing the cells for a time and under conditions sufficient for the HBV to replicate, express genetic sequences, assemble and/or release virus or virus-like particles if resistant to the agent; and
  then subjecting the cells, cell lysates or culture supernatant fluid to viral- or viral-component-detection means to determine whether or not the virus has replicated, expressed genetic material, assembled and/or been released in the presence of the agent.

As indicated above, variants may also be detected with reference to the HBsAg (s gene) and Pres1, Pres2 envelop genes. Preferred mutations in this regard include one or more of PreS1 N114D, PreS1 T115S, PreS2 F22L, PreS2 V39A, PreS2 P52L, sL89V, sT118A, sF161L, sE164D, sI195M, sI208T PreS1 E86Q, PreS1 N91K, PreS2 P41H, sQ30K, sP120T, sL176V, sV194F.

Accordingly, another aspect of the present invention contemplates a method for determining whether an HBV strain exhibits reduced sensitivity to a nucleoside analog, said method comprising isolating DNA or corresponding mRNA from said HBV and screening for a mutation in the nucleotide sequence encoding the envelope genes wherein the presence of the following mutations in the PreS1, PreS2 and HBsAg: PreS1 N114D, PreS1 T115S, PreS2 F22L, PreS2 V39A, PreS2 P52L, sL89V, sT118A, sF161L, sE164D, sI195M, sI208T PreS1 E86Q, PreS1 N91K, PreS2 P41H, sQ30K, sP120T, sL176V, sV194F, combinations thereof or an equivalent one or more other mutation thereof is indicative of a variant wherein said variant exhibits a decreased sensitivity to ETV and/or LMV and optionally other nucleoside analogs.

The present invention is predicated in part on the identification and isolation of variants of HBV that have a plurality of mutations and exhibit two or more characteristics selected from decreased or reduced sensitivity to one or more nucleoside analogs, a reduced level and/or functional activity of hepatitis B e antigen, or a reduced, abrogated or otherwise impaired immunological interactivity, relative to wild-type HBV. Thus, the identification of HBV variants with these mutational patterns is important inter alia for the development of assays to detect HBV variants and assays to screen for agents which are useful in treating and/or preventing infections by those variants and/or other HBV isolates and for the development of alternative therapeutic regimes for managing HBV infections.

Accordingly, one aspect of the present invention is directed to an isolated HBV variant comprising a plurality of nucleotide mutations that correlate with at least two characteristics selected from (a) resistance to one or more nucleoside analogs, (b) a reduced level and/or functional activity of hepatitis B e antigen, or (c) a reduced, abrogated or otherwise impaired immunological interactivity.

Another aspect of the present invention contemplates an isolated HBV variant comprising a plurality of nucleotide mutations that correlate with (a) resistance to one or more nucleoside analogs, (b) a reduced level and/or functional activity of hepatitis B e antigen, and (c) a reduced, abrogated or otherwise impaired immunological interactivity.

Yet another aspect of the present invention provides an isolated HBV variant comprising a plurality of nucleotide mutations selected from two or more of (a) a nucleotide mutation in a gene encoding a DNA polymerase resulting in at least one amino acid addition, substitution and/or deletion to said DNA polymerase wherein said variant exhibits decreased sensitivity to ETV and/or LMV and optionally other nucleoside analogs, (b) a nucleotide mutation in a gene encoding a hepatitis B e antigen or in a transcriptional control element of said gene wherein said mutation results in a reduced level and/or functional activity of said hepatitis B e antigen, or (c) a nucleotide mutation in a gene encoding a hepatitis B polypeptide resulting in at least one amino acid addition, substitution and/or deletion to said polypeptide which reduces, abrogates or otherwise impairs its immunological interactivity.

The detection of amino acid variants of DNA polymerase is conveniently accomplished by reference to the amino acid sequence shown in Formulas I and II. The polymorphisms shown represent the variations shown in various databases for active pathogenic HBV strains. Where an HBV variant comprises an amino acid different to what is represented, then such an isolate is considered a putative HBV variant having an altered DNA polymerase activity.

The present invention further contemplates agents which inhibit ETV and/or LMV resistant HBV variants. Such agents will be particularly useful if long term treatment by ETV and/or LMV and/or optionally other nucleoside analogs is contemplated by the clinician. The agents may be DNA or RNA or proteinaceous or non-proteinaceous chemical molecules. Natural product screening such as from plants, coral and microorganisms is also contemplated as a useful potential source of masking agents. The agents may be in isolated form or in the form of a pharmaceutical composition and may be administered sequentially or simultaneously with the nucleoside analog.

Accordingly, another aspect of the present invention contemplates a method for detecting an agent which exhibits inhibitory activity to an HBV, exhibiting resistance or decreased sensitivity to ETV and/or LMV, said method comprising:

generating a genetic construct comprising a replication competent-effective amount of the genome from said HBV contained in a plasmid vector and then transfecting said cells with said construct;

contacting said cells, before, during and/or after transfection, with the agent to be tested;

culturing said cells for a time and under conditions sufficient for the HBV to replicate, express genetic sequences and/or assemble and/or release virus or virus-like particles if resistant to said agent; and performing viral- or viral-component-detection means to determine whether or not the virus has replicated, expressed genetic material, assembled and/or been released in the presence of said agent.

Still another aspect of the present invention provides a method for detecting an agent which exhibits inhibitory activity to an HBV, exhibiting resistance or decreased sensitivity to ETV and/or LMV, said method comprising:

generating a genetic construct comprising a replication competent-effective amount of the genome from said HBV contained in or fused to an amount of a baculovirus genome effective to infect cells and then infecting said cells with said construct;

contacting said cells, before, during and/or after infection, with the agent to be tested;

culturing said cells for a time and under conditions sufficient for the HBV to replicate, express genetic sequences and/or assemble and/or release virus or virus-like particles if resistant to said agent; and performing viral- or viral-component-detection means to determine whether or not the virus has replicated, expressed genetic material and/or assembled and/or been released in the presence of said agent.

Still another aspect of the present invention provides a method for detecting an agent which exhibits inhibitory activity to an HBV, exhibiting resistance or decreased sensitivity to ETV and/or LMV, said method comprising:

generating a genetic construct comprising a replication competent-effective amount of the genome from said HBV contained in or fused to an amount of a baculovirus genome effective to infect cells and then infecting said cells with said construct;

contacting said cells, before, during and/or after infection, with the agent to be tested;

culturing said cells for a time and under conditions sufficient for the HBV to replicate, express genetic sequences and/or assemble and/or release virus or virus-like particles if resistant to said agent; and performing viral- or viral-component-detection means to determine whether or not the virus has replicated, expressed genetic material and/or assembled and/or been released in the presence of said agent.

Preferably, the HBV genome is stably integrated into the cells' genome.

While the baculovirus vector is a particularly useful in the practice of the present invention, the subject invention extends to a range of other vectors such as but not limited to adenoviral vectors.

The present invention further extends to cell lines carrying genetic constructs comprising all or a portion of an HBV genome or a gene or part of a gene therefrom.

The present invention also provides for the use of the subject HBV variants to screen for anti-viral agents. These anti-viral agents inhibit the virus. The term "inhibit" includes antagonizing or otherwise preventing infection, replication, assembly and/or release or any intermediate step. Preferred anti-viral agents include nucleoside analogs, however, the present invention extends to non-nucleoside molecules.

In addition, rational drug design is also contemplated to identify or generate chemical molecules which either mimic a nucleoside or which interact with a particular nucleotide sequence or a particular nucleotide. Combinatorial chemistry and two hybrid screening are some of a number of techniques which can be employed to identify potential therapeutic or diagnostic agents.

In one example, the crystal structure of polymerase or the surface antigen is used to rationally design small chemical molecules likely to interact with key regions of the molecule required for function and/or antigenicity. Such agents may be useful as inhibitors of polymerase activity and/or may alter an epitope on the surface antigen.

Several models of the HBV polymerase have been prepared due to the similarity with reverse transcriptase from HIV (Das et al., *J. Virol* 75(10): 4771-4779, 2001; Bartholomeusz et al., *Intervirology* 40(5-6): 337-342 1997; Allen et al., *Hepatology* 27(6): 1670-1677, 1998). The models of the HBV polymerase can be used for the rational drug design of new agents effective against HBV encoding the resistant mutations, as well as wild type virus. The rational drug that is designed may be based on a modification of an existing anti-viral agent such as the agent used in the selection of the HBV encoding the mutations associated with resistance. Viruses or clones expressing HBV genomic material encoding the mutations may also be used to screen for new antiviral agents.

The above methods are particularly useful in identifying an inhibitor of a ETV- and/or LMV-resistant HBV. The present invention extends, therefore, to compositions of the inhibitors. The inhibitors may also be in the form of antibodies or genetic molecules such as ribozymes, antisense molecules and/or sense molecules for co-suppression or the induction of RNAi. Reference to RNAi includes reference to siRNA.

The term "composition" includes a "pharmaceutical composition".

The inhibitor is referred to below as an "active ingredient" or "active compound" and may be selected from the list of inhibitors given above.

The composition may include an antigenic component of the HBV, a defective HBV variant or an agent identified through natural product screening or rational drug design (including combinatorial chemistry).

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

The pharmaceutical composition may also comprise genetic molecules such as a vector capable of transfecting target cells where the vector carries a nucleic acid molecule capable of encoding an aspartyl protease inhibitor. The vector may, for example, be a viral vector.

Pharmaceutical forms suitable for injectable use include sterile aqueous solutions (where water soluble) and sterile powders for the extemporaneous preparation of sterile injectable solutions. It must be stable under the conditions of manufacture and storage and must be preserved against the contaminating action of microorganisms such as bacteria and fungi. The carrier can be a solvent or dilution medium comprising, for example, water, ethanol, polyol (for example, glycerol, propylene glycol and liquid polyethylene glycol, and the like), suitable mixtures thereof and vegetable oils. The proper fluidity can be maintained, for example, by the use of superfactants. The preventions of the action of microorganisms can be brought about by various anti-bacterial and anti-fungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with the active ingredient and optionally other active ingredients as required, followed by filtered sterilization or other appropriate means of sterilization. In the case of sterile powders for the preparation of sterile injectable solutions, suitable methods of preparation include vacuum drying and the freeze-drying technique, which yield a powder of active ingredient plus any additionally desired ingredient.

When the active ingredient is suitably protected, it may be orally administered, for example, with an inert diluent or with an assimilable edible carrier, or it may be enclosed in hard or soft shell gelatin capsule, or it may be compressed into tablets. For oral therapeutic administration, the active ingredient may be incorporated with excipients and used in the form of ingestible tablets, buccal tablets, troches, capsules, elixirs, suspensions, syrups, wafers and the like. Such compositions and preparations should contain at least 1% by weight of active compound. The percentage of the compositions and preparations may, of course, b varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 200 mg of active compound. Alternative dosage amounts include from about 1 µg to about 1000 mg and from about 10 µg to about 500 mg. These dosages may be per individual or per kg body weight. Administration may be per hour, day, week, month or year.

The tablets, troches, pills, capsules and the like may also contain the components as listed hereafter. A binder, such as gum, acacia, corn starch or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen or cherry flavouring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and a flavoring. Of course, any material used in preparing any dosage unit form should be pharmaceutically pure and substantially non-toxic in the amounts employed. In addition, the active compound(s) may be incorporated into sustained-release preparations and formulations.

As stated above, the present invention further extends to an isolated HBsAg from the HBV variants herein described. More particularly, the present invention provides an HBsAg or a recombinant form thereof or derivative or chemical equivalent thereof. The isolated surface component and, more particularly, isolated surface antigen or its recombinant, derivative or chemical equivalents are useful in the development of biological compositions such as vaccine formulations.

Yet another aspect of the present invention provides a composition comprising a variant HBV resistant to ETV and/or LMV and optionally other nucleoside analogs or an HBV surface antigen from said variant HBV or a recombinant or derivative form thereof or its chemical equivalent and one or more pharmaceutically acceptable carriers and/or diluents.

As indicated above, antibodies may be generated to the mutant HBV agents and used for passive or direct vaccination against infection by these viruses. The antibodies may be generated in humans or non-human animals. In the case of the latter, the non-human antibodies may need to be deimmunized or more specifically humanized prior to use. Deimmunized may include, for example, grafting complimentarity determining regions (CDRs) from the variable region of a murine or non-human animal anti-HBV antibody onto a human consensus fragment antibody binding (Fab) polypeptide. Alternatively, amino acids defining epitopes in the variable region of the antibody may be mutated so that the epitopes are no longer recognized by the human MHC II complex.

Insofar as ribozyme, antisense or co-suppression (RNAi) repression is concerned, this is conveniently aimed at post-transcription gene silencing. DNA or RNA may be administered or a complex comprising RNAi or a chemical analog thereof specific for HBV mRNA may be employed.

All such molecules may be incorporated into pharmaceutical compositions.

In another embodiment, the present invention provides a biological composition comprising a variant HBV or an HBsAg or L, M or S proteins from said variant HBV or a recombinant or derivative form thereof or its chemical equivalent. The biological composition may also be used as an immunogenic composition, capable of inducing an immune response in a subject.

Generally, if an HBV is used, it is first attenuated. The biological composition according to this aspect of the present invention generally further comprises one or more pharmaceutically acceptable carriers and/or diluents.

The biological composition may comprise HBsAg or like molecule from one HBV variant or the composition may be a cocktail of HBsAgs or L, M or S proteins or like molecules from a range of ETV- and/or LMV-resistant HBV variants. Similar inclusions apply where the composition comprises an HBV.

The present invention is further directed to the use of defective HBV variants in the manufacture of therapeutic vaccines to vaccinate individuals against infection by HBV strains having a particular nucleotide sequence or encoding a particular polymerase or surface antigen or L, M or S proteins.

In one embodiment, for example, an HBV variant may be identified having a particular mutation in its polymerase conferring resistance or decreased sensitivity to a nucleoside analog. This variant may then be mutated to render it defective, i.e. attenuated or unable to cause infection. Such a defective, nucleoside analog-resistant virus may then be used as a therapeutic vaccine against virulent viruses having the same mutation in its polymerase.

The subject invention extends to kits for assays for variant HBV resistant to ETV and/or LMV. Such kits may, for example, contain the reagents from PCR or other nucleic acid hybridization technology or reagents for immunologically based detection techniques. A particularly useful assay includes the reagents and components required for immobilized oligonucleotide- or oligopeptide-mediated detection systems.

Still another aspect of the present invention contemplates a method for determining the potential for an HBV to exhibit reduced sensitivity to ETV and/or LMV or optionally other nucleoside analogs, said method comprising isolating DNA or corresponding mRNA from said HBV and screening for a mutation in the nucleotide sequence encoding HBV DNA polymerase resulting in at least one amino acid substitution, deletion and/or addition in any one or more of domains F and A through E or a region proximal thereto of said DNA polymerase and associated with resistance or decreased sensitivity to ETV and/or LMV wherein the presence of such a mutation is an indication of the likelihood of resistance to said ETV and/or LMV.

An assessment of a potential viral variant is important for selection of an appropriate therapeutic protocol. Such an assessment is suitably facilitated with the assistance of a computer programmed with software, which inter alia adds index values ($I_v$s) for at least two features associated with the viral variants to provide a potency value ($P_A$) corresponding to the resistance or sensitivity of a viral variant to a particular chemical compound or immunological agent. The $I_v$s can be selected from (a) the ability to exhibit resistance for reduced sensitivity to a particular compound or immunological agent; (b) an altered DNA polymerase from wild-type HBV; (c) an altered surface antigen from wild-type HBV; or (d) morbidity or recovery potential of a patient. Thus, in accordance with the present invention, $I_v$s for such features are stored in a machine-readable storage medium, which is capable of processing the data to provide a $P_A$ for a particular viral variant or a biological specimen comprising same.

Thus, in another aspect, the invention contemplates a computer program product for assessing the likely usefulness of a viral variant or biological sample comprising same for determining an appropriate therapeutic protocol in a subject, said product comprising:
(1) code that receives as input $I_v$s for at least two features associated with said viral agents or biological sample comprising same, wherein said features are selected from the group consisting of:
  (a) the ability to exhibit resistance for reduced sensitivity to a particular compound or immunological agent;
  (b) an altered DNA polymerase from wild-type HBV;
  (c) an altered surface antigen from wild-type HBV;
  (d) morbidity or recovery potential of a patient; and
  (e) altered replication capacity (increased or decreased);
(2) code that adds said $I_v$s to provide a sum corresponding to a $P_v$ for said viral variants or biological samples; and
(3) a computer readable medium that stores the codes.

In a related aspect, the invention extends to a computer for assessing the likely usefulness of a viral variant or biological sample comprising same in a subject, wherein said computer comprises:
(1) a machine-readable data storage medium comprising a data storage material encoded with machine-readable data, wherein said machine-readable data comprise $I_v$s for at least two features associated with said viral variant or biological sample; wherein said features are selected from the group consisting of:
  (a) the ability to exhibit resistance for reduced sensitivity to a particular compound or immunological agent;
  (b) an altered DNA polymerase from wild-type HBV;
  (c) an altered surface antigen from wild-type HBV;
  (d) morbidity or recovery potential of a patient; and
  (e) altered replication capacity (increased or decreased);
(2) a working memory for storing instructions for processing said machine-readable data;
(3) a central-processing unit coupled to said working memory and to said machine-readable data storage medium, for processing said machine readable data to provide a sum of said $I_v$s corresponding to a $P_v$ for said compound(s); and
(4) an output hardware coupled to said central processing unit, for receiving said $P_v$.

Figure 7:
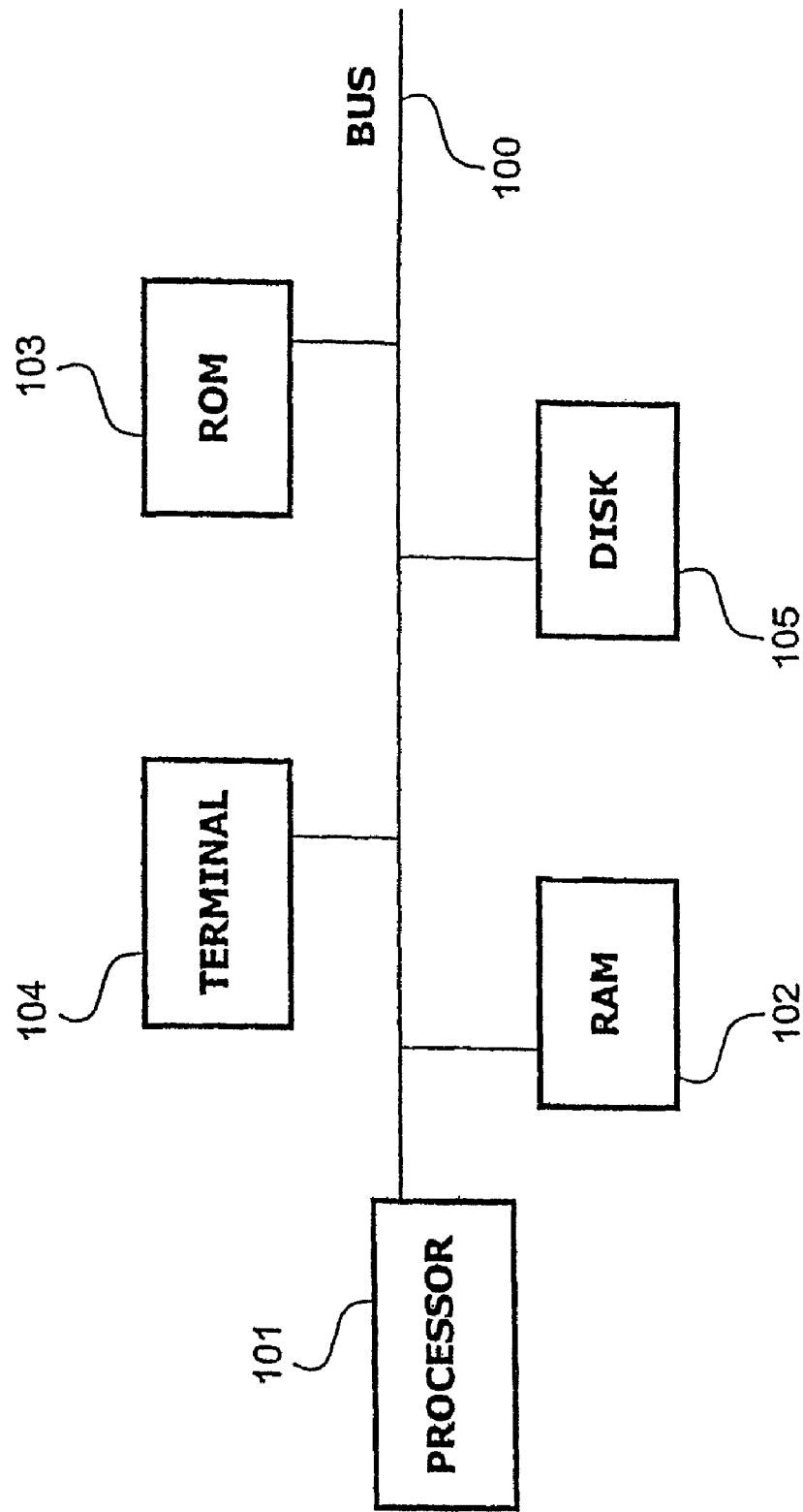
FIG. 7 is a diagrammatic representation of a computer system for determining the potency value ($P_A$) of a variant HBV.

Any general or special purpose computer system is contemplated by the present invention and includes a processor in electrical communication with both a memory and at least one input/output device, such as a terminal. Such a system may include, but is not limited, to personal computers, workstations or mainframes. The processor may be a general purpose processor or microprocessor or a specialized processor executing programs located in RAM memory. The programs may be placed in RAM from a storage device, such as a disk or pre-programmed ROM memory. The RAM memory in one embodiment is used both for data storage and program execution. The computer system also embraces systems where the processor and memory reside in different physical entities but which are in electrical communication by means of a network. For example, a computer system having the overall characteristics set forth in FIG. 7 may be useful in the practice of the instant invention. More specifically, FIG. 7 is a schematic representation of a typical computer work station having in electrical communication (100) with one another via, for example, an internal bus or external network, a processor (101), a RAM (102), a ROM (103), a terminal (104), and optionally an external storage device, for example, a diskette, CD ROM, or magnetic tape (105).

The present invention is further described by the following non-limiting Examples.

Example 1

Overlapping Genome of HBV

The overlapping genome of HBV is represented in FIG. 1. The gene encoding DNA polymerase (P), overlaps the viral envelope genes, Pre-S1 and Pre-S2, and partially overlaps the X and core (C) genes. The HBV envelope comprises small, middle and large HBV surface antigens. The large protein component is referred to as the HBV surface antigen (HBsAg) and is enclosed by the S gene sequence. The Pre-S1 and Pre-S2 gene sequences encode the other envelope components.

Example 2

Patient and Treatment

Figure 2:
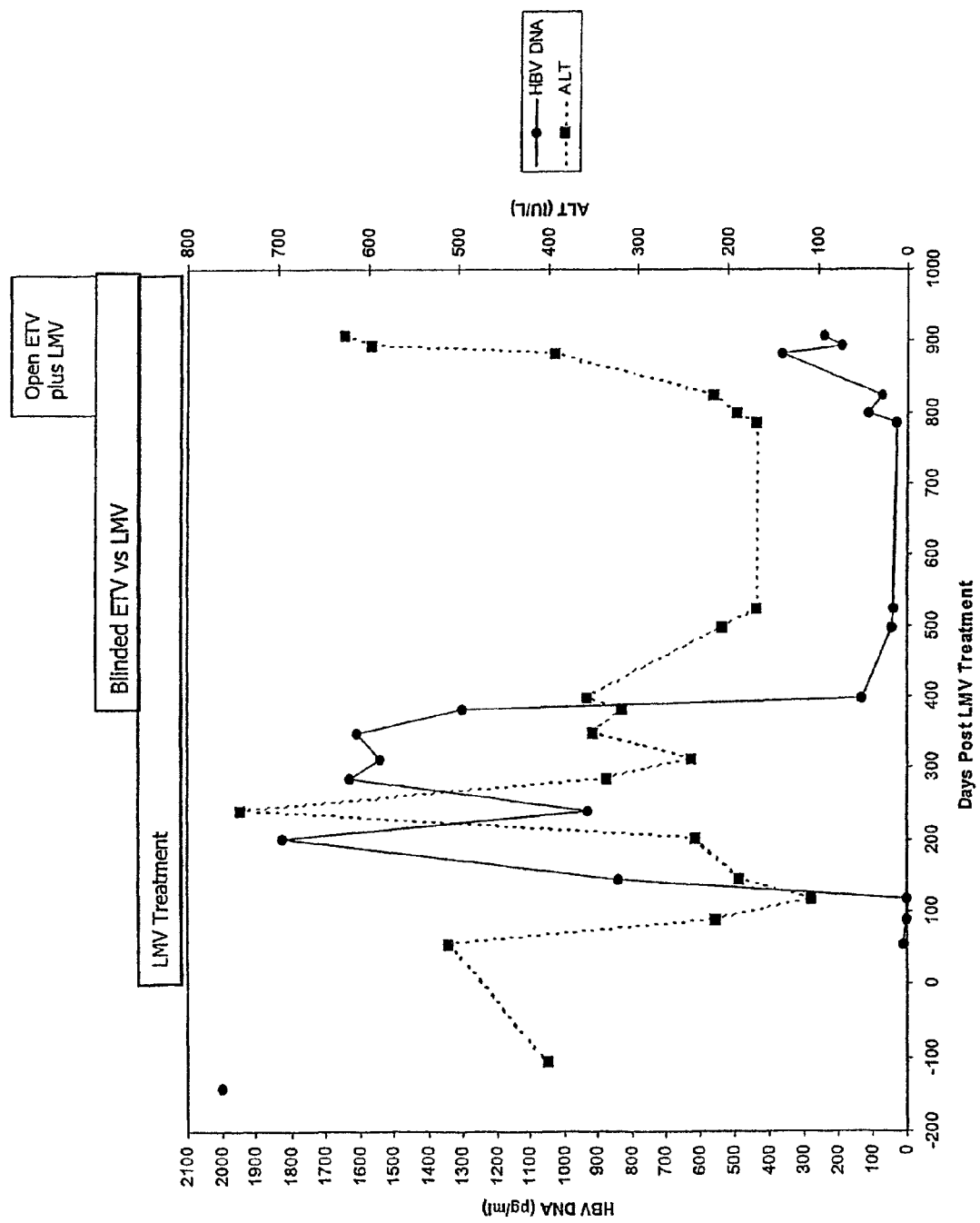
FIG. 2 is graphical representation of Patient A's clinical history including therapy regimen, HBV DNA viral load and alanine transaminase (ALT) levels.

Patient A is a 44 year old male with chronic hepatitis B presented on Day 0 (9 Jul. 1999) with raised serum HBV DNA levels (>2000 pg/ml) and was commenced on LMV treatment immediately (FIG. 2). The patient A was HBsAg positive and anti-HBe positive. Following the initiation of LMV treatment the HBV DNA levels fell to 8 pg/ml over 54 days of therapy. The HBV DNA levels remained low until day 199 when there was a relapse in replication such that HBV DNA levels reached 1826 pg/ml. By Day 241 the serum ALT peaked at 741 IU/1. The HBV DNA was sequenced and LMV resistant virus was detected. The patient was then enrolled on Day 382 (24 Jul. 2000) into a blinded ETV plus LMV clinical trial. HBV DNA levels only decreased to 33 pg/ml and the ALT decreased to 167 IU/L by day 784. The patient was started on open label ETV plus LMV. However, both HBV DNA levels and ALT continued to rise and the HBV DNA was sequenced at day 894 (FIG. 2).

Patient B is a liver transplant patient. This patient has been treated with a number of nucleoside analogs including ganciclovir, famciclovir, LMV and ETV. The patient was treated with LMV prior to ETV. The patient is currently on ETV treatment. During ETV treatment the HBV DNA levels were reduced to less than 5 pg/ml. At 532 days ETV treatment, that corresponds to 3857 days post transplant, there was a rise in the HBV DNA levels to 993 pg/ml. The HBV DNA from this sample was further characterized by sequencing.

Example 3

Detection of Viral Markers

Hepatitis B surface antigen (HBsAg), hepatitis B e antigen (HBeAg), anti-HBe and hepatitis B core antigen (HBcAg) specific IgG and IgM were measured using commercially available immunoassays (Abbott Laboratories, North Chicago, Ill., USA). Hepatitis B viral DNA levels were measured using a capture hybridization assay according to the manufacturer's directions (Digene Hybrid Capture II, Digene Diagnostics Inc., Beltsville, Md.). The manufacturers stated cut-off for detecting HBV viremia in clinical specimens was $0.7 \times 10^6$ copies/ml or 2.5 pg/ml, [Hendricks D A, et al., *Am J Clin Pathol* 104: 537-46, 1995].

Example 4

Sequencing of HBV DNA

HBV DNA was extracted from 100 µl of serum collected at 6 different time points (FIG. 2) as described previously by Aye et al., *J Hepatol*. 26: 1148-53, 1997. Oligonucleotides were synthesized by Geneworks, Adelaide, Australia. Amplification of the HBV polymerase gene has been described by Aye et al., 1997, supra.

The specific amplified products were purified using PCR purification columns from MO BIO Laboratories Inc (La Jolla, Calif.) and directly sequenced using Big Dye terminator Cycle sequencing Ready Reaction Kit (Perkin Elmer, Cetus Norwalk, Conn.). The PCR primers were used as sequencing primers, OS1 5'-GCC TCA TTT TGT GGG TCA CCA TA-3' (nt 1408-1430) [SEQ ID NO: 3], TTA3 5'-AAA TTC GCA GTC CCC AAA-3' (nt2128-2145) [SEQ ID NO: 4], JM 5'-TTG GGG TGG AGC CCT CAG GCT-3' (nt1676-1696) [SEQ ID NO: 5], TTA4 5'-GAA AAT TGG TAA CAG CGG-3' (nt 2615-2632) [SEQ ID NO: 6], OS2 5' TCT CTG ACA TAC TTT CCA AT 3' (nt 2798-2817) [SEQ ID NO: 7], to sequence the internal regions of the PCR products.

Example 5

Analysis of HBV DNA

Patient A: The LMV resistant mutations at rtL180M and rtM204V were detected by sequencing by day 199 (Table 3). During the blinded phase of entecavir and LMV treatment, the mutation at rtV173L was also detected. A unique mutation in the B Domain at rtI169T was detected in combination with the two other B domain mutations at rtL180M and rtV173L as well as the mutation at rtM204V in the C domain. A number of other unique changes were also detected in the polymerase and in the overlapping envelope gene (Table 4, FIGS. 4, 5 and 6). These unique changes were compared to reference sequences from each of the seven genotypes A-G as well as a consensus sequence from pretreatment samples to determine unique changes.

Figure 9:
FIG. 9 is a representation showing comparison of the deduced amino acid sequence of the catalytic region of the polymerase gene in sequential samples from Patient B during LMV monotherapy (prior to ETV) and on ETV therapy.

Patient B: The sample at 532 days ETV treatment was sequenced and was compared to samples prior to ETV treatment (FIGS. 8, 9 and 10) Several polymerase mutations were detected in this sample including rtA21S, rtA38E, rtY54H, rtN76D, rtL91I, rtF122L, rtY124H, rtT128N, rtQ130P, rtL180M, rtT184G, rtS202I, rtM204V, rtH248N, rtY252L. At the start of ETV treatment the patient had been on LMV treatment and the mutations at rtL80M and M204V were detected (FIGS. 8, 9 and 10). The LMV mutations (rtL180M and rtM204V) were detected during ETV treatment even in the absence of the LMV selection pressure and these mutations may also contribute to ETV resistance. At the time of the virological breakthrough on ETV, the LMV selected mutations were still present as well as the mutations listed above. All the mutations listed were compared to reference sequences from each of the seven genotypes A-G as well as a consensus sequence from pretreatment samples to determine unique changes.

Patient B is HBeAg negative and the HBV isolated from this patient encoded a mutation in the precore gene at G1896A that results in a stop codon in the precore protein precoreW28Stop. Mutations in other regions in the genome that included the precore mutation at G1896A may affect the replication fitness of HBV and the sensitivity to antiviral agents in combination with the mutation in the polymerase gene.

Example 6

In Vitro Analysis of Entecavir Resistance

The sensitivity/resistance profile of HBV mutants to entecavir was examined in vitro using recombinant HBV/baculovirus. The procedure for analysing the resistance profile is outlined in the following Examples 7-14.

Example 7

Cell Culture

Sf21 insect cells were maintained in supplemented Grace's insect medium further supplemented with 10% v/v heat-inactivated fetal bovine serum (Gibco BRL, Gaithersburg, Md.) in humidified incubator at 28 C with $CO_2$. HepG2 cells were maintained in minimal essential medium supplemented with 10% v/v heat-inactivated fetal bovine serum (MEM-FBS). HepG2 cells were grown in humidified 37° C. incubators at 5% v/v $CO_2$.

Example 8

Preparation of HBV/Baculovirus Transfer Vector with Specific Point Mutations

The recombinant HBV/baculovirus system used for antiviral testing has been previously described (Delaney et al., *Antimicrob Agents Chemother* 45(6): 1705-1013, 2001). In brief, the recombinant transfer vector was created by excising a fragment containing the 1.3×HBV genome construct and cloning it into the multiple cloning region of a baculovirus vector pBlueBac4.5 (Invitrogen, Carlsbad, Calif.). Point mutations were created by site directed mutagenesis using the commercial kits according to the manufacturers specifications (QuikChange, Stratagene). A HBV recombinant encoding the reverse transcriptase mutations rtI169T+rtV173L+rtL180M+rtM204V. The nucleotide sequence of the plasmid and the point mutations generated by site directed mutagenesis were confirmed by sequencing using the ABI Prism Big Dye Terminator Cycle Sequencing Ready Reaction Kit according to the manufacturer's specifications (Perkin Elmer, Cetus Norwalk, Conn.).

Example 9

Generation of Recombinant Baculoviruses Containing the 1.3 HBV Construct

Purified recombinant transfer vector and linear AcMNPV baculovirus DNA were co-transfected into Sf21 cells using the BacNBlue transfection kit from Invitrogen (Carlsbad, Calif.); recombinant viruses were isolated by plaque assay according to the manufacturer's instructions. A series of recombinant viruses were amplified from isolated plaques by infecting 100-mm dishes of Sf21 cells. Viral DNA was extracted from amplified viruses using standard procedures. Purified viral DNA was digested with restriction enzymes and then fractionated by electrophoresis in a 1% v/v agarose gel. Southern blotting was performed to determine which virus isolates contained the intact 1.3 HBV construct. A Boehringer Mannheim Random Prime DNA Labeling kit (Indianapolis, Ind.) was used to generate $[P^{32}]$-radiolabeled probes. A full-length double-stranded HBV genome was used as a template for all radiolabeled probes. Viral DNA sequence was confirmed by PCR amplification of the polymerase catalytic region using the sense primer 5'-GCC TCA TTT TGT GGG TCA CCA TA-3" [SEQ ID NO:3], (nucleotide 1408 to 1430 according to HBV Genebank Accession number M38454) and the antisense primer 5'-TCT CTG ACA TAC TTT CCA AT-3' [SEQ ID NO:6] (nucleotides 2817 to 2798 according to HBV Genebank Accession number M38454). The following primers were utilized for the sequencing of internal regions 5'-TGC ACG ATT CCT GCT CAA-3' [SEQ ID NO:8] (nucleotides 2345-2362 according to HBV Genebank Accession number M38454) and 5'-TTG GGG TGG AGC CCT CAG GCT-3' [SEQ ID NO:9] (nucleotides 1676-1696 according to HBV Genebank Accession number M38454).

Example 10

Preparative Baculovirus Amplification and Purification

Baculoviruses were amplified by infecting suspension cultures of Sf21 cells in log phase at a multiplicity of infection (moi) of 0.5 pfu/cell. Infections were allowed to proceed until a majority of the cells in the flasks showed visible signs of infection (four to five days). Virions were concentrated from infected Sf21 medium by centrifugation at 80,000×g and purified through a 20-60% w/v sucrose gradient. Purified virus was titrated in quadruplicate in Sf21 cells by end-point dilution. An aliquot of each high titer stock was used for DNA extraction. The polymerase gene was amplified and sequenced to confirm the presence of the site-directed mutagenesis as in Example 9.

Example 11

Infection of HepG2 Cells with Recombinant HBV Expressing Baculovirus

HepG2 cells were seeded at approximately 20-40% confluency and then were grown for 16-24 hours before infection. On the day of infection, triplicate plates of cells were trypsinized, and viable cell number was determined with a hemocytometer using Trypan blue exclusion. Average cell counts were calculated and used to determine the volume of high-titer viral stock necessary to infect cells at the indicated moi. HepG2 cells were washed one time with serum-free MEM to remove traces of serum. Baculovirus was diluted into MEM without serum to achieve the appropriate moi using volumes of 1.0, 0.5, and 0.25 ml to infect 100-mm, 60 mm, and 35-mm dishes, respectively. Baculovirus was adsorbed to HepG2 cells for one hour at 37° C. with gentle rocking every 15 minutes to ensure that the inoculum was evenly distributed. The inoculum was then aspirated and HepG2 cells were washed two times with phosphate-buffered saline and refed MEM-FBS with or without various concentrations of agents.

Example 12

Analysis of Secreted HBV Antigen

Detection of hepatitis Be antigen (HBeAg) was performed by radioimmunoassay and microparticle enzyme immunoassay using kits purchased from Abbott Laboratories (Abbott Park, Ill., USA). Medium from HepG2 cells was collected, centrifuged at 6,000 g to remove cellular debris, transferred to clean tubes, and stored at 20° C. until analysis. HBeAg values are expressed as fold of positive control. Medium samples were diluted appropriately so that radioimmunassay results were below positive control values for HBeAg.

Example 13

Detection of Intracellular Replicative Intermediates

HBV core particles were isolated from the cytoplasmic fraction of HepG2 cells lysed in 0.5% w/v NP-40. Cytoplasmic extracts were adjusted to 10 mmol/l McC12 and unprotected DNA was removed by an incubation to 500 g/ml Proteinase K for 1.5 hours at 37° C. HBV DNA in the samples were then extracted using commercial DNA extraction kits such as Qiagen (DNA extraction) or in-house methods using sequential phenol and chloroform extractions, and the nucleic acids were recovered by ethanol precipitation. Nucleic acids were resuspended in 50 µl/l TE (10 mmol/l Tris, 1 mmol/l ethylenediaminetetraacetic acid), normalized by OD260, and digested with 100 g/ml RNase (Boehringer Mannheim, Indianapolis, Ind.) for one hour at 37° C. before analysis by real-time PCR or electrophoresis and Southern blotting. After southern blot analysis a BioRad GS-670 imaging densitometer and the Molecular Analyst software (BioRad, Hecules Calif.) was used to analyze suitable exposures of Southern blots. Densitometry data was fitted to logistic dose response curves using the TableCurve 2D software package from Jandel Scientific. Logistic dose response equations were used to calculate $IC_{50}$ and $IC_{90}$ values and coefficients of variation.

Example 14

Real-Time PCR

For the real-time PCR based assay for HBV, HBV DNA was extracted from 200 µl of serum using the QIAamp DNA Mini Kit according to the manufacturer's instructions (QIAGEN GmbH, Hildens, Germany). Primers and a molecular beacon were designed for conserved nucleic acid sequences within the precore domain of the HBV genome to amplify and detect a 216-nucleotide product (FIG. 1). Amplification was performed in a 50-µl reaction mixture containing 1.0 Taqman buffer A (Applied Biosystems, Foster City, Calif.), 3.0 mM MgCl, 0.4 pmol of each primer per µL, forward primer, PC1 (5'GGGAGGAGATTAGGTTAA3' [SEQ ID NO:10]) and reverse primer, PC2 (5'GGCAAAAACGAGAGTAACTC3' [SEQ ID NO:11]), 0.4 pmol of the HBV-specific molecular beacon per uL, (5'FAM-CGCGTCCTACTGTTCAAGCCTCCAAGCTGT GACGCG-DABCYL-3' [SEQ ID NO:12]; where FAM represents fluorophore 6-carboxyfluorescein and DABCYL, 4-dimethylaminophenylazobenzoic acid, a quenching chromophore) and 1.25 U of AmpliTaq Gold DNA polymerase (Perkin-Elmer). PCR was performed using the ABI PRISM 7700 spectrofluorometric thermocycler (Applied Biosystems). The PCR program consisted of an initial cycle (95° C. for 10 minutes) followed by 45 amplification cycles (94° C. for 15 secs, 50° C. for 30 secs, 72° C. for 30 secs). The instrument detected and recorded the fluorescence spectrum of each reaction tube during the annealing phase.

An external standard was constructed by ligation of a 1.3 kB wild-type HBV plasmid (genotype D) into the pBlueBac plasmid vector (Hershey Medical Center, Hershey, Pa.). Quantification of the DNA concentration of the plasmid was determined by spectrophotometry. Duplicates of serial 10-fold dilutions of the plasmid ranging from $10_8$ copies/ml to 100 copies/ml were included in each run in order to generate a standard curve. The copy number in each experimental reaction was determined by interpolation of the derived threshold cycle (CT).

Example 15

ETV Treatments

ETV was resuspended in sterile water, aliquoted, and frozen at −20° C. to avoid repeated freezing and thawing of the drug. Medium containing ETV was prepared daily as needed using fresh aliquots of 3TC. In experiments in which ETV treatment was initiated after viral infection, HepG2 cells were exposed to the indicated concentration of ETV immediately after infection with HBV baculovirus. In experiments utilizing pretreatment with ETV, cells were fed medium containing ETV 16 hours prior to HBV baculovirus infection, HBV baculovirus infection was also carried out in medium containing ETV, and cells were refed fresh medium containing ETV immediately after completion of the infection and washing procedures.

Example 16

Figure 11:
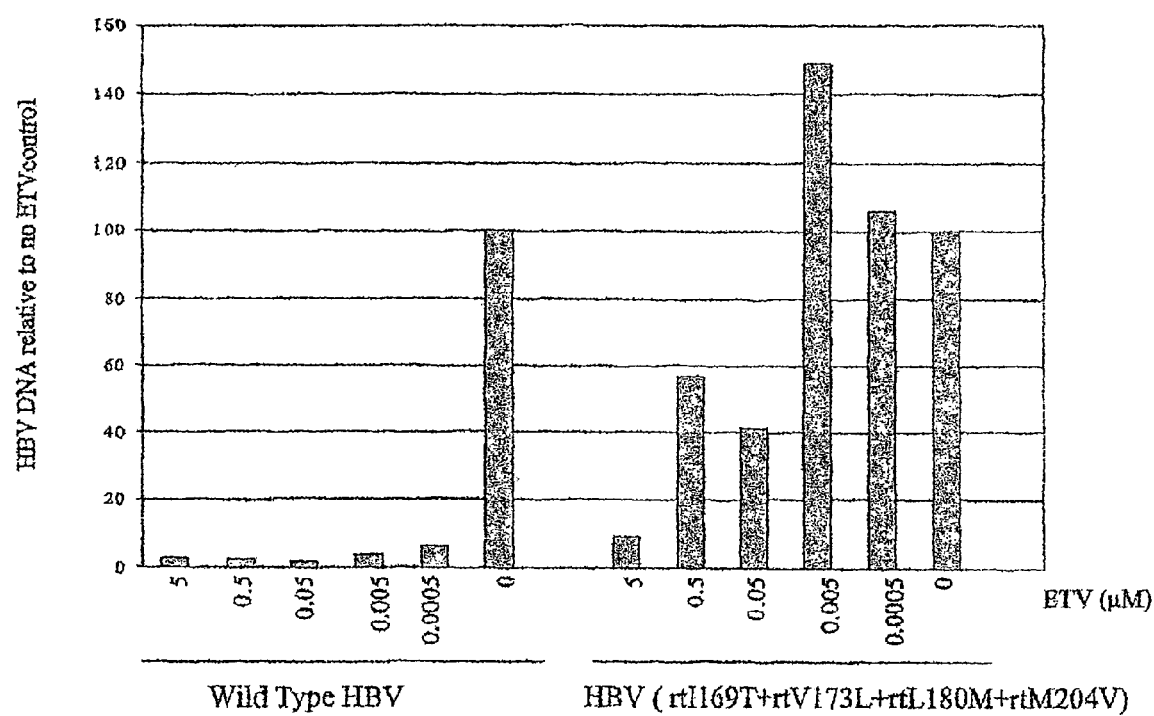
FIG. 11 is a graphical representation of HBV DNA replicative intermediates detected by quantitative PCR relative to the no drug control for both wild type virus and the HBV encoding the mutations at rtI169T+rtV173L+rtL180M+rtM204V.

Antiviral Testing Performed with Wild-Type and HBV/Baculovirus Encoding rtIL69T+rtv173L+rtL180M+rtM204V The graphical analysis of the dose effect of ETV on wild-type HBV and the quadruple mutant HBV are shown in FIG. 11 using the quantitative real-time PCR results relative to wild type virus grown in the absence of ETV (0 µM ETV). ETV had the most pronounced effect on wild-type HBV replication as demonstrated by the reduction in HBV replicative intermediated detected by quantitative PCR at all ETV concentrations tested. In contrast, there was reduced sensitivity to ETV by the recombinant HBV encoding the quadruple mutant (rtI169T+rtV173L+rtL180M+rtM204V) especially at concentrations up to 0.5 µM ETV.

Example 17

ETV

Figure 3:
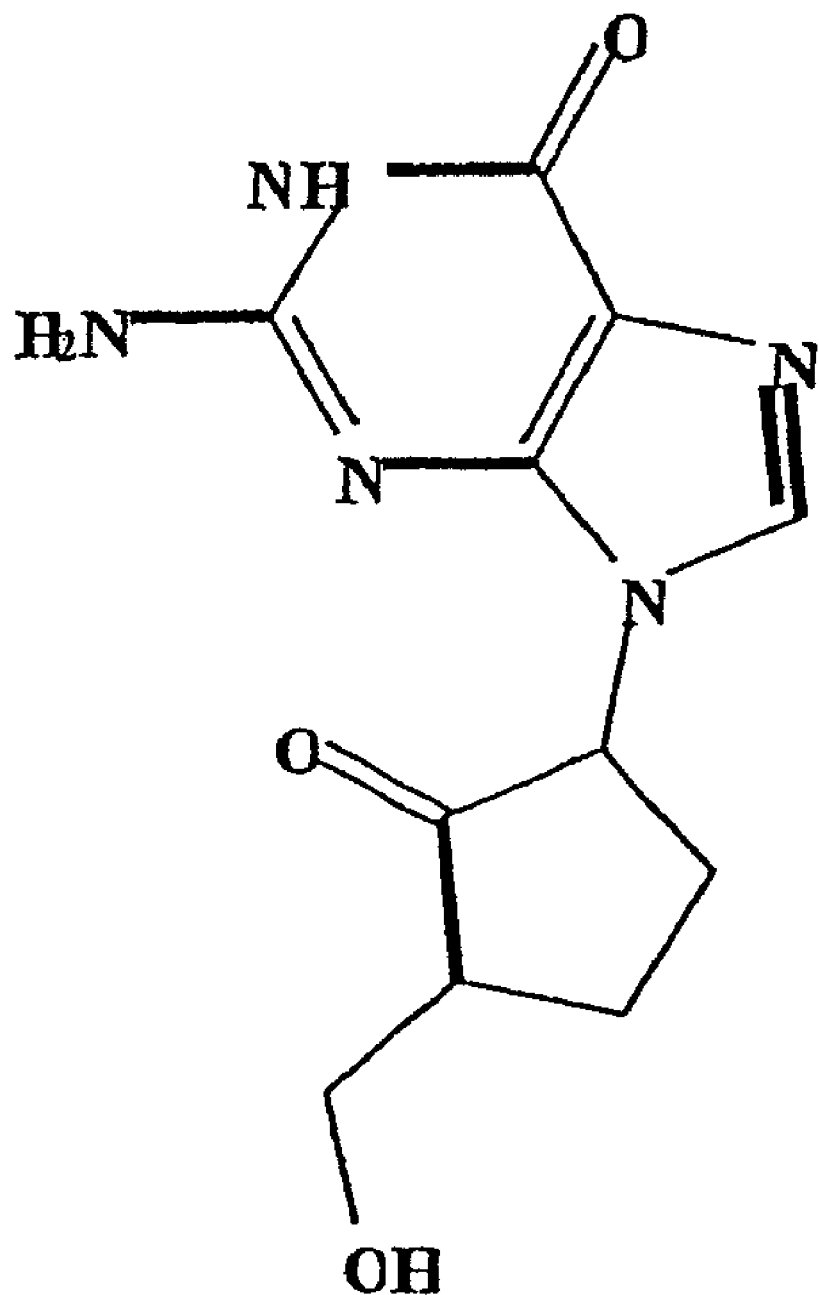
FIG. 3 is a diagrammatic representation of the chemical structure of entecavir.

ETV (formerly BMS-200475 or SQ-34676) is a potent inhibitor of HBV replication. ETV is an cyclopentyl deoxyguanosine analog that has bio-oral available properties with activity against hepadnaviruses and herpesviruses. The structure of ETV is shown in FIG. 3 and its synthesis is described by Bisacchi et al. (*Bioorg. Med. Chem. Lit.* 7: 127-132, 1997). Preclinical studies indicate that entecavir is a highly potent inhibitor of HBV in enzyme- and cell-based assays (Innaimo et al., 1997, supra; Siefer et al., 1998, supra; Yamanaka et al., 1999, supra. ETV was formerly described as BMS-200475 and SQ-34676.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 3

Clinical, virological and HBV sequencing data summary for the patient A with increasing HBV viral loads while on LMV and ETV

| Days Post LMV treatment | HBV DNA pg/ml | HBsAg | HBsAb | HBcAg | Anti-HBc | ALI IU/L | Treatment Protocol | Key Polymerase mutation detected by Sequencing |
|---|---|---|---|---|---|---|---|---|
| −143.00 | >2000 | | | | | n/a | | |
| −107.00 | | detected | | ND | | 399 | | |
| 0.00 | | | | | | | LMV (9 Jul. 1999) | |
| 54.00 | 8 | | | | | 510 | | |
| 87.00 | ND[1] | | | | | 211 | | |
| 115.00 | ND | | | ND | + | 106 | | |
| 173.00 | 837 | | | | | 186 | | |
| 199.00 | 1826 | | | | | 233 | | Sequenced: rtL180M, rtM204M/V[4] |
| 241.00 | 930 | | | ND | + | 741 | | Sequenced: rtL180M, rtM204V |
| 283.00 | 1631 | | | | | 334 | | |
| 312.00 | 1539 | + | ND | ND | + | 238 | | |
| 348.00 | 1605 | + | | ND | + | 349 | | Sequenced rtL180M, rtM204V |
| 382.00 | 1303 | + | ND | ND | + | 317 | ETV vs LMV[2] 24 Jul. 2000 | 00 |
| 397.00 | 131 | | | ND | + | 356 | | Sequenced rtL180M, rtM204V |
| 495.00 | 44 | | | | | 205 | | |
| 523.00 | 41 | | | | | 168 | | Sequenced rtV173V/L rtL180M, rtM204V |
| 784.00 | 33 | + | ND | ND | + | 167 | ETV plus LMV[3] 22 Aug. 2001 | |
| 798.00 | 117 | | | | | 190 | | |
| 826.00 | 75 | + | ND | ND | + | 215 | | |
| 882.00 | 362 | + | ND | ND | + | 392 | | |
| 894.00 | 192 | | | | | 597 | | Sequenced rtI169T, rtV173L, rtL180M, rtM204V |
| 902.00 | 246 | | | | | 627 | | |

[1]ND = not detected
[2]Blinded phase of the study
[3]Open label phase of the study
[4]Nomenclature according to Stuyver et al., 2001, supra

TABLE 4

Summary of HBV mutations in patient A treated with ETV and LMV

| Sample name | Sample date | Days post LMV treatment | PCR Status | Genotype | Polymerase* | Surface |
|---|---|---|---|---|---|---|
| TR1 | 24 Jan. 2000 | 199 | 1R PCR + ve | D | rtL180M** rtM204V/M | sA/V177A/V sI195M/I |
| TR2 | 6 Mar. 2000 | 241 | 1R PCR + ve | D | rtL180M rtV/M204V | sA/V177A/V sL193S sI/M195M |
| TR3 | 21 Jun. 2000 | 348 | 2R PCR + ve | D | rtL180M rtM204V | sV/A177V sS193S/L sI/195M |
| TR4 | 9 Aug. 2000 | 397 | 2R PCR + ve | D | rtL180M rtM204V | sS/L177V sI195M |
| TR5 | 13 Dec. 2000 | 523 | 2R PCR + ve | D | rtV173V/L rtL180M rtM204V | sE164E/D sI195M |
| TR6 | 18 Dec. 2001 | 894 | 1R PCR + ve | D | spacerL97I spacerK115R spacerH116L spacerL128F spacerS137G spacerR139G spacerF142S rtY54H rtL91I rtA97V rtY124H rtH126R rtS135Y, rtI169T, rtM250V | preS1 N114 preS1 T115S preS2 F22L preS2 V39A preS2 P52L sL89V sT118A sP127T sF161L sE164E/D sI/M195M |

TABLE 4-continued

Summary of HBV mutations in patient A treated with ETV and LMV

| Sample name | Sample date | Days post LMV treatment | PCR Status | Genotype | Polymerase* | Surface |
|---|---|---|---|---|---|---|
| | | | | | rtV173V/L | |
| | | | | | rtL180M | |
| | | | | | rtM204V | |

*Nomenclature according to Stuyver et al., 2001, supra

**Mutations in bold have not been detected in reference HBV genotypes, mutations not in bold are changes from the previous sample that are present in reference genotypes

---

We claim:

1. A method for determining whether a hepatitis B test virus from a human patient exhibits reduced sensitivity to entecavir relative to a wild-type hepatitis B virus, the method comprising:
screening a nucleic acid molecule from the test virus for the presence of entecavir-resistance mutations, wherein the nucleic acid molecule comprises a nucleic acid sequence that encodes a reverse transcriptase domain of a DNA polymerase, and the mutations comprise:

(i) mutations at all of codon positions 169, 180, 202 and 204; or (ii) mutations at all of codon positions 169, 180, 184 and 204;

wherein codon positions 169, 180, 184, 202 and 204 correspond to positions 95, 106, 110, 128 and 130, respectively, of SEQ ID NO:2;
wherein the mutation at codon position 169 is a substitution to threonine, the mutation at codon position 180 is a substitution to methionine, and the mutation at codon position 204 is a substitution to isoleucine or valine, and
wherein the presence of mutations comprising combination (i) or (ii) indicates that the test virus exhibits reduced sensitivity to entecavir.

2. The method of claim 1, wherein the mutation at codon position 202 is isoleucine, glycine or cysteine.

3. The method of claim 1, wherein the mutation at codon position 184 is a substitution to glycine, isoleucine, proline, cysteine, alanine, phenylalanine, methionine or serine.

* * * * *

SEQUENCE LISTING

<160> NUMBER OF SEQ ID NOS: 36

<210> SEQ ID NO 1
<211> LENGTH: 76
<212> TYPE: PRT
<213> ORGANISM: artificial sequence
<220> FEATURE:
<223> OTHER INFORMATION: region F of HBV DNA polymerase (Formula I)
<220> FEATURE:
<221> NAME/KEY: MISC_FEATURE
<222> LOCATION: (2)..(2)
<223> OTHER INFORMATION: Xaa = L or R or I
<220> FEATURE:
<221> NAME/KEY: MISC_FEATURE
<222> LOCATION: (3)..(3)
<223> OTHER INFORMATION: Xaa = E or D
<220> FEATURE:
<221> NAME/KEY: MISC_FEATURE
<222> LOCATION: (9)..(9)
<223> OTHER INFORMATION: Xaa = T or D or A or N or Y
<220> FEATURE:
<221> NAME/KEY: MISC_FEATURE
<222> LOCATION: (10)..(10)
<223> OTHER INFORMATION: Xaa = E or D
<220> FEATURE:
<221> NAME/KEY: MISC_FEATURE
<222> LOCATION: (13)..(13)
<223> OTHER INFORMATION: Xaa = E or K or Q
<220> FEATURE:
<221> NAME/KEY: MISC_FEATURE
<222> LOCATION: (15)..(15)
<223> OTHER INFORMATION: Xaa = H or R or N
<220> FEATURE:
<221> NAME/KEY: MISC_FEATURE
<222> LOCATION: (18)..(18)
<223> OTHER INFORMATION: Xaa = I or T
<220> FEATURE:
<221> NAME/KEY: MISC_FEATURE
<222> LOCATION: (23)..(23)
<223> OTHER INFORMATION: Xaa = A or S
<220> FEATURE:
<221> NAME/KEY: MISC_FEATURE
<222> LOCATION: (26)..(26)
<223> OTHER INFORMATION: Xaa = T or R
<220> FEATURE:
<221> NAME/KEY: MISC_FEATURE
<222> LOCATION: (40)..(40)
<223> OTHER INFORMATION: Xaa = A or T or S
<220> FEATURE:
<221> NAME/KEY: MISC_FEATURE
<222> LOCATION: (43)..(43)
<223> OTHER INFORMATION: Xaa = R or T
<220> FEATURE:
<221> NAME/KEY: MISC_FEATURE
<222> LOCATION: (45)..(45)
<223> OTHER INFORMATION: Xaa = V or G
<220> FEATURE:
<221> NAME/KEY: MISC_FEATURE
<222> LOCATION: (55)..(55)
<223> OTHER INFORMATION: Xaa = S or I or T or N or V -continued

```
<220> FEATURE:
<221> NAME/KEY: MISC_FEATURE
<222> LOCATION: (56)..(56)
<223> OTHER INFORMATION: Xaa = T or S or H or Y
<220> FEATURE:
<221> NAME/KEY: MISC_FEATURE
<222> LOCATION: (57)..(57)
<223> OTHER INFORMATION: Xaa = R or H or K or Q
<220> FEATURE:
<221> NAME/KEY: MISC_FEATURE
<222> LOCATION: (69)..(69)
<223> OTHER INFORMATION: Xaa = Q or P
<220> FEATURE:
<221> NAME/KEY: variant
<222> LOCATION: (76)..(76)
<223> OTHER INFORMATION: S is designated as amino acid 74

<400> SEQUENCE: 1

Leu Xaa Xaa Asp Trp Gly Pro Cys Xaa Xaa His Gly Xaa His Xaa Ile
1               5                   10                  15

Arg Xaa Pro Arg Thr Pro Xaa Arg Val Xaa Gly Gly Val Phe Leu Val
            20                  25                  30

Asp Lys Asn Pro His Asn Thr Xaa Glu Ser Xaa Leu Xaa Val Asp Phe
        35                  40                  45

Ser Gln Phe Ser Arg Gly Xaa Xaa Xaa Val Ser Trp Pro Lys Phe Ala
    50                  55                  60

Val Pro Asn Leu Xaa Ser Leu Thr Asn Leu Leu Ser
65                  70                  75

<210> SEQ ID NO 2
<211> LENGTH: 181
<212> TYPE: PRT
<213> ORGANISM: artificial sequence
<220> FEATURE:
<223> OTHER INFORMATION: regions A to E of HBV DNA polymerase (Formula
      II)
<220> FEATURE:
<221> NAME/KEY: variant
<222> LOCATION: (1)..(1)
<223> OTHER INFORMATION: S = amino acid 75
<220> FEATURE:
<221> NAME/KEY: MISC_FEATURE
<222> LOCATION: (2)..(2)
<223> OTHER INFORMATION: Xaa = N or D
<220> FEATURE:
<221> NAME/KEY: MISC_FEATURE
<222> LOCATION: (17)..(17)
<223> OTHER INFORMATION: Xaa = I or P
<220> FEATURE:
<221> NAME/KEY: MISC_FEATURE
<222> LOCATION: (29)..(29)
<223> OTHER INFORMATION: Xaa = I or V
<220> FEATURE:
<221> NAME/KEY: MISC_FEATURE
<222> LOCATION: (35)..(35)
<223> OTHER INFORMATION: Xaa = S or D
<220> FEATURE:
<221> NAME/KEY: MISC_FEATURE
<222> LOCATION: (44)..(44)
<223> OTHER INFORMATION: Xaa = T or N
<220> FEATURE:
<221> NAME/KEY: MISC_FEATURE
<222> LOCATION: (46)..(46)
<223> OTHER INFORMATION: Xaa = R or N
<220> FEATURE:
<221> NAME/KEY: MISC_FEATURE
<222> LOCATION: (47)..(47)
<223> OTHER INFORMATION: Xaa = N or I
<220> FEATURE:
<221> NAME/KEY: MISC_FEATURE
<222> LOCATION: (48)..(48)
<223> OTHER INFORMATION: Xaa = any amino acid
<220> FEATURE:
<221> NAME/KEY: MISC_FEATURE
```

-continued

```
<222> LOCATION: (50)..(50)
<223> OTHER INFORMATION: Xaa = N  or Y or H
<220> FEATURE:
<221> NAME/KEY: MISC_FEATURE
<222> LOCATION: (52)..(52)
<223> OTHER INFORMATION: Xaa = H or Y
<220> FEATURE:
<221> NAME/KEY: MISC_FEATURE
<222> LOCATION: (53)..(53)
<223> OTHER INFORMATION: Xaa = G or R
<220> FEATURE:
<221> NAME/KEY: MISC_FEATURE
<222> LOCATION: (54)..(56)
<223> OTHER INFORMATION: Xaa is any amino acid
<220> FEATURE:
<221> NAME/KEY: MISC_FEATURE
<222> LOCATION: (57)..(57)
<223> OTHER INFORMATION: Xaa = D or N
<220> FEATURE:
<221> NAME/KEY: MISC_FEATURE
<222> LOCATION: (60)..(60)
<223> OTHER INFORMATION: Xaa = D or N
<220> FEATURE:
<221> NAME/KEY: MISC_FEATURE
<222> LOCATION: (61)..(61)
<223> OTHER INFORMATION: Xaa= S or Y
<220> FEATURE:
<221> NAME/KEY: MISC_FEATURE
<222> LOCATION: (65)..(65)
<223> OTHER INFORMATION: Xaa = N or Q
<220> FEATURE:
<221> NAME/KEY: MISC_FEATURE
<222> LOCATION: (71)..(71)
<223> OTHER INFORMATION: Xaa = L or M
<220> FEATURE:
<221> NAME/KEY: MISC_FEATURE
<222> LOCATION: (75)..(75)
<223> OTHER INFORMATION: Xaa = K or Q
<220> FEATURE:
<221> NAME/KEY: MISC_FEATURE
<222> LOCATION: (77)..(77)
<223> OTHER INFORMATION: Xaa = Y or F
<220> FEATURE:
<221> NAME/KEY: MISC_FEATURE
<222> LOCATION: (79)..(79)
<223> OTHER INFORMATION: Xaa = R or W
<220> FEATURE:
<221> NAME/KEY: MISC_FEATURE
<222> LOCATION: (84)..(84)
<223> OTHER INFORMATION: Xaa = Y or L
<220> FEATURE:
<221> NAME/KEY: MISC_FEATURE
<222> LOCATION: (85)..(85)
<223> OTHER INFORMATION: Xaa = S or A
<220> FEATURE:
<221> NAME/KEY: MISC_FEATURE
<222> LOCATION: (89)..(89)
<223> OTHER INFORMATION: Xaa = I or V
<220> FEATURE:
<221> NAME/KEY: MISC_FEATURE
<222> LOCATION: (95)..(95)
<223> OTHER INFORMATION: Xaa = I or L
<220> FEATURE:
<221> NAME/KEY: MISC_FEATURE
<222> LOCATION: (99)..(99)
<223> OTHER INFORMATION: Xaa = V or G
<220> FEATURE:
<221> NAME/KEY: MISC_FEATURE
<222> LOCATION: (114)..(114)
<223> OTHER INFORMATION: Xaa = C or L
<220> FEATURE:
<221> NAME/KEY: MISC_FEATURE
<222> LOCATION: (115)..(115)
<223> OTHER INFORMATION: Xaa = A or S
<220> FEATURE:
<221> NAME/KEY: MISC_FEATURE
<222> LOCATION: (116)..(116)
<223> OTHER INFORMATION: Xaa = V or M
<220> FEATURE:
<221> NAME/KEY: MISC_FEATURE
```

```
<222> LOCATION: (117)..(117)
<223> OTHER INFORMATION: Xaa = V or T
<220> FEATURE:
<221> NAME/KEY: MISC_FEATURE
<222> LOCATION: (118)..(118)
<223> OTHER INFORMATION: Xaa = R or C
<220> FEATURE:
<221> NAME/KEY: MISC_FEATURE
<222> LOCATION: (122)..(122)
<223> OTHER INFORMATION: Xaa = F or P
<220> FEATURE:
<221> NAME/KEY: MISC_FEATURE
<222> LOCATION: (125)..(125)
<223> OTHER INFORMATION: Xaa = L or V
<220> FEATURE:
<221> NAME/KEY: MISC_FEATURE
<222> LOCATION: (126)..(126)
<223> OTHER INFORMATION: Xaa = A or V
<220> FEATURE:
<221> NAME/KEY: MISC_FEATURE
<222> LOCATION: (128)..(128)
<223> OTHER INFORMATION: Xaa = S or A
<220> FEATURE:
<221> NAME/KEY: variant
<222> LOCATION: (130)..(130)
<223> OTHER INFORMATION: M = amino acid 204
<220> FEATURE:
<221> NAME/KEY: MISC_FEATURE
<222> LOCATION: (133)..(133)
<223> OTHER INFORMATION: Xaa = V or L or M
<220> FEATURE:
<221> NAME/KEY: MISC_FEATURE
<222> LOCATION: (138)..(138)
<223> OTHER INFORMATION: Xaa = K or R
<220> FEATURE:
<221> NAME/KEY: MISC_FEATURE
<222> LOCATION: (139)..(139)
<223> OTHER INFORMATION: Xaa = S or T
<220> FEATURE:
<221> NAME/KEY: MISC_FEATURE
<222> LOCATION: (140)..(140)
<223> OTHER INFORMATION: Xaa = V or G
<220> FEATURE:
<221> NAME/KEY: MISC_FEATURE
<222> LOCATION: (141)..(141)
<223> OTHER INFORMATION: Xaa = Q or E
<220> FEATURE:
<221> NAME/KEY: MISC_FEATURE
<222> LOCATION: (143)..(143)
<223> OTHER INFORMATION: Xaa = L or S or R
<220> FEATURE:
<221> NAME/KEY: MISC_FEATURE
<222> LOCATION: (145)..(145)
<223> OTHER INFORMATION: Xaa = S or F
<220> FEATURE:
<221> NAME/KEY: MISC_FEATURE
<222> LOCATION: (147)..(147)
<223> OTHER INFORMATION: Xaa = F or Y
<220> FEATURE:
<221> NAME/KEY: MISC_FEATURE
<222> LOCATION: (148)..(148)
<223> OTHER INFORMATION: Xaa = T or A
<220> FEATURE:
<221> NAME/KEY: MISC_FEATURE
<222> LOCATION: (149)..(149)
<223> OTHER INFORMATION: Xaa = A or S
<220> FEATURE:
<221> NAME/KEY: MISC_FEATURE
<222> LOCATION: (150)..(150)
<223> OTHER INFORMATION: Xaa = V or I
<220> FEATURE:
<221> NAME/KEY: MISC_FEATURE
<222> LOCATION: (151)..(151)
<223> OTHER INFORMATION: Xaa = T or C
<220> FEATURE:
<221> NAME/KEY: MISC_FEATURE
<222> LOCATION: (152)..(152)
<223> OTHER INFORMATION: Xaa = N or S
<220> FEATURE:
<221> NAME/KEY: MISC_FEATURE
```

<222> LOCATION: (153)..(153)
<223> OTHER INFORMATION: Xaa = F or V
<220> FEATURE:
<221> NAME/KEY: MISC_FEATURE
<222> LOCATION: (156)..(156)
<223> OTHER INFORMATION: Xaa = S or D
<220> FEATURE:
<221> NAME/KEY: MISC_FEATURE
<222> LOCATION: (157)..(157)
<223> OTHER INFORMATION: Xaa = L or V
<220> FEATURE:
<221> NAME/KEY: MISC_FEATURE
<222> LOCATION: (164)..(164)
<223> OTHER INFORMATION: Xaa = N or Q
<220> FEATURE:
<221> NAME/KEY: MISC_FEATURE
<222> LOCATION: (179)..(179)
<223> OTHER INFORMATION: Xaa = V or I

<400> SEQUENCE: 2

Ser Xaa Leu Ser Trp Leu Ser Leu Asp Val Ser Ala Ala Phe Tyr His
 1               5                  10                  15

Xaa Pro Leu His Pro Ala Ala Met Pro His Leu Leu Xaa Gly Ser Ser
             20                  25                  30

Gly Leu Xaa Arg Tyr Val Ala Arg Leu Ser Ser Xaa Ser Xaa Xaa Xaa
         35                  40                  45

Asn Xaa Gln Xaa Xaa Xaa Xaa Xaa Xaa Leu His Xaa Xaa Cys Ser Arg
 50                  55                  60

Xaa Leu Tyr Val Ser Leu Xaa Leu Leu Tyr Xaa Thr Xaa Gly Xaa Lys
65                  70                  75                  80

Leu His Leu Xaa Xaa His Pro Ile Xaa Leu Gly Phe Arg Lys Xaa Pro
                 85                  90                  95

Met Gly Xaa Gly Leu Ser Pro Phe Leu Leu Ala Gln Phe Thr Ser Ala
            100                 105                 110

Ile Xaa Xaa Xaa Xaa Xaa Arg Ala Phe Xaa His Cys Xaa Xaa Phe Xaa
    115                 120                 125

Tyr Met Asp Asp Xaa Val Leu Gly Ala Xaa Xaa Xaa His Xaa Glu
130                 135                 140

Xaa Leu Xaa Xaa Xaa Xaa Xaa Xaa Leu Leu Xaa Xaa Gly Ile His
145                 150                 155                 160

Leu Asn Pro Xaa Lys Thr Lys Arg Trp Gly Tyr Ser Leu Asn Phe Met
                165                 170                 175

Gly Tyr Xaa Ile Gly
            180

<210> SEQ ID NO 3
<211> LENGTH: 23
<212> TYPE: DNA
<213> ORGANISM: artificial sequence
<220> FEATURE:
<223> OTHER INFORMATION: primer (OS1)

<400> SEQUENCE: 3
gcctcatttt gtgggtcacc ata                                    23

<210> SEQ ID NO 4
<211> LENGTH: 18
<212> TYPE: DNA
<213> ORGANISM: artificial sequence
<220> FEATURE:
<223> OTHER INFORMATION: primer (TTA3)

<400> SEQUENCE: 4
aaattcgcag tccccaaa                                          18

<210> SEQ ID NO 5
<211> LENGTH: 21
<212> TYPE: DNA
<213> ORGANISM: artificial sequence
<220> FEATURE:
<223> OTHER INFORMATION: primer (JM)

<400> SEQUENCE: 5
ttggggtgga gccctcaggc t                                             21

<210> SEQ ID NO 6
<211> LENGTH: 18
<212> TYPE: DNA
<213> ORGANISM: artificial sequence
<220> FEATURE:
<223> OTHER INFORMATION: primer (TTA4)

<400> SEQUENCE: 6
gaaaattggt aacagcgg                                                 18

<210> SEQ ID NO 7
<211> LENGTH: 20
<212> TYPE: DNA
<213> ORGANISM: artificial sequence
<220> FEATURE:
<223> OTHER INFORMATION: primer (OS2)

<400> SEQUENCE: 7
tctctgacat actttccaat                                               20

<210> SEQ ID NO 8
<211> LENGTH: 18
<212> TYPE: DNA
<213> ORGANISM: artificial sequence
<220> FEATURE:
<223> OTHER INFORMATION: primer

<400> SEQUENCE: 8
tgcacgattc ctgctcaa                                                 18

<210> SEQ ID NO 9
<211> LENGTH: 21
<212> TYPE: DNA
<213> ORGANISM: artificial sequence
<220> FEATURE:
<223> OTHER INFORMATION: primer

<400> SEQUENCE: 9
ttggggtgga gccctcaggc t                                             21

<210> SEQ ID NO 10
<211> LENGTH: 18
<212> TYPE: DNA
<213> ORGANISM: artificial sequence
<220> FEATURE:
<223> OTHER INFORMATION: forward primer PC1

<400> SEQUENCE: 10
gggaggagat taggttaa                                                 18

<210> SEQ ID NO 11
<211> LENGTH: 20
<212> TYPE: DNA
<213> ORGANISM: artificial sequence
<220> FEATURE:
<223> OTHER INFORMATION: reverse primer PC2

<400> SEQUENCE: 11
ggcaaaaacg agagtaactc                                                    20

<210> SEQ ID NO 12
<211> LENGTH: 42
<212> TYPE: DNA
<213> ORGANISM: artificial sequence
<220> FEATURE:
<223> OTHER INFORMATION: HBV-specific molecule beacon primer
<220> FEATURE:
<221> NAME/KEY: misc_feature
<222> LOCATION: (42)..(42)
<223> OTHER INFORMATION: N = L

<400> SEQUENCE: 12
cgcgtcctac tgttcaagcc tccaagctgt gacgcgdabc yn                            42

<210> SEQ ID NO 13
<211> LENGTH: 644
<212> TYPE: DNA
<213> ORGANISM: artificial sequence
<220> FEATURE:
<223> OTHER INFORMATION: TR2
<220> FEATURE:
<221> NAME/KEY: misc_feature
<222> LOCATION: (619)..(620)
<223> OTHER INFORMATION: N = any nucleotide
<220> FEATURE:
<221> NAME/KEY: misc_feature
<222> LOCATION: (624)..(624)
<223> OTHER INFORMATION: N = any nucleotide
<220> FEATURE:
<221> NAME/KEY: misc_feature
<222> LOCATION: (631)..(631)
<223> OTHER INFORMATION: N = any nucleotide

<400> SEQUENCE: 13
ccctcccgtt ctccaacttg tcctggttat cgctggatgt gtctgcggcg ttttatcata        60
ttcctcttca tcctgctgct atgcctcatc ttcttgttgg ttcttctgga ctatcaaggt       120
atgttgcccg tctgtcctct aattccagga tcttcaacca ccagcgcggg accatgcaga       180
acctgcacga ctactgctca aggaacctct atgtatccct cctgttgctg taccaaacct       240
tcggacggaa attgcacctg tattcccatc ccatcatctt gggctttcgg aaaattccta       300
tgggagtggg cctcagcccg tttctcatgg ctcagtttac tagygccatt tgttcagtgg       360
ttcgtagggc tttcccccac tgtttggctt ttagttatrt ggatgatgtg gtattggggg       420
ccaagtctgt acagcacctt gagtcccttt ttaccgctgt taccaatttt cttttgtctt       480
tgggtataca tttaaacccct aacaaaacta aaagatgggg ttattcctta aatttcatgg       540
gctatgtcat tggatgttat gggtcattgc cacaagatca catcatacag aaaatcaaag       600
aatgttttag gaaacttcnn gtgngcggga ntggaacaga tcca                        644

<210> SEQ ID NO 14
<211> LENGTH: 593
<212> TYPE: DNA
<213> ORGANISM: artificial sequence
<220> FEATURE:
<223> OTHER INFORMATION: TR3

<400> SEQUENCE: 14
ctgtcctcca acttgtcctg gttatcgctg gatgtgtctg cggcgtttta tcatattcct        60
cttcatcctg ctgctatgcc tcatcttctt gttggttctt ctggactatc aaggtatgtt       120
gcccgtctgt cctctaattc caggatcttc aaccaccagc gcgggaccat gcagaacctg       180

```
cacgactact gctcaaggaa cctctatgta tccctcctgt tgctgtacca aaccttcgga    240
cggaaattgc acctgtattc ccatcccatc atcttgggct ttcggaaaat tcctatggga    300
gtgggcctca gcccgtttct catggctcag tttactagyg ccatttgttc agtggttcgt    360
agggctttcc cccactgttt ggctttcagt tatgtggatg atgtggtatt gggggccaag    420
tctgtacagc accttgagtc cctttttacc gctgttacca attttctttt gtctttgggt    480
atacatttaa accctaacaa aactaaaaga tggggttatt ccttaaattt catgggctat    540
gtcattggat gttatgggtc attgccacaa gatcacatca tacagaaaat caa           593
```

```
<210> SEQ ID NO 15
<211> LENGTH: 605
<212> TYPE: DNA
<213> ORGANISM: artificial sequence
<220> FEATURE:
<223> OTHER INFORMATION: TR3

<400> SEQUENCE: 15
ctgtcctcca acttgtcctg gttatcgctg gatgtgtctg cggcgtttta tcatattcct     60
cttcatcctg ctgctatgcc tcatcttctt gttggttctt ctggactatc aaggtatgtt    120
gcccgtctgt cctctaattc aggatcttca accaccagc gcgggaccat gcagaacctg    180
cacgactact gctcaaggaa cctctatgta tccctcctgt tgctgtacca aaccttcgga    240
cggaaattgc acctgtattc ccatcccatc atcttgggct ttcggaaaat tcctatggga    300
gtgggcctca gcccgtttct catggctcag tttactagtg ccatttgttc agtggttcgt    360
agggctttcc cccactgttt ggctttyagt tatgtggatg atgtggtatt gggggccaag    420
tctgtacagc accttgagtc cctttttacc gctgttacca attttctttt gtctttgggt    480
atacatttaa accctaacaa aactaaaaga tggggttatt ccttaaattt catgggctat    540
gtcattggat gttatgggtc attgccacaa gatcacatca tacagaaaat caaagaatgt    600
tttag                                                                605
```

```
<210> SEQ ID NO 16
<211> LENGTH: 614
<212> TYPE: DNA
<213> ORGANISM: artificial sequence
<220> FEATURE:
<223> OTHER INFORMATION: TR4

<400> SEQUENCE: 16
gtcctccaac ttgtcctggt tatcgctgga tgtgtctgcg gcgttttatc atattcctct     60
tcatcctgct gctatgcctc atcttcttgt tggttcttct ggactatcaa ggtatgttgc    120
ccgtctgtcc tctaattcca ggatcttcaa ccaccagcgc gggaccatgc agaacctgca    180
cgactactgc tcaaggaacc tctatgtatc cctcctgttg ctgtaccaaa ccttcggacg    240
gaaattgcac ctgtattccc atcccatcat cttgggcttt cggaaaattc ctatgggagt    300
gggcctcagc ccgtttctca tggctcagtt tactagtgcc atttgttcag tggttcgtag    360
ggctttcccc cactgtttgg ctttcagtta tgtggatgat gtggtattgg gggccaagtc    420
tgtacagcac cttgagtccc tttttaccgc tgttaccaat tttcttttgt ctttgggtat    480
acatttaaac cctaacaaaa ctaaaagatg ggttattcc ttaaatttca tgggctatgt    540
cattggatgt tatgggtcat tgccacaaga tcacatcata cagaaaatca agaatgtttt    600
taggaaactt cctg                                                       614
```

```
<210> SEQ ID NO 17
<211> LENGTH: 607
<212> TYPE: DNA
<213> ORGANISM: artificial sequence
<220> FEATURE:
<223> OTHER INFORMATION: TR5

<400> SEQUENCE: 17
gtcctccaac ttgtcctggt tatcgctgga tgtgtctgcg gcgttttatc atattcctct      60
tcatcctgct gctatgcctc atcttcttgt tggttcttct ggactatcaa ggtatgttgc     120
ccgtctgtcc tctaattcca ggatcttcaa ccaccagcgc gggaccatgc agaacctgca     180
cgactactgc tcaaggaacc tctatgtatc cctcctgttg ctgtaccaaa ccttcggacg     240
gaaattgcac ctgtattccc atcccatcat cttgggcttt cggaaaattc ctatgggakt     300
gggcctcagc ccgtttctca tggctcagtt tactagtgcc atttgttcag tggttcgtag     360
ggctttcccc cactgtttgg ctttcagtta tgtggatgat gtggtattgg gggccaagtc     420
tgtacagcac cttgagtccc tttttaccgc tgttaccaat tttctttttgt ctttgggtat    480 acatttaaac cctaacaaaa ctaaaagatg gggttattcc ttaaatttca tgggctatgt     540
cattggatgt tatgggtcat tgccacaaga tcacatcata cagaaaatca agaatgtttt    600
taggaaa                                                              607

<210> SEQ ID NO 18
<211> LENGTH: 1028
<212> TYPE: DNA
<213> ORGANISM: artificial sequence
<220> FEATURE:
<223> OTHER INFORMATION: TR6
<220> FEATURE:
<221> NAME/KEY: misc_feature
<222> LOCATION: (12)..(12)
<223> OTHER INFORMATION: N = any nucleotide
<220> FEATURE:
<221> NAME/KEY: misc_feature
<222> LOCATION: (27)..(27)
<223> OTHER INFORMATION: N = any nucleotide

<400> SEQUENCE: 18
gggggccgca gncagataca aaccttngcc aggaatcctc cttcctgcat ctaccaatcg      60
ccagtcagga aggcagccta ccccgctgtc tccacctttg agagactctc atcctcaggc     120
catgcagtgg aactccacaa cttttccacca aactctgcaa gatcccaggg tgagggcct    180 gtatctccct gctggtggct ccagttcagg aacagtaaac cctgttccga ctactgcctc     240
tcccatatcg tcaatcttct cgaggattgg ggaccttgcg ctgaacatgg agaacatcac     300
atcaggattc ctaggacccc tgctcgtgtt acaggcgggg ttttttcttgt tgacaagaat    360 cctcacaata ccgcagagtc tagactcgtg gtggacttct ctcaattttc tagggggaac    420
caccgtgtgt cttggccaaa attcgcagtc cccaacctcc aatcactcac caacctcctg    480
tcctccaact tgtcctggtt atcgctggat gtgtctgcgg cgttttatca tattcctctt     540
catcctgctg statgcctca tcttcttgtt ggttcttctg gactatcaag gtatgttgcc     600
cgtctgtcct ctaattccag gatcttcaac caccagcgcg ggaccatgca gaacctgcac     660
gactactgct caaggaacct ctatgtatcc ctcctgttgc tgtaccaaac cttcggacgg     720
aaattgcacc tgtattccca tcccatcatc ttgggctttc ggaaaactcc tatgggattg    780
ggcctcagcc cgtttctcat ggctcagttt actagtgcca tttgttcagt ggttcgtagg    840
gctttccccc actgtttggc tttcagttat gtggatgatg tggtattggg ggccaagtct    900
gtacagcacc ttgagtccct ttttaccgct gttaccaatt ttcttttgtc tttgggtata    960
```

```
catttaaacc ctaacaaaac taaagatgg ggttattcct taaatttcgt gggctatgtc    1020
attggatg                                                            1028
```

<210> SEQ ID NO 19
<211> LENGTH: 181
<212> TYPE: PRT
<213> ORGANISM: artificial sequence
<220> FEATURE:
<223> OTHER INFORMATION: Pol Trans of TR1
<220> FEATURE:
<221> NAME/KEY: misc_feature
<222> LOCATION: (130)..(130)
<223> OTHER INFORMATION: Xaa = any amino acid

<400> SEQUENCE: 19

```
Ser Asn Leu Ser Trp Leu Ser Leu Asp Val Ser Ala Ala Phe Tyr His
1               5                   10                  15

Ile Pro Leu His Pro Ala Ala Met Pro His Leu Leu Val Gly Ser Ser
            20                  25                  30

Gly Leu Ser Arg Tyr Val Ala Arg Leu Ser Ser Asn Ser Arg Ile Phe
        35                  40                  45

Asn His Gln Arg Gly Thr Met Gln Asn Leu His Asp Tyr Cys Ser Arg
    50                  55                  60

Asn Leu Tyr Val Ser Leu Leu Leu Tyr Gln Thr Phe Gly Arg Lys
65                  70                  75                  80

Leu His Leu Tyr Ser His Pro Ile Ile Leu Gly Phe Arg Lys Ile Pro
                85                  90                  95

Met Gly Val Gly Leu Ser Pro Phe Leu Met Ala Gln Phe Thr Ser Ala
            100                 105                 110

Ile Cys Ser Val Val Arg Arg Ala Phe Pro His Cys Leu Ala Phe Ser
        115                 120                 125

Tyr Xaa Asp Asp Val Val Leu Gly Ala Lys Ser Val Gln His Leu Glu
    130                 135                 140

Ser Leu Phe Thr Ala Val Thr Asn Phe Leu Leu Ser Leu Gly Ile His
145                 150                 155                 160

Leu Asn Pro Asn Lys Thr Lys Arg Trp Gly Tyr Ser Leu Asn Phe Met
                165                 170                 175

Gly Tyr Val Ile Gly
            180
```

<210> SEQ ID NO 20
<211> LENGTH: 187
<212> TYPE: PRT
<213> ORGANISM: artificial sequence
<220> FEATURE:
<223> OTHER INFORMATION: Pol Trans of TR2

<400> SEQUENCE: 20

```
Leu Ser Ser Asn Leu Ser Trp Leu Ser Leu Asp Val Ser Ala Ala Phe
1               5                   10                  15

Tyr His Ile Pro Leu His Pro Ala Ala Met Pro His Leu Leu Val Gly
            20                  25                  30

Ser Ser Gly Leu Ser Arg Tyr Val Ala Arg Leu Ser Ser Asn Ser Arg
        35                  40                  45

Ile Phe Asn His Gln Arg Gly Thr Met Gln Asn Leu His Asp Tyr Cys
    50                  55                  60

Ser Arg Asn Leu Tyr Val Ser Leu Leu Leu Leu Tyr Gln Thr Phe Gly
65                  70                  75                  80
```

-continued

```
Arg Lys Leu His Leu Tyr Ser His Pro Ile Ile Leu Gly Phe Arg Lys
            85                  90                  95
Ile Pro Met Gly Val Gly Leu Ser Pro Phe Leu Met Ala Gln Phe Thr
            100                 105                 110
Ser Ala Ile Cys Ser Val Val Arg Arg Ala Phe Pro His Cys Leu Ala
            115                 120                 125
Phe Ser Tyr Val Asp Asp Val Val Leu Gly Ala Lys Ser Val Gln His
        130                 135                 140
Leu Glu Ser Leu Phe Thr Ala Val Thr Asn Phe Leu Ser Leu Gly
145                 150                 155                 160
Ile His Leu Asn Pro Asn Lys Thr Lys Arg Trp Gly Tyr Ser Leu Asn
                165                 170                 175
Phe Met Gly Tyr Val Ile Gly Cys Tyr Gly Ser
            180                 185
```

<210> SEQ ID NO 21
<211> LENGTH: 185
<212> TYPE: PRT
<213> ORGANISM: artificial sequence
<220> FEATURE:
<223> OTHER INFORMATION: Pol Trans of TR3

<400> SEQUENCE: 21

```
Leu Ser Ser Asn Leu Ser Trp Leu Ser Leu Asp Val Ser Ala Ala Phe
1               5                   10                  15
Tyr His Ile Pro Leu His Pro Ala Ala Met Pro His Leu Leu Val Gly
            20                  25                  30
Ser Ser Gly Leu Ser Arg Tyr Val Ala Arg Leu Ser Ser Asn Ser Arg
        35                  40                  45
Ile Phe Asn His Gln Arg Gly Thr Met Gln Asn Leu His Asp Tyr Cys
    50                  55                  60
Ser Arg Asn Leu Tyr Val Ser Leu Leu Leu Leu Tyr Gln Thr Phe Gly
65                  70                  75                  80
Arg Lys Leu His Leu Tyr Ser His Pro Ile Ile Leu Gly Phe Arg Lys
                85                  90                  95
Ile Pro Met Gly Val Gly Leu Ser Pro Phe Leu Met Ala Gln Phe Thr
            100                 105                 110
Ser Ala Ile Cys Ser Val Val Arg Arg Ala Phe Pro His Cys Leu Ala
        115                 120                 125
Phe Ser Tyr Val Asp Asp Val Val Leu Gly Ala Lys Ser Val Gln His
    130                 135                 140
Leu Glu Ser Leu Phe Thr Ala Val Thr Asn Phe Leu Ser Leu Gly
145                 150                 155                 160
Ile His Leu Asn Pro Asn Lys Thr Lys Arg Trp Gly Tyr Ser Leu Asn
                165                 170                 175
Phe Met Gly Tyr Val Ile Gly Cys Tyr
            180                 185
```

<210> SEQ ID NO 22
<211> LENGTH: 184
<212> TYPE: PRT
<213> ORGANISM: artificial sequence
<220> FEATURE:
<223> OTHER INFORMATION: Pol Trans of TR4

<400> SEQUENCE: 22

```
Ser Ser Asn Leu Ser Trp Leu Ser Leu Asp Val Ser Ala Ala Phe Tyr
1               5                   10                  15
```

His Ile Pro Leu His Pro Ala Ala Met Pro His Leu Leu Val Gly Ser
            20                  25                  30

Ser Gly Leu Ser Arg Tyr Val Ala Arg Leu Ser Ser Asn Ser Arg Ile
        35                  40                  45

Phe Asn His Gln Arg Gly Thr Met Gln Asn Leu His Asp Tyr Cys Ser
    50                  55                  60

Arg Asn Leu Tyr Val Ser Leu Leu Leu Tyr Gln Thr Phe Gly Arg
65                  70                  75                  80

Lys Leu His Leu Tyr Ser His Pro Ile Ile Leu Gly Phe Arg Lys Ile
                85                  90                  95

Pro Met Gly Val Gly Leu Ser Pro Phe Leu Met Ala Gln Phe Thr Ser
            100                 105                 110

Ala Ile Cys Ser Val Val Arg Arg Ala Phe Pro His Cys Leu Ala Phe
        115                 120                 125

Ser Tyr Val Asp Asp Val Val Leu Gly Ala Lys Ser Val Gln His Leu
    130                 135                 140

Glu Ser Leu Phe Thr Ala Val Thr Asn Phe Leu Leu Ser Leu Gly Ile
145                 150                 155                 160

His Leu Asn Pro Asn Lys Thr Lys Arg Trp Gly Tyr Ser Leu Asn Phe
                165                 170                 175

Met Gly Tyr Val Ile Gly Cys Tyr
            180

<210> SEQ ID NO 23
<211> LENGTH: 184
<212> TYPE: PRT
<213> ORGANISM: artificial sequence
<220> FEATURE:
<223> OTHER INFORMATION: Pol Trans of TR5
<220> FEATURE:
<221> NAME/KEY: misc_feature
<222> LOCATION: (100)..(100)
<223> OTHER INFORMATION: Xaa = any amino acid

<400> SEQUENCE: 23

Ser Ser Asn Leu Ser Trp Leu Ser Leu Asp Val Ser Ala Ala Phe Tyr
1               5                   10                  15

His Ile Pro Leu His Pro Ala Ala Met Pro His Leu Leu Val Gly Ser
            20                  25                  30

Ser Gly Leu Ser Arg Tyr Val Ala Arg Leu Ser Ser Asn Ser Arg Ile
        35                  40                  45

Phe Asn His Gln Arg Gly Thr Met Gln Asn Leu His Asp Tyr Cys Ser
    50                  55                  60

Arg Asn Leu Tyr Val Ser Leu Leu Leu Tyr Gln Thr Phe Gly Arg
65                  70                  75                  80

Lys Leu His Leu Tyr Ser His Pro Ile Ile Leu Gly Phe Arg Lys Ile
                85                  90                  95

Pro Met Gly Xaa Gly Leu Ser Pro Phe Leu Met Ala Gln Phe Thr Ser
            100                 105                 110

Ala Ile Cys Ser Val Val Arg Arg Ala Phe Pro His Cys Leu Ala Phe
        115                 120                 125

Ser Tyr Val Asp Asp Val Val Leu Gly Ala Lys Ser Val Gln His Leu
    130                 135                 140

Glu Ser Leu Phe Thr Ala Val Thr Asn Phe Leu Leu Ser Leu Gly Ile
145                 150                 155                 160

His Leu Asn Pro Asn Lys Thr Lys Arg Trp Gly Tyr Ser Leu Asn Phe
                165                 170                 175

```
Met Gly Tyr Val Ile Gly Cys Tyr
            180
```

<210> SEQ ID NO 24
<211> LENGTH: 326
<212> TYPE: PRT
<213> ORGANISM: artificial sequence
<220> FEATURE:
<223> OTHER INFORMATION: Pol Trans of TR6
<220> FEATURE:
<221> NAME/KEY: misc_feature
<222> LOCATION: (168)..(168)
<223> OTHER INFORMATION: Xaa = any amino acid

<400> SEQUENCE: 24

```
Ile Tyr Gln Ser Pro Val Arg Lys Ala Ala Tyr Pro Ala Val Ser Thr
1               5                   10                  15

Phe Glu Arg Leu Ser Ser Ser Gly His Ala Val Glu Leu His Asn Phe
            20                  25                  30

Pro Pro Asn Ser Ala Arg Ser Gln Gly Glu Gly Pro Val Ser Pro Cys
        35                  40                  45

Trp Trp Leu Gln Phe Arg Asn Ser Lys Pro Cys Ser Asp Tyr Cys Leu
    50                  55                  60

Ser His Ile Val Asn Leu Leu Glu Asp Trp Gly Pro Cys Ala Glu His
65                  70                  75                  80

Gly Glu His His Ile Arg Ile Pro Arg Thr Pro Ala Arg Val Thr Gly
                85                  90                  95

Gly Val Phe Leu Val Asp Lys Asn Pro His Asn Thr Ala Glu Ser Arg
            100                 105                 110

Leu Val Val Asp Phe Ser Gln Phe Ser Arg Gly Asn His Arg Val Ser
        115                 120                 125

Trp Pro Lys Phe Ala Val Pro Asn Leu Gln Ser Leu Thr Asn Leu Leu
    130                 135                 140

Ser Ser Asn Leu Ser Trp Leu Ser Leu Asp Val Ser Ala Ala Phe Tyr
145                 150                 155                 160

His Ile Pro Leu His Pro Ala Xaa Met Pro His Leu Leu Val Gly Ser
                165                 170                 175

Ser Gly Leu Ser Arg Tyr Val Ala Arg Leu Ser Ser Asn Ser Arg Ile
            180                 185                 190

Phe Asn His Gln Arg Gly Thr Met Gln Asn Leu His Asp Tyr Cys Ser
        195                 200                 205

Arg Asn Leu Tyr Val Ser Leu Leu Leu Leu Tyr Gln Thr Phe Gly Arg
    210                 215                 220

Lys Leu His Leu Tyr Ser His Pro Ile Ile Leu Gly Phe Arg Lys Thr
225                 230                 235                 240

Pro Met Gly Leu Gly Leu Ser Pro Phe Leu Met Ala Gln Phe Thr Ser
                245                 250                 255

Ala Ile Cys Ser Val Val Arg Arg Ala Phe Pro His Cys Leu Ala Phe
            260                 265                 270

Ser Tyr Val Asp Asp Val Val Leu Gly Ala Lys Ser Val Gln His Leu
        275                 280                 285

Glu Ser Leu Phe Thr Ala Val Thr Asn Phe Leu Leu Ser Leu Gly Ile
    290                 295                 300

His Leu Asn Pro Asn Lys Thr Lys Arg Trp Gly Tyr Ser Leu Asn Phe
305                 310                 315                 320

Val Gly Tyr Val Ile Gly
                325
```

```
<210> SEQ ID NO 25
<211> LENGTH: 161
<212> TYPE: PRT
<213> ORGANISM: artificial sequence
<220> FEATURE:
<223> OTHER INFORMATION: HBsAg Trans of TR1
<220> FEATURE:
<221> NAME/KEY: misc_feature
<222> LOCATION: (111)..(111)
<223> OTHER INFORMATION: Xaa = any amino acid
<220> FEATURE:
<221> NAME/KEY: misc_feature
<222> LOCATION: (129)..(129)
<223> OTHER INFORMATION: Xaa = any amino acid

<400> SEQUENCE: 25

Pro Thr Cys Pro Gly Tyr Arg Trp Met Cys Leu Arg Arg Phe Ile Ile
1               5                   10                  15

Phe Leu Phe Ile Leu Leu Leu Cys Leu Ile Phe Leu Leu Val Leu Leu
                20                  25                  30

Asp Tyr Gln Gly Met Leu Pro Val Cys Pro Leu Ile Pro Gly Ser Ser
            35                  40                  45

Thr Thr Ser Ala Gly Pro Cys Arg Thr Cys Thr Thr Thr Ala Gln Gly
    50                  55                  60

Thr Ser Met Tyr Pro Ser Cys Cys Cys Thr Lys Pro Ser Asp Gly Asn
65                  70                  75                  80

Cys Thr Cys Ile Pro Ile Pro Ser Ser Trp Ala Phe Gly Lys Phe Leu
                85                  90                  95

Trp Glu Trp Ala Ser Ala Arg Phe Ser Trp Leu Ser Leu Leu Xaa Pro
            100                 105                 110

Phe Val Gln Trp Phe Val Gly Leu Ser Pro Thr Val Trp Leu Leu Val
        115                 120                 125

Xaa Trp Met Met Trp Tyr Trp Gly Pro Ser Leu Tyr Ser Thr Leu Ser
    130                 135                 140

Pro Phe Leu Pro Leu Leu Pro Ile Phe Phe Cys Leu Trp Val Tyr Ile
145                 150                 155                 160

Asn

<210> SEQ ID NO 26
<211> LENGTH: 162
<212> TYPE: PRT
<213> ORGANISM: artificial sequence
<220> FEATURE:
<223> OTHER INFORMATION: HBsAg Trans of TR2
<220> FEATURE:
<221> NAME/KEY: misc_feature
<222> LOCATION: (113)..(113)
<223> OTHER INFORMATION: Xaa = any amino acid

<400> SEQUENCE: 26

Cys Pro Pro Thr Cys Pro Gly Tyr Arg Trp Met Cys Leu Arg Arg Phe
1               5                   10                  15

Ile Ile Phe Leu Phe Ile Leu Leu Leu Cys Leu Ile Phe Leu Leu Val
                20                  25                  30

Leu Leu Asp Tyr Gln Gly Met Leu Pro Val Cys Pro Leu Ile Pro Gly
            35                  40                  45

Ser Ser Thr Thr Ser Ala Gly Pro Cys Arg Thr Cys Thr Thr Thr Ala
    50                  55                  60

Gln Gly Thr Ser Met Tyr Pro Ser Cys Cys Cys Thr Lys Pro Ser Asp
65                  70                  75                  80

Gly Asn Cys Thr Cys Ile Pro Ile Pro Ser Ser Trp Ala Phe Gly Lys
```

```
                    85                  90                  95
Phe Leu Trp Glu Trp Ala Ser Ala Arg Phe Ser Trp Leu Ser Leu Leu
                100                 105                 110

Xaa Pro Phe Val Gln Trp Phe Val Gly Leu Ser Pro Thr Val Trp Leu
                115                 120                 125

Ser Val Met Trp Met Met Trp Tyr Trp Gly Pro Ser Leu Tyr Ser Thr
            130                 135                 140

Leu Ser Pro Phe Leu Pro Leu Leu Pro Ile Phe Phe Cys Leu Trp Val
145                 150                 155                 160

Tyr Ile

<210> SEQ ID NO 27
<211> LENGTH: 162
<212> TYPE: PRT
<213> ORGANISM: artificial sequence
<220> FEATURE:
<223> OTHER INFORMATION: HBsAg Trans of TR3
<220> FEATURE:
<221> NAME/KEY: misc_feature
<222> LOCATION: (129)..(129)
<223> OTHER INFORMATION: Xaa = any amino acid

<400> SEQUENCE: 27

Cys Pro Pro Thr Cys Pro Gly Tyr Arg Trp Met Cys Leu Arg Arg Phe
1               5                   10                  15

Ile Ile Phe Leu Phe Ile Leu Leu Cys Leu Ile Phe Leu Leu Val
            20                  25                  30

Leu Leu Asp Tyr Gln Gly Met Leu Pro Val Cys Pro Leu Ile Pro Gly
        35                  40                  45

Ser Ser Thr Thr Ser Ala Gly Pro Cys Arg Thr Cys Thr Thr Thr Ala
    50                  55                  60

Gln Gly Thr Ser Met Tyr Pro Ser Cys Cys Thr Lys Pro Ser Asp
65                  70                  75                  80

Gly Asn Cys Thr Cys Ile Pro Ile Pro Ser Ser Trp Ala Phe Gly Lys
                85                  90                  95

Phe Leu Trp Glu Trp Ala Ser Ala Arg Phe Ser Trp Leu Ser Leu Leu
                100                 105                 110

Val Pro Phe Val Gln Trp Phe Val Gly Leu Ser Pro Thr Val Trp Leu
                115                 120                 125

Xaa Val Met Trp Met Met Trp Tyr Trp Gly Pro Ser Leu Tyr Ser Thr
            130                 135                 140

Leu Ser Pro Phe Leu Pro Leu Leu Pro Ile Phe Phe Cys Leu Trp Val
145                 150                 155                 160

Tyr Ile

<210> SEQ ID NO 28
<211> LENGTH: 161
<212> TYPE: PRT
<213> ORGANISM: artificial sequence
<220> FEATURE:
<223> OTHER INFORMATION: HBsAg Trans of TR4

<400> SEQUENCE: 28

Pro Pro Thr Cys Pro Gly Tyr Arg Trp Met Cys Leu Arg Arg Phe Ile
1               5                   10                  15

Ile Phe Leu Phe Ile Leu Leu Leu Cys Leu Ile Phe Leu Leu Val Leu
            20                  25                  30

Leu Asp Tyr Gln Gly Met Leu Pro Val Cys Pro Leu Ile Pro Gly Ser
        35                  40                  45
```

Ser Thr Thr Ser Ala Gly Pro Cys Arg Thr Cys Thr Thr Thr Ala Gln
            50                  55                  60

Gly Thr Ser Met Tyr Pro Ser Cys Cys Cys Thr Lys Pro Ser Asp Gly
 65                  70                  75                  80

Asn Cys Thr Cys Ile Pro Ile Pro Ser Ser Trp Ala Phe Gly Lys Phe
                 85                  90                  95

Leu Trp Glu Trp Ala Ser Ala Arg Phe Ser Trp Leu Ser Leu Leu Val
            100                 105                 110

Pro Phe Val Gln Trp Phe Val Gly Leu Ser Pro Thr Val Trp Leu Ser
            115                 120                 125

Val Met Trp Met Met Trp Tyr Trp Gly Pro Ser Leu Tyr Ser Thr Leu
            130                 135                 140

Ser Pro Phe Leu Pro Leu Leu Pro Ile Phe Phe Cys Leu Trp Val Tyr
145                 150                 155                 160

Ile

<210> SEQ ID NO 29
<211> LENGTH: 161
<212> TYPE: PRT
<213> ORGANISM: artificial sequence
<220> FEATURE:
<223> OTHER INFORMATION: HBsAg Trans of TR5
<220> FEATURE:
<221> NAME/KEY: misc_feature
<222> LOCATION: (99)..(99)
<223> OTHER INFORMATION: Xaa = any amino acid

<400> SEQUENCE: 29

Pro Pro Thr Cys Pro Gly Tyr Arg Trp Met Cys Leu Arg Arg Phe Ile
 1               5                  10                  15

Ile Phe Leu Phe Ile Leu Leu Leu Cys Leu Ile Phe Leu Leu Val Leu
                20                  25                  30

Leu Asp Tyr Gln Gly Met Leu Pro Val Cys Pro Leu Ile Pro Gly Ser
            35                  40                  45

Ser Thr Thr Ser Ala Gly Pro Cys Arg Thr Cys Thr Thr Thr Ala Gln
            50                  55                  60

Gly Thr Ser Met Tyr Pro Ser Cys Cys Cys Thr Lys Pro Ser Asp Gly
 65                  70                  75                  80

Asn Cys Thr Cys Ile Pro Ile Pro Ser Ser Trp Ala Phe Gly Lys Phe
                 85                  90                  95

Leu Trp Xaa Trp Ala Ser Ala Arg Phe Ser Trp Leu Ser Leu Leu Val
            100                 105                 110

Pro Phe Val Gln Trp Phe Val Gly Leu Ser Pro Thr Val Trp Leu Ser
            115                 120                 125

Val Met Trp Met Met Trp Tyr Trp Gly Pro Ser Leu Tyr Ser Thr Leu
            130                 135                 140

Ser Pro Phe Leu Pro Leu Leu Pro Ile Phe Phe Cys Leu Trp Val Tyr
145                 150                 155                 160

Ile

<210> SEQ ID NO 30
<211> LENGTH: 305
<212> TYPE: PRT
<213> ORGANISM: artificial sequence
<220> FEATURE:
<223> OTHER INFORMATION: HBsAg Trans of TR6
<220> FEATURE:
<221> NAME/KEY: misc_feature
<222> LOCATION: (168)..(168)

<223> OTHER INFORMATION: Xaa = any amino acid

<400> SEQUENCE: 30

Ser Thr Asn Arg Gln Ser Gly Arg Gln Pro Thr Pro Leu Ser Pro Pro
1               5                   10                  15
Leu Arg Asp Ser His Pro Gln Ala Met Gln Trp Asn Ser Thr Thr Phe
            20                  25                  30
His Gln Thr Leu Gln Asp Pro Arg Val Arg Gly Leu Tyr Leu Pro Ala
        35                  40                  45
Gly Gly Ser Ser Ser Gly Thr Val Asn Pro Val Pro Thr Thr Ala Ser
50                  55                  60
Pro Ile Ser Ser Ile Phe Ser Arg Ile Gly Asp Leu Ala Leu Asn Met
65                  70                  75                  80
Glu Asn Ile Thr Ser Gly Phe Leu Gly Pro Leu Leu Val Leu Gln Ala
                85                  90                  95
Gly Phe Phe Leu Leu Thr Arg Ile Leu Thr Ile Pro Gln Ser Leu Asp
            100                 105                 110
Ser Trp Trp Thr Ser Leu Asn Phe Leu Gly Gly Thr Thr Val Cys Leu
        115                 120                 125
Gly Gln Asn Ser Gln Ser Pro Thr Ser Asn His Ser Pro Thr Ser Cys
130                 135                 140
Pro Pro Thr Cys Pro Gly Tyr Arg Trp Met Cys Leu Arg Arg Phe Ile
145                 150                 155                 160
Ile Phe Leu Phe Ile Leu Leu Xaa Cys Leu Ile Phe Leu Leu Val Leu
                165                 170                 175
Leu Asp Tyr Gln Gly Met Leu Pro Val Cys Pro Leu Ile Pro Gly Ser
            180                 185                 190
Ser Thr Thr Ser Ala Gly Pro Cys Arg Thr Cys Thr Thr Thr Ala Gln
        195                 200                 205
Gly Thr Ser Met Tyr Pro Ser Cys Cys Thr Lys Pro Ser Asp Gly
210                 215                 220
Asn Cys Thr Cys Ile Pro Ile Pro Ser Ser Trp Ala Phe Gly Lys Leu
225                 230                 235                 240
Leu Trp Asp Trp Ala Ser Ala Arg Phe Ser Trp Leu Ser Leu Leu Val
                245                 250                 255
Pro Phe Val Gln Trp Phe Val Gly Leu Ser Pro Thr Val Trp Leu Ser
            260                 265                 270
Val Met Trp Met Met Trp Tyr Trp Gly Pro Ser Leu Tyr Ser Thr Leu
        275                 280                 285
Ser Pro Phe Leu Pro Leu Leu Pro Ile Phe Phe Cys Leu Trp Val Tyr
290                 295                 300
Ile
305

<210> SEQ ID NO 31
<211> LENGTH: 945
<212> TYPE: DNA
<213> ORGANISM: artificial sequence
<220> FEATURE:
<223> OTHER INFORMATION: pre ETV

<400> SEQUENCE: 31 gccataaccct tccaccaaac tctgcaagmt ccccctgctg gtggctccag ttccggaaca      60
gtaaaccctg ttccgactac tgcctctcac atatcgtcaa tcttctcgag gattggggac     120
cctgcgctga atatggagaa catcacatca ggattcctag gaccccttct cgtgttacag     180

```
gcggggtttt tcttgttgac aagaatcctc acaataccgm agagtctaga ctcgtggtgg    240
acttctctca attttctagg gggaaccacc gtgtgtcttg gccaaaattc gcagtcccca    300
acctccaatc actcaccaac ctcctgtcct ccgacttgac ctggttatcg ctggatgtgt    360
ctgcggcgtt ttatcatatt cctcttcatc ctgctgctat gcctcatctt cttgttggtt    420
cttctggact atcaaggtat gttgcccgtt tgtcctctaa ttccaggatc ctcaaccacc    480
agcacgggaa catgccgaac ttgcacgact cctgctcaag gaacctctat gtatccctcc    540
tgttgctgta ccaaaccttc ggacggaaat tgcacctgta ttcccatccc atcatcctgg    600
gctttcggaa aattcctatg ggagtgggcc tcagcccgtt tctcatggct cagtttasta    660
gtgccatttg ttcagtggtt cgtagggctt ccccccactg tttggctttc agttatgtgg    720
atgatgtggt attgggggcc aagtctgtac agcatcttga gtcccttttt accgctgtta    780
ccaattttct tttgtctctg gtatacatt tgaaccctaa caaaacaaag agatggggtt    840
actccctaaa ttttatgggc tatgtcattg gatgttatgg gtccttgcca caagaacaca    900
tcgtacataa aatcaaagaa tgttttagaa aacttcctgt taaca    945
```

<210> SEQ ID NO 32
<211> LENGTH: 1245
<212> TYPE: DNA
<213> ORGANISM: artificial sequence
<220> FEATURE:
<223> OTHER INFORMATION: on ETV

<400> SEQUENCE: 32

```
tgcctcattt tgtgggtcac catattcttg ggaacaagat ctacagcatg gggcagaatc     60
tttccaccag caatcctctg ggattctttc ccgaccacca gttggatcca gccttcagag    120
caaacaccgc aaatccagat tgggacttca atcccaacaa ggacacctgg ccagacgcca    180
acaaggtagg agctggagca ttcgggctgg gtttcacccc accgcacgga ggcctttgg     240 ggtggagccc tcaggctcag ggcatactac aaactttgcc agcaaagccg cctcctgcct    300
ccaccaatcg ccagtcagga cggcagccta ccccgctgtc tccacctttg agagacactc    360
atcctcaggc gcagtggaaa cccacaacct tccaccaaac tgtgcaagct ccacctgctg    420
gtggctccag ttccggaaca gtaaaccctg ttccgactac tgcctctcac atatcgtcaa    480
tcttctcgag gattggggac cctgcgctga atatggagaa catcacatca ggattcctag    540 gacccttct cgtgttacag gcggggtttt tcttgttgac aagaatcctc acaataccga    600
agagtctaga ctcgtggtgg acttctctca attttctagg gggaaccacc gtgtgtcttg    660
gccaaaattc gcagtcccca acctccaatc actcaccaac ctcctgtcct ccgacttgtc    720
ctggttatcg ctggatgtgt ctgcggcgtt ttatcatatt cctcttcatc ctgctgctat    780
gcctcatctt cttgttggtt cttctggact atcaaggtat gttgcccgtt tgtcctctaa    840
ttccaggatc ctcaaccacc agcacgggaa catgccgaac ttgcacgact cctgctcaag    900
gaacctctat gtatccctcc tgttgctgta ccaaaccttc ggacggaaat tgcacctgta    960
ttcccatccc atcatcctgg gctttcggaa aattcctatg ggagtgggcc tcagcccgtt   1020
tctcatggct cagtttggta gtgccatttg ttcagtggtt cgtagggctt ccccccactg   1080
tttggctttc atttatgtgg atgatgtggt attgggggcc aagtctgtac agcatcttga   1140
gtcccttttt accgctgtta ccaattttct tttgtctctg gtatacatt tgaaccctaa    1200 caaaacaaag agatggggtt actccctaaa ttttatgggg ctatg    1245
```

<210> SEQ ID NO 33

```
<211> LENGTH: 290
<212> TYPE: PRT
<213> ORGANISM: artificial sequence
<220> FEATURE:
<223> OTHER INFORMATION: pre ETV
<220> FEATURE:
<221> NAME/KEY: misc_feature
<222> LOCATION: (9)..(9)
<223> OTHER INFORMATION: Xaa = any amino acid
<220> FEATURE:
<221> NAME/KEY: misc_feature
<222> LOCATION: (73)..(73)
<223> OTHER INFORMATION: Xaa = any amino acid
<220> FEATURE:
<221> NAME/KEY: misc_feature
<222> LOCATION: (219)..(219)
<223> OTHER INFORMATION: Xaa = any amino acid

<400> SEQUENCE: 33

His Asn Leu Pro Pro Asn Ser Ala Xaa Ser Pro Cys Trp Trp Leu Gln
 1               5                  10                  15

Phe Arg Asn Ser Lys Pro Cys Ser Asp Tyr Cys Leu Ser His Ile Val
            20                  25                  30

Asn Leu Leu Glu Asp Trp Gly Pro Cys Ala Glu Tyr Gly Glu His His
        35                  40                  45

Ile Arg Ile Pro Arg Thr Pro Ser Arg Val Thr Gly Gly Val Phe Leu
    50                  55                  60

Val Asp Lys Asn Pro His Asn Thr Xaa Glu Ser Arg Leu Val Val Asp
65                  70                  75                  80

Phe Ser Gln Phe Ser Arg Gly Asn His Arg Val Ser Trp Pro Lys Phe
                85                  90                  95

Ala Val Pro Asn Leu Gln Ser Leu Thr Asn Leu Leu Ser Ser Asp Leu
            100                 105                 110

Thr Trp Leu Ser Leu Asp Val Ser Ala Ala Phe Tyr His Ile Pro Leu
        115                 120                 125

His Pro Ala Ala Met Pro His Leu Leu Val Gly Ser Ser Gly Leu Ser
    130                 135                 140

Arg Tyr Val Ala Arg Leu Ser Ser Asn Ser Arg Ile Leu Asn His Gln
145                 150                 155                 160

His Gly Asn Met Pro Asn Leu His Asp Ser Cys Ser Arg Asn Leu Tyr
                165                 170                 175

Val Ser Leu Leu Leu Leu Tyr Gln Thr Phe Gly Arg Lys Leu His Leu
            180                 185                 190

Tyr Ser His Pro Ile Ile Leu Gly Phe Arg Lys Ile Pro Met Gly Val
        195                 200                 205

Gly Leu Ser Pro Phe Leu Met Ala Gln Phe Xaa Ser Ala Ile Cys Ser
    210                 215                 220

Val Val Arg Arg Ala Phe Pro His Cys Leu Ala Phe Ser Tyr Val Asp
225                 230                 235                 240

Asp Val Val Leu Gly Ala Lys Ser Val Gln His Leu Glu Ser Leu Phe
                245                 250                 255

Thr Ala Val Thr Asn Phe Leu Leu Ser Leu Gly Ile His Leu Asn Pro
            260                 265                 270

Asn Lys Thr Lys Arg Trp Gly Tyr Ser Leu Asn Phe Met Gly Tyr Val
        275                 280                 285

Ile Gly
    290

<210> SEQ ID NO 34
<211> LENGTH: 251
```

```
<212> TYPE: PRT
<213> ORGANISM: artificial sequence
<220> FEATURE:
<223> OTHER INFORMATION: on ETV

<400> SEQUENCE: 34

Glu Asp Trp Gly Pro Cys Ala Glu Tyr Gly His His Ile Arg Ile
1               5                   10                  15

Pro Arg Thr Pro Ser Arg Val Thr Gly Gly Val Phe Leu Val Asp Lys
            20                  25                  30

Asn Pro His Asn Thr Glu Glu Ser Arg Leu Val Val Asp Phe Ser Gln
            35                  40                  45

Phe Ser Arg Gly Asn His Arg Val Ser Trp Pro Lys Phe Ala Val Pro
50                  55                  60

Asn Leu Gln Ser Leu Thr Asn Leu Leu Ser Ser Asp Leu Ser Trp Leu
65                  70                  75                  80

Ser Leu Asp Val Ser Ala Ala Phe Tyr His Ile Pro Leu His Pro Ala
                85                  90                  95

Ala Met Pro His Leu Leu Val Gly Ser Ser Gly Leu Ser Arg Tyr Val
                100                 105                 110

Ala Arg Leu Ser Ser Asn Ser Arg Ile Leu Asn His Gln His Gly Asn
            115                 120                 125

Met Pro Asn Leu His Asp Ser Cys Ser Arg Asn Leu Tyr Val Ser Leu
130                 135                 140

Leu Leu Leu Tyr Gln Thr Phe Gly Arg Lys Leu His Leu Tyr Ser His
145                 150                 155                 160

Pro Ile Ile Leu Gly Phe Arg Lys Ile Pro Met Gly Val Gly Leu Ser
                165                 170                 175

Pro Phe Leu Met Ala Gln Phe Gly Ser Ala Ile Cys Ser Val Val Arg
                180                 185                 190

Arg Ala Phe Pro His Cys Leu Ala Phe Ile Tyr Val Asp Asp Val Val
            195                 200                 205

Leu Gly Ala Lys Ser Val Gln His Leu Glu Ser Leu Phe Thr Ala Val
210                 215                 220

Thr Asn Phe Leu Leu Ser Leu Gly Ile His Leu Asn Pro Asn Lys Thr
225                 230                 235                 240

Lys Arg Trp Gly Tyr Ser Leu Asn Phe Met Gly
                245                 250

<210> SEQ ID NO 35
<211> LENGTH: 110
<212> TYPE: PRT
<213> ORGANISM: artificial sequence
<220> FEATURE:
<223> OTHER INFORMATION: pre ETV
<220> FEATURE:
<221> NAME/KEY: misc_feature
<222> LOCATION: (8)..(8)
<223> OTHER INFORMATION: X = any amino acid
<220> FEATURE:
<221> NAME/KEY: misc_feature
<222> LOCATION: (72)..(72)
<223> OTHER INFORMATION: Xaa = any amino acid

<400> SEQUENCE: 35

Thr Phe His Gln Thr Leu Gln Xaa Pro Pro Ala Gly Gly Ser Ser Ser
1               5                   10                  15

Gly Thr Val Asn Pro Val Pro Thr Thr Ala Ser His Ile Ser Ser Ile
            20                  25                  30

Phe Ser Arg Ile Gly Asp Pro Ala Leu Asn Met Glu Asn Ile Thr Ser
```

```
                35                  40                  45
Gly Phe Leu Gly Pro Leu Leu Val Leu Gln Ala Gly Phe Phe Leu Leu
 50                  55                  60

Thr Arg Ile Leu Thr Ile Pro Xaa Ser Leu Asp Ser Trp Trp Thr Ser
 65                  70                  75                  80

Leu Asn Phe Leu Gly Thr Thr Val Cys Leu Gly Gln Asn Ser Gln
                 85                  90                  95

Ser Pro Thr Ser Asn His Ser Pro Thr Ser Cys Pro Pro Thr
                100                 105                 110

<210> SEQ ID NO 36
<211> LENGTH: 226
<212> TYPE: PRT
<213> ORGANISM: artificial sequence
<220> FEATURE:
<223> OTHER INFORMATION: post ETV

<400> SEQUENCE: 36

Met Glu Asn Ile Thr Ser Gly Phe Leu Gly Pro Leu Leu Val Leu Gln
 1               5                  10                  15

Ala Gly Phe Phe Leu Leu Thr Arg Ile Leu Thr Ile Pro Lys Ser Leu
                 20                  25                  30

Asp Ser Trp Trp Thr Ser Leu Asn Phe Leu Gly Gly Thr Thr Val Cys
                 35                  40                  45

Leu Gly Gln Asn Ser Gln Ser Pro Thr Ser Asn His Ser Pro Thr Ser
 50                  55                  60

Cys Pro Pro Thr Cys Pro Gly Tyr Arg Trp Met Cys Leu Arg Arg Phe
 65                  70                  75                  80

Ile Ile Phe Leu Phe Ile Leu Leu Leu Cys Leu Ile Phe Leu Leu Val
                 85                  90                  95

Leu Leu Asp Tyr Gln Gly Met Leu Pro Val Cys Pro Leu Ile Pro Gly
                100                 105                 110

Ser Ser Thr Thr Ser Thr Gly Thr Cys Arg Thr Cys Thr Thr Pro Ala
                115                 120                 125

Gln Gly Thr Ser Met Tyr Pro Ser Cys Cys Cys Thr Lys Pro Ser Asp
                130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Val
                165                 170                 175

Val Pro Phe Val Gln Trp Phe Val Gly Leu Ser Pro Thr Val Trp Leu
                180                 185                 190

Ser Phe Met Trp Met Met Trp Tyr Trp Gly Pro Ser Leu Tyr Ser Ile
                195                 200                 205

Leu Ser Pro Phe Leu Pro Leu Leu Pro Ile Phe Phe Cys Leu Trp Val
                210                 215                 220

Tyr Ile
225
```